United States Patent

Almen et al.

[11] Patent Number: 5,993,780
[45] Date of Patent: *Nov. 30, 1999

[54] CONTRAST MEDIA

[75] Inventors: Torsten Almen, Falsterbo; Sven Göran Andersson, Lomma; Lars-Göran Wistrand, Lund, all of Sweden; Klaes Golman, Rungsted Kyst, Denmark; Øyvind Antonsen, Gjesasen, Norway; Rune Fossheim, Oslo, Norway; Unni Nordby Wiggen, Rasta, Norway; Håkan Wikström, Groningen, Netherlands; Tomas Klingstedt, Lund, Sweden; Ib Leunbach, Dragör, Denmark; Arne Berg, Blommenholm; Harald Dugstad, Oslo, both of Norway

[73] Assignee: Nycomed Imaging AS, Norway

[*] Notice: This patent is subject to a terminal disclaimer.

[21] Appl. No.: 08/826,077

[22] Filed: Mar. 24, 1997

Related U.S. Application Data

[63] Continuation-in-part of application No. PCT/GB95/02265, Sep. 22, 1995, and a continuation-in-part of application No. 08/470,042, Jun. 6, 1995, Pat. No. 5,882,628.

[30] Foreign Application Priority Data

Sep. 23, 1994 [GB] United Kingdom .................. 9419203

[51] Int. Cl.⁶ ......................... A61K 49/00; C07C 233/00
[52] U.S. Cl. ...................... 424/9.452; 564/153; 514/546; 514/751; 514/754; 560/130; 560/141; 560/142; 568/812
[58] Field of Search ..................... 564/153; 424/9.452; 514/546, 751, 754; 560/130, 141, 142

[56] References Cited

U.S. PATENT DOCUMENTS

| | | | |
|---|---|---|---|
| 4,314,055 | 2/1982 | Hoey et al. | 536/53 |
| 5,047,228 | 9/1991 | Gries et al. | 564/153 |
| 5,616,798 | 4/1997 | Zrihen et al. | 564/153 |
| 5,618,977 | 4/1997 | Dugast-Zrihen et al. | 564/153 |
| 5,663,413 | 9/1997 | Uggeri et al. | 560/59 |

FOREIGN PATENT DOCUMENTS

WO 95/15307  6/1995  WIPO.

OTHER PUBLICATIONS

Hebky et al Coll. Czech. Chem. Comm., vol. 35, pp. 667–674, 1970.

Primary Examiner—Shailendra Kumar
Attorney, Agent, or Firm—Bacon & Thomas PLLC

[57] ABSTRACT

The invention provides low viscosity iodinated aryl compounds, useful as X-ray contrast agents, of formula I

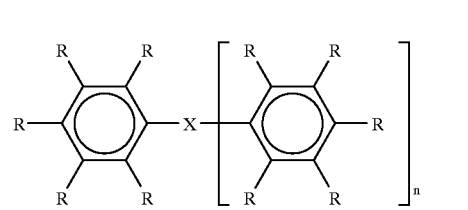

(I)

(wherein n is 0 or 1, and where n is 1 each $C_6R_5$ moiety may be the same or different; each group R is a hydrogen atom, an iodine atom or a hydrophilic moiety M or $M_1$, two or three non-adjacent R groups in each $C_6R_5$ moiety being iodine and at least one, and preferably two or three, R groups in each $C_6R_5$ moiety being M or $M_1$ moieties; X denotes a bond or a group providing a 1 to 7 atom chain linking two $C_6R_5$ moieties or, where n is 0, X denotes a group R; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group being an $M_1$ moiety; with the proviso that where n is zero either at least one $M_1$ group other than a hydroxymethyl or 1,2-dihydroxyethyl group is present or then if one hydroxymethyl or 1,2-dihydroxyethyl $M_1$ group is present at least one nitrogen-attached or hydroxylated-$C_{3-4}$ alkyl moiety-containing M group is also present) and isomers thereof.

26 Claims, No Drawings

CONTRAST MEDIA

RELATED APPLICATIONS

This application is a continuation-in-part of the US designation of International Patent Application No. PCT/GB95/02265, filed Sep. 22, 1995 and a continuation-in-part of U.S. patent application Ser. No. 08/470,042, filed Jun. 6, 1995, now U.S. Pat. No. 5,882,628.

FIELD OF THE INVENTION

This invention relates to improvements in and relating to contrast media, and in particular iodinated X-ray contrast media.

BACKGROUND OF THE INVENTION

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging, the contrast media function by modifying the X-ray absorption characteristics of the body sites into which they distribute.

Clearly however the utility of a material as a contrast medium is governed largely by its toxicity, by its diagnostic efficacy, by other adverse effects it may have on the subject to which it is administered, and by its ease of storage and ease of administration.

Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse biological effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:

the chemotoxicity of the contrast agent, the osmolality of the contrast medium, and the ionic composition (or lack thereof) of the contrast medium.

In coronary angiography, for example, injection into the circulatory system of contrast media has been associated with several serious effects on cardiac function. These effects are sufficiently severe as to place limitations on the use in angiography of certain contrast media.

In this procedure, for a short period of time a bolus of contrast medium rather than blood flows through the circulatory system and differences in the chemical and physicochemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

Early injectable ionic X-ray contrast agents, based on triiodophenylcarboxylate salts, were particularly associated with osmotoxic effects deriving from the hypertonicity of the contrast media injected.

This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

The osmotoxicity problem was addressed by the development of the non-ionic triiodophenyl monomers, such as iohexol, which allowed the same contrast effective iodine concentrations to be attained with greatly reduced attendant osmotoxicity effects.

The drive towards reduced osmotoxicity led in due course to the development of the non-ionic bis(triiodophenyl) dimers, such as iodixanol, which reduce osmotoxicity associated problems still further allowing contrast effective iodine concentrations to be achieved with hypotonic solutions.

This ability to achieve contrast effective iodine concentrations without taking solution osmolality up to isotonic levels (about 300 mOsm/kg $H_2O$) further enabled the contribution to toxicity of ionic imbalance to be addressed by the inclusion of various plasma cations, as discussed for example in WO-90/01194 and WO-91/13636 of Nycomed Imaging AS.

However X-ray contrast media, at commercial high iodine concentrations of about 300 mgI/mL have relatively high viscosities, ranging from about 15 to about 60 mPas at ambient temperature with the dimeric media generally being more viscous than the monomeric media. Such viscosities pose problems to the administrator of the contrast medium, requiring relatively large bore needles or high applied pressure, and are particularly pronounced in paediatric radiography and in radiographic techniques which require rapid, bolus administration, e.g. in angiography.

In practice, viscosities in excess of 30 mPas at body temperature (37° C.) are unacceptably high for routine X-ray investigations, and especially for paediatric investigations. Accordingly, the maximum practical iodine concentration achievable with available non-ionic iodinated X-ray contrast agents is generally about 300–350 mgI/mL. Higher iodine concentrations, if accessible at acceptable viscosities, would increase the diagnostic efficacy of contrast enhanced images. Alternatively viewed, lower contrast medium viscosities for any given iodine concentration would increase ease of administration and the range of investigations and patients for which the contrast media could be used.

SUMMARY OF THE INVENTION

The present invention addresses the viscosity problem encountered with the prior art materials and thus viewed from one aspect the invention provides iodinated aryl compounds, useful as X-ray contrast agents, of formula I

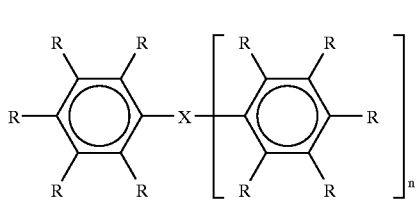

(I)

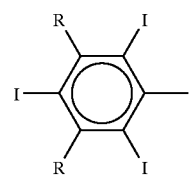

(wherein n is 0 or 1, and where n is 1 each $C_6R_5$ moiety may be the same or different; each group R is a hydrogen atom, an iodine atom or a hydrophilic moiety M or $M_1$, two or three non-adjacent R groups in each $C_6R_5$ moiety being iodine and at least one, and preferably two or three, R groups in each $C_6R_5$ moiety being M or $M_1$ moieties; X denotes a bond or a group providing a 1 to 7, for example 1, 2, 3 or 4 atom chain linking two $C_6R_5$ moieties or, where n is 0, X denotes a group R; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group, preferably at least two R groups and especially preferably at least one R group in each $C_6R_5$ moiety, being an $M_1$ moiety; with the proviso that where n is zero either at least one $M_1$ group other than a hydroxymethyl or 1,2-dihydroxyethyl (and optionally other than any hydroxyethyl) group is present or then if one hydroxymethyl or 1,2-dihydroxyethyl $M_1$ group (and optionally any hydroxyethyl group) is present at least one nitrogen-attached hydroxylated alkyl (preferably $C_{1-4}$-alkyl) moiety-containing M group is also present) and isomers, especially stereoisomers and rotamers, thereof.

DETAILED DESCRIPTION OF THE INVENTION

It is found that the compounds of the invention exhibit advantageously low viscosity in aqueous solution; this is thought to derive from the presence of $M_1$ groups on the phenyl groups, from compound asymmetry and, in the dimer compounds, from the nature of the linker X (especially where X provides a linkage less than 5 atoms in length).

Thus for example all of the water-soluble monomer compounds according to the invention that have been tested have exhibited viscosities lower than that of iohexol.

The compounds of formula I are preferably asymmetric. For the monomer compounds (where n=0) this may be achieved by asymmetric substitution of the phenyl ring. For the dimers this can be achieved by the use of an asymmetric 2 or more atom chain-forming group X and/or by selection of non-identical $C_6R_5$ groups, i.e. by non-identical substitution of the iodophenyl end groups. Asymmetric molecules are preferred as they have been found to have better water-solubility.

Such non-identical substitution of the phenyl end groups, the $C_6R_5$ moieties, may be achieved by having different numbers or positions of iodine substitution and/or by different numbers, positions or identities of M or $M_1$ substitution. To maximize iodine loading, triiodophenyl end groups, i.e. groups of formula are preferred, and in these the two R groups may be the same or different, although preferably both represent M or $M_1$ groups.

Where a phenyl end group is disubstituted by iodine, it is preferably of formula

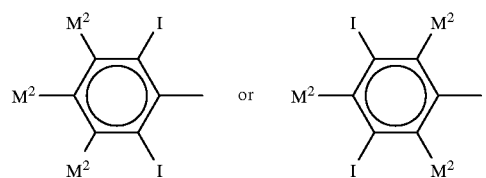

(where each $M^2$ may be the same or different and represents an $M_1$ or M group, at least one on each ring preferably representing an $M_1$ group).

Generally, diiodophenyl-diiodophenyl dimers will be less preferred than the diiodophenyl-triiodophenyl or triiodophenyl—triiodophenyl dimers, due primarily to their reduced iodine loading, i.e. 4 rather than 5 or 6 iodines per dimer molecule. Indeed the triiodophenyl—triiodophenyl dimers are generally preferred due to their higher iodine loading.

For the monomers, the triiodophenyl compounds are again preferred.

The solubilizing groups M may be any of the non-ionizing groups conventionally used to enhance water solubility. Suitable groups include for example a straight chain or branched $C_{1-10}$-alkyl group, preferably a $C_{1-5}$ group, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups. Preferred among such groups are those containing 1, 2, 3, 4, 5 or 6, especially 1, 2 or 3, hydroxy groups, e.g.

—CONH—$CH_2CH_2OH$
—CONH—$CH_2CHOHCH_2OH$
—CONH—$CH(CH_2OH)_2$
—CON $(CH_2CH_2OH)_2$ as well as other groups such as —$CONH_2$
—$CONHCH_3$
—$OCOCH_3$
—$N(COCH_3)H$
—$N(COCH_3)C_{1-3}$-alkyl
—$N(COCH_3)$-mono, bis or tris-hydroxy $C_{1-4}$-alkyl
—$N(COCH_2OH)$-mono, bis or tris-hydroxy $C_{1-4}$-alkyl
—$N(COCH_2OH)_2$
—$CON(CH_2CHOHCH_2OH)(CH_2CH_2OH)$
—CONH—$C(CH_2OH)_3$ and
—CONH—$CH(CH_2OH)(CHOHCH_2OH)$.

In general, the $M^1$ groups will preferably each comprise a polyhydroxy $C_{1-4}$-alkyl group, such as 1,3-dihydroxyprop-2-yl or 2,3-dihydroxyprop-1-yl.

Other such M groups as are conventional within the field of triiodophenyl X-ray contrast agents may also be used and the introduction of M groups onto iodophenyl structures may be achieved by conventional techniques.

In general, $M_1$ groups preferably comprise $C_{1-4}$-alkyl groups substituted by 1, 2, 3 or 4 hydroxy groups (e.g. hydroxymethyl, 2-hydroxyethyl, 2,3-bishydroxypropyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$).

In the dimeric compounds of the invention, the linker group X is conveniently a bond or a 1 to 7, e.g. 1, 2, 3 or 4, membered chain comprising carbon, nitrogen, oxygen or sulphur atoms, e.g.

a bond, a O, S, N or C one atom chain, a NN, NC, NS, CC or CO two atom chain, or a NCN, OCN, CNC, OCO, NSN, CSN, COC, OCC or CCC three atom chain, for example:

an oxygen atom or a group $NR^1$, CO, $SO_2$ or $CR_2^1$;

a group COCO, $CONR^1$, $COCR_2^1$, $SOCR_2^1$, $SO_2NR^1$, $CR_2^1CR_2^1$, $CR_2^1NR^1$ or $CR_2^1O$;

a group $NR^1CONR^1$, $OCONR^1$, $CONR^1CO$, $CONR^1CR_2^1$, OCOO, $CR_2^1OCR_2^1$, $OCR_2^1CO$, $CR_2^1CONR^1$, $CR_2^1CR_2^1CR_2^1$, $COCR^1R^1CO$, $CR_2^1NR^1CR_2^1$, $CR_2^1SO_2NR^1$, $CR_2^1OCO$ or $NR^1SO_2NR^1$;

where $R^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group) and where it is attached to a carbon atom $R^1$ may also be a hydroxyl group.

When X provides a 4–7 atom linkage, conventional linker groups, such as for example those suggested by Justesa in WO-93/10078 or Bracco in U.S. Pat. No. 4,348,377 and WO-94/14478 may be used.

In general such linkages will comprise optionally aza or oxa substituted alkylene chains optionally carrying $R^1$ substituents, especially such groups terminating with imine nitrogen or, more preferably, carbonyl carbon atoms, preferably belonging to aminocarbonyl functional units within the chain. Hydroxylated chains, such as are found in iodixanol are particularly preferred.

Examples of such chains are NCCN, NCCCN, CNCCCNC, and CNCCN, eg.

—$NR^1COCONR^1$—

—$NR^1COCR^1_2CONR^1$—

—$NR^1CR^1_2CR^1OHCR^1_2NR^1$—

—$CONR^1CR^1_2CONR^{1-}$ and

—$N(COR^1)CR^1_2CR^1OHN(COR^1)$—, eg as found in iotrolan, iofratol, ioxaglic acid and iodixanol, or as otherwise indicated in WO-94/14478.

Advantageously, in the dimer compounds the X group is not symmetrical. This may be achieved for example by asymmetrical substitution of a symmetrical chain (e.g. N—C—N substituted as $NHCONR^1$) or by selection of an asymmetric chain (e.g. OCN substituted as $OCONR^1$). In particular, it is preferred that the linker group X should be polar and also that it should be hydrophilic.

Thus examples of preferred structures according to the invention include:

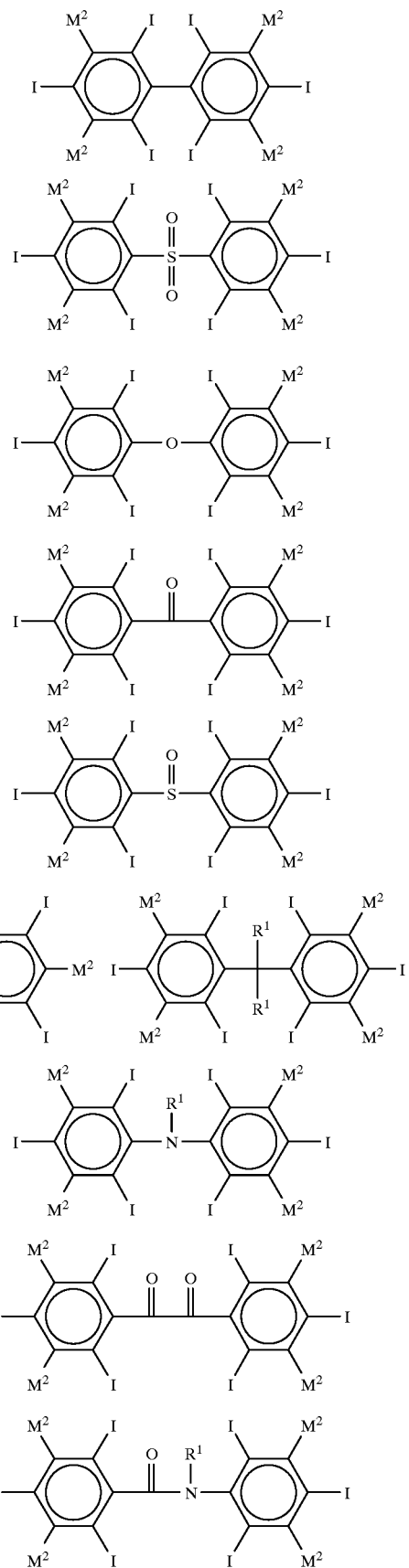

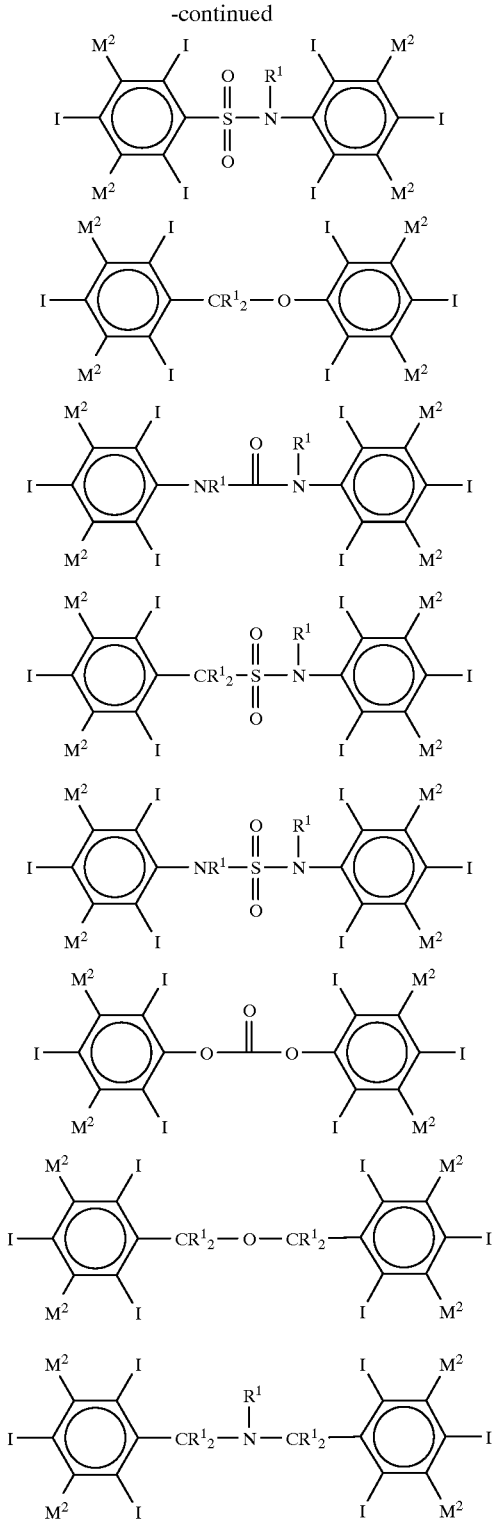

2,3-bishydroxy-propyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$), e.g. a hydroxyalkyl or hydroxyalkylcarbonyl group, in particular a hydroxymethyl, hydroxymethylcarbonyl, 2-hydroxyethyl or 2-hydroxyethylcarbonyl group, and where $R^1$ is hydrogen, hydroxyl, hydroxyalkyl (e.g. 2-hydroxyethyl), acetyl or hydroxyalkylcarbonyl.

Particular preferred compounds are those of formula

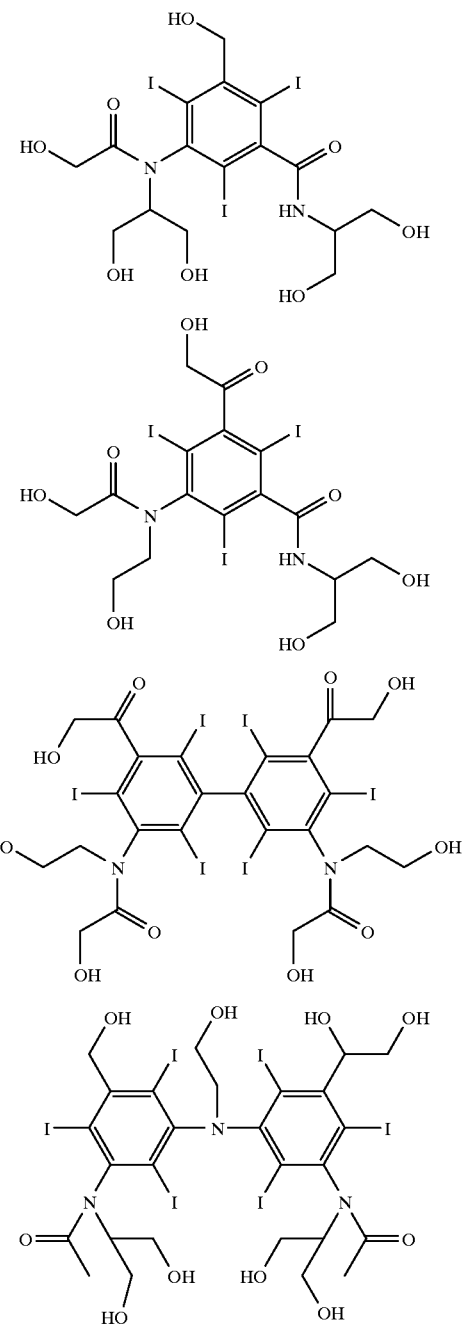

where each $M^2$ is $M_1$ or M, at least one in each compound (and preferably on each ring) being $M_1$, especially where at least one $M^2$ is a $C_{1-4}$-alkyl group substituted by 1, 2, 3 or 4 hydroxy groups (e.g. hydroxymethyl, 2-hydroxyethyl,

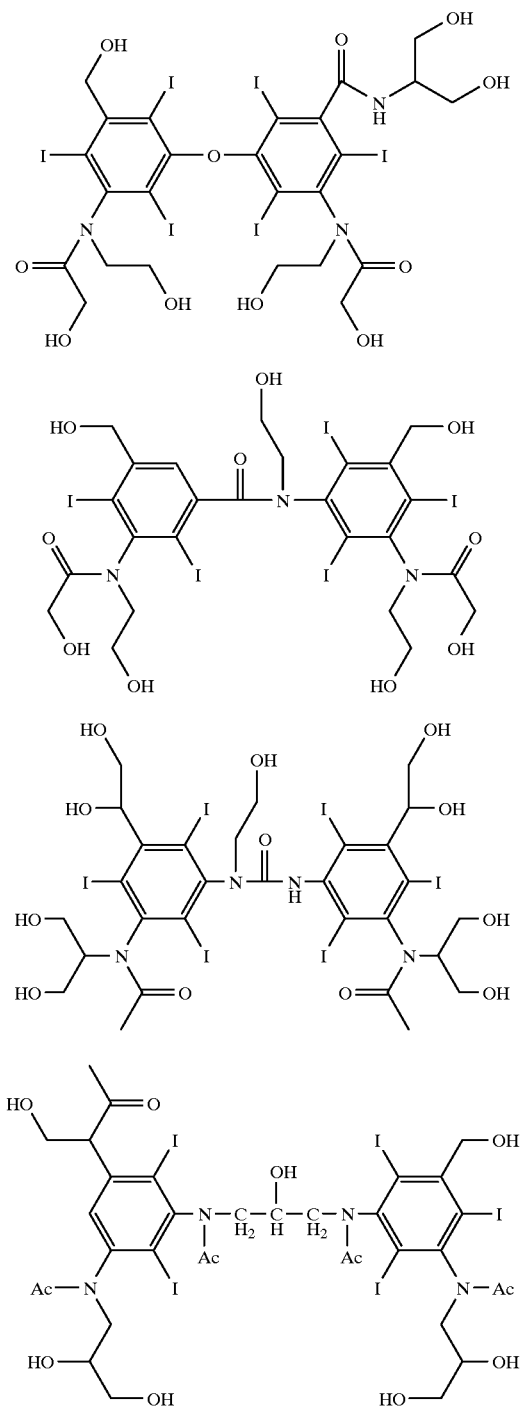

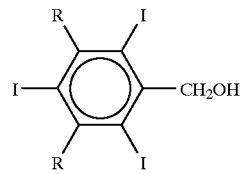

(II)

where each R group, which may be the same or different, is a non-ionic hydrophilic moiety (e.g. as defined above, preferably a group containing up to 10, more preferably 1 to 6, especially 2 to 4 hydroxyl groups), or one R group may be a second non-ionic triiodophenyl group, attached directly or via a non-ionic organic linker moiety.

Preferably the compounds of formula II are monomeric and especially preferably the two R groups are hydroxylated alkylcarbonylamino or hydroxylated alkyaminocarbonyl groups wherein the alkyl moieties contain 1 to 6 carbons and the amide nitrogens are optionally alkylated by optionally hydroxylated $C_{1-6}$ groups.

It has surprisingly been found that where the triiodophenyl ring carries a hydroxymethyl substituent, i.e. a small mono-hydroxylated group, especially high iodine concentrations can be achieved at relatively low or acceptable viscosities.

Thus viewed from a further aspect the invention provides a non-ionic iodinated X-ray contrast agent compound comprising a 1-hydroxymethyl-2,4,6-triiodobenzene ring structure, having a water solubility of at least 400 mgI/mL at 20° C., and having a viscosity of less than 30 mPas in aqueous solution at 20° C. and a concentration of 400 mgI/mL, preferably having a viscosity of less than 30 mPas in aqueous solution at 20° C. and a concentration of 450 mgI/mL.

Particularly preferably, the compounds have viscosities at 400 mgI/mL aqueous solution at 20° C. of less than 20 mPas.

Viewed from a further aspect the invention provides non-ionic 2,4,5-triiodobenzyl alcohols having a nitrogen attached substitutent, preferably a hydroxylated substituent, at at least one of the 3- and 5-positions.

Particularly preferably the compounds of the invention have the formula III

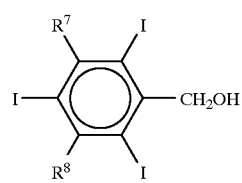

(III)

where $R^7$ and $R^8$, which may be the same or different, are $CH_2OH$, $R^{10}CONR^9$ or $R^{10}CONR^9$;

each $R^9$, which may be the same or different, is hydrogen or a linear or branched hydroxylated $C_{1-6}$ alkyl; and each $R^{10}$ which may be the same or different is a linear or branched hydroxylated $C_{1-6}$ alkyl.

Examples of suitable $R^9$ and $R^{10}$ groups include H, $CH_2OH$, $CHOHCH_3$, $CH_2CH_2OH$, $CHOHCH_2OH$, $C(CH_3)(CH_2OH)_2$, $C(CH_2OH)_3$, $CH_2CHOHCH_2OH$ and $CH(CH_2OH)CHOHCH_2OH$.

Examples of suitable $R^{10}CONR^9$ groups include $HOCH_2CON(CH_2CHOHCH_2OH)$, $HOCH_2CONH$, It is especially preferred that a hydroxymethyl $M_1$ group be present in the compounds of the invention and in particular that the compounds be hydroxymethyl substituted monomers.

Thus viewed from a further aspect the invention provides compounds of formula II HOCH$_2$CON(CH$_2$CH$_2$OH), CH$_3$CHOHCONH, CH$_3$CHOHCON(CH$_2$CH$_2$OH), CH$_3$CHOHCON(CH$_2$CHOHCH$_2$OH), HOCH$_2$CHOHCONH, HOCH$_2$CHOHCON(CH$_2$CH$_2$OH), OHCH$_2$CHOHCON(CH$_2$CHOHCH$_2$OH), (CH$_2$OH)$_2$(CH$_3$)CCONH, (CH$_2$OH)$_2$CHCONH, HOCH$_2$CH$_2$CONH, (CH$_2$OH)$_3$CCONH, HOCH$_2$CON(CH$_2$CHOHCH$_2$OH), and HOCH$_2$CHOHCHOHCONH.

Examples of particularly suitable R$^{10}$N(R$^9$)CO groups include HOCH$_2$CHOHCH$_2$NHCO and, HOCH$_2$CHOHCH(CH$_2$OH)NHCO, (HOCH$_2$CH$_2$)$_2$NCO, HOCH$_2$CHOHCH$_2$N(CH$_3$)CO, (HOCH$_2$)$_2$CHNHCO, HOCH$_2$CH$_2$NHCO, and (HOCH$_2$)$_3$CNHCO.

Further preferred compounds include those of formula IV

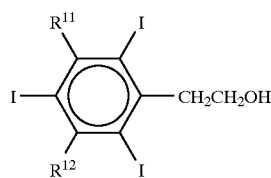

(IV)

wherein R$^{11}$ and R$^{12}$, which may be the same or different are groups R$^{10}$CONR$^9$ or R$^{10}$NR$^9$CO as defined above with the proviso that at least one is a group R$^{10}$CONR$^9$.

In the compounds of formulae III and IV, and indeed in all the compounds according to the invention, the triiodophenyl ring substituents preferably carry a total of 4 to 7 hydroxyl groups.

In the compounds of formula III, conveniently: (i) one of R$^7$ and R$^8$ is N attached (and the other is CO attached) and the R$^{10}$CO group is hydroxylated; (ii) both R$^7$ and R$^8$ are CO attached; or (iii) both R$^7$ and R$^8$ are nitrogen attached and at least one R$^{10}$ is other than HOCH$_2$, HOCH$_2$CHOH or CH$_3$CHOH.

The compounds of the invention may in general be prepared in two or three stages: (a) dimer formation (where necessary), (b) iodination of phenyl groups and (c) substitution of phenyl groups and/or optionally linker moieties by solubilizing moieties.

While, in theory, stages (a), (b) and (c) can be performed in any order, it will generally be preferred to perform the dimer formation step before the iodination step and, for reasons of economy, it will be preferred to perform the iodination step at as late a stage in the synthesis as is feasible so as to reduce iodine wastage. The dimer formation stage may itself be a multi-step procedure with an appropriate activated linker first being attached to one monomer before the resulting linker-monomer conjugate is reacted with a second monomer. Alternatively, dimer formation may be by way of reaction of similarly or cooperatively substituted monomers with the conjugation of the monomers leading to dimer formation.

Where desired the linker group X may be produced by modification, e.g. substitution, oxidation or reduction, of a precursor linker, e.g. in a precursor monomer.

For the monomer compounds, especially those where ring substitution is asymmetric, iodine loading will generally be effected before or after partial substitution of the phenyl ring with R groups.

In all cases, conventional synthetic routes well known in the literature (eg methods analogous to those used and described for the production of the compounds referred to in WO-94/14478) may be used.

The compounds of the invention may be used as X-ray contrast agents and to this end they may be formulated with conventional carriers and excipients to produce diagnostic contrast media.

Thus viewed from a further aspect the invention provides a diagnostic composition comprising a compound according to the invention (as defined above) together with at least one physiologically tolerable carrier or excipient, e.g. in aqueous solution in water for injections optionally together with added plasma ions or dissolved oxygen.

The contrast agent compositions of the invention may be at ready-to-use concentrations or may be formulated in concentrate form for dilution prior to administration. Generally compositions in ready-to-use form will have iodine concentrations of at least 100 mgI/ml, preferably at least 150 mgI/ml, with concentrations of at least 300 mgI/ml, e.g. 320 to 600 mgI/ml being generally preferred. The higher the iodine concentration the higher the diagnostic value but equally the higher the solution's viscosity and osmolality. Normally the maximum iodine concentration for a given compound will be determined by its solubility, and by the upper tolerable limits for viscosity and osmolality.

For contrast media which are administered by injection, the desirable upper limit for solution viscosity at ambient temperature (20° C.) is 30 mPas; however viscosities of up to 50 or even up to 60 mPas can be tolerated although their use in paediatric radiography will then generally be contraindicated. For contrast media which are to be given by bolus injection, e.g. in angiographic procedures, osmotoxic effects must be considered and preferably osmolality should be below 1 Osm/kg H$_2$O, especially below 850 mOsm/kg H$_2$O, in particular within 50 or less, preferably within 10, mOsm of isotonicity (about 300 mOsm/kg H$_2$O).

With the compounds of the invention, such viscosity, osmolality and iodine concentration targets can readily be met. Indeed effective iodine concentrations may be reached with hypotonic solutions. It may thus be desirable to make up solution tonicity by the addition of plasma cations so as to reduce the toxicity contribution which derives from ionic imbalance effects following bolus injection. Such cations will desirably be included in the ranges suggested in WO-90/01194 and WO-91/13636.

Preferred plasma cation contents for the contrast media of the invention, especially contrast media for angiography, are as follows:

| | |
|---|---|
| sodium | 2 to 100, especially 15 to 75, particularly 20 to 70, more particularly 25 to 35 mM |
| calcium | up to 3.0, preferably 0.05 to 1.6, especially 0.1 to 1.2, particularly 0.15 to 0.7 mM |
| potassium | up to 2, preferably 0.2 to 1.5, especially 0.3 to 1.2, particularly 0.4 to 0.9 mM |
| magnesium | up to 0.8, preferably 0.05 to 0.6, especially 0.1 to 0.5, particularly 0.1 to 0.25 mM |

The plasma cations may be presented, in whole or in part, as counterions in ionic contrast agents. Otherwise they will generally be provided in the form of salts with physiologically tolerable counteranions, e.g. chloride, sulphate, phosphate, hydrogen carbonate, etc., with plasma anions especially preferably being used.

Besides plasma cations, the contrast media may contain other counterions where the dimer is ionic and such counterions will of course preferably be physiologically tolerable. Examples of such ions include alkali and alkaline earth metal ions, ammonium, meglumine, ethanolamine, diethanolamine, chloride, phosphate, and hydrogen carbonate. Other counterions conventional in pharmaceutical formulation may also be used. The compositions moreover may contain further components conventional in X-ray contrast media, e.g. buffers, etc.

Publications referred to herein are incorporated herein by reference.

The invention will now be described further with reference to the following non-limiting Examples.

EXAMPLE 1

1,3,5-Triiodo-2,4-di(1,2,3-trihydroxy-1-propyl)-6-(3-hydroxy-1-propen-1-yl)benzene a. 1,3,5-Triiodo-2,4,6-trimethylbenzene Iodine (19.0 g, 75 mmol) was dissolved in carbon tetrachloride (75 ml). Mesitylene (7.0 ml, 50 mmol) and bis(trifluoroacetoxy)phenyl iodide (35.5 g, 82 mmol) were added and the solution was stirred at ambient temperature for 2 hours. The precipitate, which was collected by filtration, was washed with cold carbon tetrachloride and dried. Yield: 20.5 g (82%).

$^1$H NMR (CDCl$_3$): 3.31 (s).

b. 1,3,5-Triiodo-2,4,6-triacetoxymethylbenzene

Triiodomesitylene (19.5 g, 39 mmol) was added to glacial acetic acid (200 ml) containing acetic anhydride (400 ml) and concentrated sulfuric acid (40 ml). Solid potassium permanganate (24.6 g, 156 mmol) was then added in small portions over a period of 3 h. After stirring for 16 h, the solvent was evaporated and water (200 ml) was added. The aqueous suspension was extracted with dichloromethane (250 ml) and the organic phase was washed with water (3×50 ml), dried (MgSO$_4$) and evaporated. The solid residue was suspended in acetone and the white crystalline product was collected by filtration. Yield: 9.3 g (35%).

$^1$H NMR (CDCl$_3$): 5.66 (s, 6H), 2.20 (s, 9H).

c. 1,3,5-Triiodo-2,4,6-trihydroxymethylbenzene 1,3,5-Triiodo-2,4,6-triacetoxymethylbenzene (9.3 g, 13.8 mmol) was suspended in methanol (120 ml) and K$_2$CO$_3$ (0.32 g, 2.3 mmol) was added. The mixture was stirred at ambient temperature for 16 h, and, after neutralization of the solution with 2M aqueous HCl, the organic solvent was evaporated. The residue was suspended in water and the white solid was collected by filtration and washed with water, methanol and ether. Yield: 7.1 g (94%).

$^1$H NMR (DMSO-d$_6$): 5.08 (s, 6H), 3.35 (br s, 3H).

d. 1,3,5-Triiodobenzene-2,4,6-trialdehyde 1,3,5-Triiodo-2,4,6-trihydroxymethylbenzene (4.5 g, 8.2 mmol) was dissolved in DMSO (80 ml). Triethylamine (51.7 ml, 371 mmol) and pyridine.SO$_3$ (11.8 g, 74.2 mmol) were added and the mixture was stirred for two hours. The two phases were separated and the lower phase was cooled to 0° C., poured into water (150 ml) and stirred for 30 min at 0° C. The white solid was collected by filtration, washed with water and dried. Yield: 3.0 g (67%).

$^1$H NMR (DMSO-d$_6$): 9.64 (s)

e. 1,3,5-Triiodo-2,4,6-tris(2-prop-1-enoic acid)benzene methyl ester

Sodium hydride (194 mg 80% in mineral oil, 6.5 mmol) was dissolved in DMSO (13 ml) and triethylphosphonoacetate (1.16 ml, 5.80 mmol) was added. After stirring the solution for 30 min, 1,3,5-triiodobenzene-2,4,6-trialdehyde (700 mg, 1.30 mmol) was added and the reaction mixture was stirred for 16 h. Water (200 ml) was then added and the pH was adjusted to 1 with 2 M aqueous HCl. The slurry was extracted with dichloromethane (2×200 ml) and the combined organic phases were washed with water (3×50 ml), dried (MgSO$_4$) and evaporated. Purification by column chromatography (silica gel CH$_2$Cl$_2$-methanol 99:1) gave the pure product as a white solid. Yield: 426 mg (44%).

$^1$H NMR (CDCl$_3$): 7.48 (d, 3H, J 16.2 Hz), 5.95 (d, 3H, J 16.2 Hz), 4.30 (q, 6H, J 7.2 Hz), 1.36 (t, 9H, J 7.2 Hz).

f. 1,3,5-Triiodo-2,4,6-tris(1-hydroxyprop-en-3-yl)benzene 1,3,5-Triiodo-2,4,6-tris(2-prop-1-enoic acid)benzene methyl ester (650 mg, 0.87 mmol) was dissolved in toluene (10 ml) and diisobutylaluminium hydride (5.44 ml of a 1.2 M solution in toluene) was added at 0° C. After stirring for 40 min at 0° C., the solution was poured into methanol (50 ml) and the resulting slurry was stirred for another 45 minutes. The solids were filtered off and the solution was evaporated giving a white solid residue which was purified by trituration with diethyl ether. Yield: 510 mg (94%).

$^1$H NMR (CD$_3$OD): 6.44 (d, 3H, J 16.0 Hz), 5.57 (dt, 3H, J$_d$ 16.0 Hz, J$_t$ 5.8 Hz), 4.23 (m, 6H).

g. 1,3,5-Triiodo-2,4,6-tris(1-acetoxyprop-en-3-yl)benzene 1,3,5-Triiodo-2,4,6-tris(1-hydroxyprop-en-3-yl)benzene (560 mg, 0.90 mmol) was dissolved in a mixture of pyridine (8 ml) and acetic anhydride (8 ml). After stirring at ambient temperature for 16 hours, the solvent was evaporated and the residue was purified by preparative HPLC (RP-18, CH$_3$CN: H$_2$O 80:20). Yield 310 mg (46%).

$^1$H NMR (CDCl$_3$): 6.46 (dt, 3H, J$_d$ 16.2 Hz, J$_t$ 1.6 Hz), 5.68 (dt, 3H, J$_d$ 16.2 Hz, J$_t$ 5.6 Hz), 4.83 (dd, 6H, J$_1$ 5.6 Hz, J$_2$ 1.6 Hz), 2.12 (s, 9H).

$^{13}$CNMR (CDCl$_3$): 170.6, 146.3, 140.9, 131.5, 98.7, 63.5, 20.9.

h. 1,3,5-Triiodo-2,4-di(1,2,3-trihydroxy-1-propyl)-6-(3-hydroxy-1-propen-1-yl)benzene 1,3,5-Triiodo-2,4,6-tris(1-acetoxyprop-en-3-yl)benzene (100 mg, 0.133 mmol) was dissolved in formic acid (5 ml) containing hydrogen peroxide (0.054 ml). The mixture was stirred at ambient temperature for 21 hours and the solvent was evaporated. Methanol (5 ml) was added followed by solid K$_2$CO$_3$ (195 mg), and, after stirring for 1 hour, the solvent was evaporated. The product was purified by preparative HPLC (CH$_3$CN: H$_2$O 3:97).

$^1$H NMR (D$_2$O): 6.45 (d, 1H, J 16.0 Hz), 5.40–5.55 (m, 1H), 4.54–4.90 (m, 11H), 4.23–4.31 (m, 2H), 3.62–3.91 (m, 4H).

MS (ESP): 692 (M$^+$).

EXAMPLE 2

1,3,5-Triiodo-2,4,6-tri(1,2,3-trihydroxy-1-propyl)benzene 1,3,5-Triiodo-2,4,6-tris(1-acetoxyprop-en-3-yl)benzene (100 mg, 0.133 mmol, from Example 1 g) was dissolved in formic acid (5 ml) containing hydrogen peroxide (0.081 ml). The mixture was stirred at room temperature for 40 hours and the solvent was evaporated. Methanol (5 ml) was added followed by solid K$_2$CO$_3$ (195 mg), an, after stirring for 1 h, the solvent was evaporated. The product was purified by preparative HPLC (CH$_3$CN:H$_2$O 3:97).

$^1$H NMR (CD$_3$OD): 4.57–4.94 (m, 15 H), 3.62–3.99 (m, 6H).

MS (ESP): 744 (M+18).

EXAMPLE 3

N-Acetyl-3-hydroxymethyl-5-(2,3-dihydroxypropylaminocarbonyl)-N-(2,3-dihydroxypropyl)-2,4,6-triiodoaniline a. 1-Hydroxymethyl-3-nitro-5-benzoic acid methyl ester 1-Nitroisophthalic acid monomethyl ester (22.5 g, 100 mmol) was dissolved in dry THF (675 ml) and BF$_3$•Et$_2$O (25.2 ml, 200 mmol) was added. NaBH$_4$ (5.1 g, 135 mmol) was then added portionwise during 1 h. After stirring for 2 additional h, ethanol (20 ml) was added slowly followed by water (200 ml) and diethyl ether (400 ml). The phases were separated and the aqueous phase was extracted once with diethyl ether (100 ml). The combined organic phases were washed with a saturated aqueous solution of NaHCO$_3$, dried (Na$_2$SO$_4$) and evaporated. Yield: 20 g (96%). HPLC analysis indicated >95% purity of the product.

$^1$H NMR (CDCl$_3$): 8.72 (s, 1H), 8.42 (s, 1H), 8.32 (s, 1H), 4.86 (s, 2H), 3.97 (s, 3H), 2.37 (br s, 1H).

b. 1-Hydroxymethyl-3-nitro-5-(2,3-dihydroxypropylaminocarbonyl)benzene

The methyl ester from Example 3a (20.5 g, 97 mmol) was mixed with 2,3-dihydroxypropylamine (9.6 g, 106 mmol) and the mixture was heated to 90° C. After 45 min, the pressure was reduced to 200 mm Hg and heating was continued for 2 h. The crude product, which was >95% pure according to HPLC analysis, was used without further purification in the next step. Yield: 22.8 g(87%).

$^1$H NMR (CD$_3$OD): 8.57 (s, 1H), 8.38 (s, 1H), 8.19 (s, 1H), 4.77 (s, 2H), 3.81–3.88 (m, 1H), 3.39–3.63 (m, 4H).

c. 3-Hydroxymethyl-5-(2,3-dihydroxypropylaminocarbonyl)aniline

1-Hydroxymethyl-3-nitro-5-(2,3-dihydroxypropylaminocarbonyl)benzene (12.0 g, 44.4 mmol) was hydrogenated in methanol (150 ml) at 60 psi H$_2$ using Pd/C (10%, 100 mg) as the catalyst. The catalyst was removed by filtration and the residue was evaporated. Addition of methanol (10 ml) precipitated the product as a white solid which was filtered off and dried. Yield: 6.6 g (62%).

$^1$H NMR (CD$_3$OD): 7.05–7.09 (m, 1H), 6.98–7.03 (m, 1H) 6.83–6.87 (m, 1H), 4.53 (s, 2H), 3.77–3.85 (m, 1H), 3.8–3,59 (m, 4H), 3.32–3.42 (m, 1H)

MS (ESP, m/e): 241 ([M+1]$^+$, 100%).

d. 3-Hydroxymethyl-5-(2,3-dihydroxypropylaminocarbonyl)-2,4,6-triiodoaniline

3-Hydroxymethyl-5-(2,3-dihydroxypropylaminocarbonyl)-aniline (500 mg, 2.1 mmol) was dissolved in water (175 ml) and an aqueous solution of KICl$_2$ (70%, w/w) was added in portions of 0.1 ml during 8 h. A total amount of 1.0 ml KICl$_2$ solution was added. After a total reaction time of 6 h, the solution was extracted with ethyl acetate (1000 ml) which was separated and washed with an aqueous solution of Na$_2$S$_2$O$_3$ (0.2M, 100 ml). Evaporation followed by purification by preparative HPLC gave 432 mg (33%) of the pure product.

$^1$H NMR (CD$_3$OD): 5.10 (s, 2H), 3.90–3.98 (m, 1H), 3.72 (ddd, J$_1$=0.7 Hz, J$_2$=4.2 Hz, J$_3$=11.4 Hz), 1H), 3.60 (dd, J$_1$=6.0 Hz, J$_2$=11.4 Hz, 1H), 3.49 (ddd, J$_1$=1.2 Hz, J$_2$=6.0 Hz, J$_3$=13.5 Hz, 1H), 3.37 (ddd, J$_1$=1.2 Hz, J$_2$=6.1 Hz, J$_3$=13.2 Hz, 1H), 2.62 (s, 1H), 2.28 and 2.34 (2s, 2H).

MS (ESP, m/e): 618 (M$^+$, 100%), 640 ([M+Na]$^+$, 55%).

e. N-acetyl-3-acetoxymethyl-5-(2,3-diacetoxypropylaminocarbonyl)-2,4,6-triiodoaniline 3-Hydroxymethyl-5-(2,3-dihydroxypropylaminocarbonyl)-2,4,6-triiodoaniline (3.3 g, 5.3 mmol) was suspended in glacial acetic acid (12 ml) containing acetic anhydride (48 ml) and concentrated sulfuric acid (0.08 ml). The mixture was stirred at 60° C. for 3 h, allowed to cool to room temperature, and CH$_2$Cl$_2$ (100 ml) and water (100 ml) were added. The organic phase was washed with water (3×50 ml) and a saturated aqueous solution of NaHCO$_3$ (2×50 ml). After drying (MgSO$_4$) and evaporation, the residue was dissolved in a mixture of CH$_2$Cl$_2$ and methanol (9:1) and filtered through a short silica pad and evaporated. Yield: 3.0 g (71%).

$^1$H NMR (CDCl$_3$): 8.27–8.32 (m, 1H), 5.51 (s, 2H), 5.18–5.22 (m, 1H), 4.17–4.42 (m, 2H), 3.67–3.84 (m, 1H), 3.41–3.60 (m, 1H), 2.56 (s, 3H), 2.04–2.14 (8s, 12H).

MS (ESP, m/e): 786 (M$^+$, 100%), 809 ([M+Na]$^+$, 81%).

f. N-Acetyl-3-hydroxymethyl-5-(2,3-dihydroxypropylaminocarbonyl)-N-(2,3-dihydroxypropyl)-2,4,6-triiodoaniline N-acetyl-3-acetoxymethyl-5-(2,3-diacetoxypropylaminocarbonyl)-2,4,6-triiodoaniline (1.0 g, 1.27 mmol) was suspended in a mixture of methanol (6 ml) and water (30 ml) and pH was adjusted to 12.0 using a 2 M aqueous solution of NaOH. After stirring for 1 h, 1-bromo-2,3-propanediol (0.99 g, 6.4 mmol) was added and the pH was adjusted to 11.6 using a 2 M aqueous solution of HCl. 1-Bromo-2,3-propanediol (0.99 g, 6.4 mmol) was again added after 16 and 18 h and after 24 h, pH was adjusted to 6.5 using a 2 M aqueous solution of HCl. After evaporation, the residue was purified by preparative HPLC. Yield: 0.373 g (40%).

$^1$H NMR (D$_2$O): 5.20 (s, 2H), 3.23–3.99 (m, 12H), 1.79 (2s, 3H).

MS (ESP, m/e): 734 (M$^+$, 60%), 756 ([M+Na]$^+$, 100%).

EXAMPLE 4

N,N'-bis(hydroxyacetyl)-3,5-diamino-2,4,6-triiodobenzylalcohol a. 3,5-Diaminobenzylalcohol A solution of 3,5-dinitrobenzylalcohol (2.20 g, 11.1 mmol) in methanol (90 ml) and a Pd/C catalyst (10%, 100 mg) was hydrogenated in a Parr apparatus at 60 psi. The solution was filtered and the solvent was removed by evaporation. The crude product was used without purification in the next step.

$^1$H NMR (CDCl$_3$): 6.12–6.14 (m, 2H), 5.96–5.98 (m, 1H), 4.51 (s, 2H), 3.60 (br s, 4H).

b. 3,5-Diamino-2,4,6-triiodobenzylalcohol

The crude product from the previous example dissolved in a mixture of methanol (310 ml) and water (60 ml) and pH was adjusted to 1.5 using a 4 M aqueous solution of HCl. A solution of KICl$_2$ (70%, 11.2 g) was added dropwise at such a rate, that the color disappeared between each addition. After stirring for 5 additional min, the precipitate was filtered off and washed with water (3×50 ml), ether (3×50 ml) and dried. Yield: 4.50 g (80%).

$^1$H NMR (DMSO-d$_6$): 5.20 (s, 4H), 4.81–4.94 (m, 3H).

c. 3,5-Diamino-2,4,6-triiodobenzylacetate 3,5-Diamino-2,4,6-triiodobenzylalcohol (4.42 g, 8.56 mmol) was dissolved in a mixture of pyridine (50 ml) and acetic anhydride (2.5 ml) and the mixture was stirred at room temperature for 16 h. The solvents were evaporated and the residue was washed with ether (3×50 ml), water (3×50 ml) and dried. Yield: 4.52 g (95%).

$^1$H NMR (DMSO-d$_6$): 5.35 (s, 2H), 5.28 (s, 4H), 2.04 (s, 3H).

$^{13}$C NMR (DMSO-d$_6$): 170.5, 148.1, 139.0, 78.0, 73.6, 70.0, 20.8.

d. 3,5-Bis(acetoxyacetylamino)-2,4,6-triiodobenzylacetate 3,5-Diamino-2,4,6-triiodobenzylacetate (5.58 g, 10 mmol) was mixed with acetoxyacetyl chloride (3.22 ml, 30 mmol) and dimethylacetamide (50 ml) and the mixture was stirred for 17 h. Ether (600 ml) was added, and after 20 min, the precipitate was collected, washed with water (3×50 ml) and dried. Recrystallization from acetonitrile gave 3.3 g (44%) of the pure product.

$^1$H NMR (DMSO-d$_6$): 10.27 and 10.19 (2s, 2:1, 2H), 5.51 (s, 2H), 4,66 (s, 4H), 2.13 (s, 3H), 2.12 (s, 3H), 2.06 (s, 3H).

e. N,N'-bis(hydroxyacetyl)-3,5-diamino-2,4,6-triiodobenzylalcohol 3,5-Bis(acetoxyacetylamino)-2,4,6-triiodobenzylacetate (152 mg, 0.2 mmol) was dissolved in a mixture of methanol (6 ml) and 1 M aqueous NaOH (2 ml) and the solution was stirred for 2 h at room temperature. After neutralization with 1 M HCl, the solvents were removed by evaporation and the product was purified by preparative HPLC. Yield: 105 mg (83%).

MS (ESP, m/e): 655 ([M+Na]$^+$, 100%).

EXAMPLE 5

N,N'-Bis(hydroxyacetyl)-N-(2-hydroxyethyl)-3,5-diamino-2,4,6-triiodobenzylalcohol a. N,N'-Bis(acetoxyacetyl)-N-(2-acetoxyethyl)-3,5-diamino-2,4,6-triiodobenzylacetate 3,5-Bis(acetoxyacetylamino)-2,4,6-triiodobenzylacetate (2.15 g, 2.84 mmol) was dissolved in a mixture of DMSO (5 ml) and dimethylacetamide (5 ml) containing $Cs_2CO_3$ (1.0 g, 3.07 mmol) and 2-bromoethyl acetate (0.31 ml, 2.84 ml). The mixture was stirred at room temperature for 48 h, ether (100 ml) and aqueous $NaH_2PO_4$ buffer were added and the organic phase was washed with water and dried. Purification by preparative HPLC gave 520 mg (22%) of the product.

$^1$H NMR (CDCl$_3$): 7.86 (s, 1H), 5.66 (s, 2H), 4.80 (s, 2H), 3.81–4.44 (m, 6H), 2.13–2.27 (m, 12H).

MS (ESP, m/e): 845 ([M+1]$^+$, 100%), 866 ([M+Na]$^+$, 24%).

b. N,N'-Bis(hydroxyacetyl)-N-(2-hydroxyethyl)-3,5-diamino-2,4,6-triiodobenzylalcohol N,N'-Bis(acetoxyacetyl)-N-(2-acetoxyethyl)-3,5-diamino- 2,4,6-triiodobenzylacetate (0.50 g, 0.59 mmol) was dissolved in a mixture of methanol (5 ml), water (5 ml) and aqueous 1 M NaOH (1 ml). The solution was stirred for 2 h, pH was adjusted to 2 using aqueous HCl and the product was purified by preparative HPLC. Yield: 240 mg (67%).

$^1$H NMR DMSO-d$_6$): 9.85 (br s, 1H), 5.77 (br s, 1H), 4.79–5.26 (m, 3H), 3.20–3.71 (m, 6H).

MS (ESP, m/e): 676 (M$^+$, 57%), 698 ([M+Na]$^+$, 100%).

EXAMPLE 6

N,N'-Bis(hydroxyacetyl)-N,N'-bis(2-hydroxyethyl)-3,5-diamino-2,4,6-triiodobenzylalcohol

3,5-Bis(acetoxyacetylamino)-2,4,6-triiodobenzylacetate (190 mg, 0.25 mmol), prepared according to Example 4, was dissolved in dimethylacetamide (5 ml) under an argon atmosphere. 2-Bromoethyl acetate (0.22 ml, 2.0 mmol) and $K_2CO_3$ (138 mg, 1.0 mmol) were added. After 16 h, DMSO (1.5 ml), 2-bromoethyl acetate (0.22 ml, 2.0 mmol) and $K_2CO_3$ (138 mg, 1.0 mmol) were added and the suspension was stirred for another 24 h. Aqueous $NaH_2PO_4$ was added and the resulting solution was extracted with ether (3×25 ml). The combined organic phases were washed with water (4×20 ml) and then dried (MgSO$_4$). The solvent was removed by evaporation and the residue, a colorless oil, was dissolved in a mixture of methanol (3 ml) an 1 M aqueous NaOH (3 ml). The solution was stirred for 1 h, pH was adjusted to 6 using aqueous HCl and the solvents were removed by evaporation. Purification by preparative HPLC gave 60 mg (33%) of the product.

MS (ESP, m/e): 720 (M$^+$, 100%), 742 ([M+Na]$^+$, 36%).

EXAMPLE 7

N,N'-Bis(hydroxyacetyl)-N-(2,3-dihydroxypropyl)-3,5-diamino-2,4,6-triiodobenzylalcohol a. N,N'-Bis(acetoxyacetyl)-N-[(2,2-dimethyl-1,3-dioxolane-4-yl)-methyl]-3,5-diamino-2,4,6-triiodobenzylacetate 3,5-Bis(acetoxyacetylamino)-2,4,6-triiodobenzylacetate (90 mg, 0.12 mmol), prepared according to Example 4, was dissolved in a mixture of dimethylacetamide (3 ml) and DMSO (3 ml). 4-Bromomethyl-2,2-dimethyl-1,3-dioxolane (0.097 g, 0.5 mmol) and $Cs_2CO_3$ (0.10 g, 0.3 mmol) were added and the solution was stirred at room temperature for 48 h. Aqueous $NaH_2PO_4$ was added and the solution was extracted with ether (3×25 ml). The combined organic phases were washed with water (3×15 ml), dried (MgSO$_4$) and evaporated. Purification by preparative HPLC gave 36 mg (35%) of the pure product.

$^1$H NMR (DMSO-d$_6$): 10.30 (br s, 1H), 5.53 (s, 2H), 3.61–4.68 (m, 9H), 2.13 (s, 3H), 2.07 (s, 3H), 2.06 (s, 3H), 1.17–1.34 (m, 6H).

MS (ESP, m/e): 894 ([M+Na]$^+$, 100%), 910 ([M+K]$^+$, 11%).

b. N,N'-Bis(hydroxyacetyl)-N-(2,3-dihydroxypropyl)-3,5-diamino-2,4,6-triiodobenzylalcohol N,N'-Bis(acetoxyacetyl)-N-[(2,2-dimethyl-1,3-dioxolane-4-yl)-methyl]-3,5-diamino-2,4,6-triiodobenzylacetate (36 mg, 0.042 mmol) was dissolved in a mixture of methanol (3 ml) and water (4 ml) and the pH was adjusted to 12 using a 1 M aqueous solution of NaOH. After stirring for 2 h, pH was adjusted to 1 using 1 M aqueous HCl and stirring was continued for 16 h. The solution was neutralized with an aqueous $NaH_2PO_4$ buffer, the solvents were removed by evaporation and the residue was purified by preparative HPLC to give 24 mg (81%) of the pure product.

MS (ESP, m/e): 704 (M$^+$, 100%), 726 ([M+Na]$^+$, 34%).

EXAMPLE 8

N,N'-Bis(2-hydroxypropionyl)-3,5-diamino-2,4,6-triiodobenzylalcohol a. N,N'-Bis(2-acetoxypropionyl)-3,5-diamino-2,4,6-triiodobenzylacetate 3,5-Diamino-2,4,6-triiodobenzylacetate (2.79 g, 5.0 mmol) was dissolved in dimethylacetamide (25 ml) and cooled to 0° C. 2-Acetoxypropionyl chloride (3.73 g, 25 mmol) was added dropwise and the mixture was stirred at room temperature for 17 h. The solvents were evaporated and the residue was triturated with diethyl ether. The solid residue was then purified by flash chromatography on silica gel using a mixture of $CH_2Cl_2$ and acetonitrile (5:1) as the eluent. Yield: 2.21 g (56%).

$^1$H NMR (DMSO-d$_6$): 10.20–10.23 (m, 2H), 5.52 (s, 2H), 5.21–5.24 (m, 2H), 2.06–2.13 (m, 9H), 1.51 (d, J=6.9 Hz, 6H).

b. N,N'-Bis(2-hydroxypropionyl)-3,5-diamino-2,4,6-triiodobenzylalcohol

N,N'-Bis(2-acetoxypropionyl)-3,5-diamino-2,4,6-triiodobenzylacetate (0.16 g, 0.2 mmol) was dissolved in a mixture of methanol (5 ml) and water (5 ml) and the pH was adjusted to 12 using a 1 M aqueous solution of NaOH. After stirring for 15 h, the solution was neutralized with 1 M HCl and the solvents were removed by evaporation. Purification by preparative HPLC gave 61 mg (46%) of the pure product.

MS (ESP, m/e): 660 (M$^+$, 5%), 682 ([M+Na]$^+$, 100%), 698 ([M+K]$^+$, 17%).

EXAMPLE 9

N,N'-Bis(2-hydroxypropionyl)-N-(2-hydroxyethyl)-3,5-diamino-2,4,6-triiodobenzylalcohol a. N,N'-Bis(2-acetoxypropionyl)-N-(2-acetoxyethyl)-3,5-diamino-2,4,6-triiodobenzylacetate N,N'-Bis(2-acetoxypropionyl)-3,5-diamino-2,4,6-triiodobenzylacetate (393 mg, 0.50 mmol) was dissolved in a mixture of dimethylacetamide (4 ml) and DMSO (4 ml)

containing 2-bromoethyl acetate (0.083 g, 0.50 mmol) and Cs$_2$CO$_3$ (244 mg, 0.75 mmol). The mixture was stirred for 17 h, water (20 ml) was added and the mixture was extracted with ether (3×25 ml). The combined organic phases were washed with water (3×20 ml), dried (MgSO$_4$) and evaporated. The residue was purified by preparative HPLC to give 80 mg (18%) of pure product.

$^1$H NMR (CD$_3$OD): 5.72–5.82 (m, 2H), 5.20–5.42 (m, 2H), 3.55–4.48 (m, 4H), 1.90–2.24 (m, 12H), 1.66 (d, J=7.1 Hz, 6H).

MS (ESP, m/e): 1004 ([M+Cs]$^+$, 100%).

b. N,N'-Bis(2-hydroxypropionyl)-N-(2-hydroxyethyl)-3,5-diamino-2,4,6-triiodobenzylalcohol N,N'-Bis(2-acetoxypropionyl)-N-(2-acetoxyethyl)-3,5-diamino-2,4,6-triiodobenzylacetate (120 mg, 0.14 mmol) was dissolved in a mixture of water (7 ml) and methanol (7 ml) and pH was adjusted to 12 using an 1 M aqueous solution of NaOH. The mixture was stirred for 2 h, pH was adjusted to 7 with aqueous HCl and the solvents were evaporated. The product was purified by preparative HPLC. Yield: 70 mg (72%).

$^1$H NMR (CD$_3$OD): 5.27–5.34 (m, 2H), 4.31–4.41 (m, 1H), 3.82–4.12 (m, 4H), 3.55–3.73 (m, 1H), 1.51–1.60 (m, 3H), 1.23–1.32 (m, 3H).

MS (ESP, m/e): 726 ([M+Na]$^+$, 100%).

EXAMPLE 10

N,N'-Bis(2-hydroxypropionyl)-N,N'-bis(2-hydroxyethyl)-3,5-diamino-2,4,6-triiodobenzylalcohol a. N,N'-Bis(2-acetoxypropionyl)-N,N'-bis(2-acetoxyethyl)-3,5-diamino-2,4,6-triiodobenzylacetate N,N'-Bis(2-acetoxypropionyl)-3,5-diamino-2,4,6-triiodobenzylacetate (197 mg, 0.25 mmol) was dissolved in a mixture of dimethylacetamide (5 ml) and DMSO (1.5 ml) containing 2-bromoethyl acetate (0.11 ml, 1.0 mmol) and Cs$_2$CO$_3$ (162 mg, 0.50 mmol). The mixture was stirred for 67 h, water (20 ml) was added and the mixture was extracted with ether (2×75 ml). The combined organic phases were washed with water (5×75 ml), dried (Na$_2$SO$_4$) and evaporated. The residue was purified by preparative HPLC to give 35 mg (15%) of pure product.

$^1$H NMR (DMSO-d$_6$) 5.49–5.73 (m, 2H), 4.97–5.22 (m, 2H), 3.49–4.00 (m, 6H), 1.86–12.08 (m, 15H), 1.09–1.58 (m, 6H).

b. N,N'-Bis(2-hydroxypropionyl)-N,N'-bis(2-hydroxyethyl)-3,5-diamino-2,4,6-triiodobenzylalcohol N,N'-Bis(2-acetoxypropionyl)-N,N'-bis(2-acetoxyethyl)-3,5-diamino-2,4,6-triiodobenzylacetate (175 mg, 0.18 mmol) was dissolved in a mixture of methanol (8 ml) and water (8 ml) and pH was adjusted to 12 with 1 M aqueous NaOH. After stirring for 3 h, the solution was neutralized with aqueous HCl. Purification by preparative HPLC gave 50 mg (37%) of the pure product.

$^1$H NMR (CD$_3$OD): 5.26–5.38 (m, 2H), 3.44–4.08 (m, 6H), 1.32–1.59 (m, 6H).

MS (ESP, m/e): 770 ([M+Na]$^+$, 100%).

EXAMPLE 11

N,N'-Bis(2-hydroxypropionyl)-N-(2,3-dihydroxyoropyl)-3,5-diamino-2,4,6-triiodobenzylalcohol a. N,N'-Bis(acetoxyoropionyl)-N-[(2,2-dimethyl-1,3-dioxolane-4-yl)-methyl]-3,5-diamino-2,4,6-triiodobenzylacetate N,N'-Bis(2-acetoxypropionyl)-3,5-diamino-2,4,6-triiodobenzylacetate (393 mg, 0.50 mmol) was dissolved in a mixture of DMSO (4 ml) and dimethylacetamide (4 ml) containing Cs$_2$CO$_3$ (1.80 g, 5.52 mmol) and 4-bromomethyl-2,2-dimethyl-1,3-dioxolane (1.0 ml). The mixture was stirred for 7 days and was then worked up analogous to Example 7a. Purification by preparative HPLC gave 115 mg (26%) of the pure product.

$^1$H NMR (CD$_3$OD) 5.61–5.5.75 (m, 2H), 5.03–5.44 (m, 2H), 3.47–4.55 (m, 6H), 1.98–2.23 (m, 9H), 1.30–1.71 (m, 12H).

MS (ESP, m/e): 922 ([M+Na]$^+$, 100%).

b. N,N'-Bis(2-hydroxypropionyl)-N-(2,3-dihydroxypropyl)-3,5-diamino-2,4,6-triiodobenzylalcohol N,N'-Bis(acetoxypropionyl)-N-[(2,2-dimethyl-1,3-dioxolane-4-yl)-methyl]-3,5-diamino-2,4,6-triiodobenzylacetate (115 mg, 0.13 mmol) was dissolved in a mixture of methanol (8 ml) and water (8 ml) and pH was adjusted to 12 with aqueous 1 M NaOH. After 2.5 h, pH was adjusted to 1 with 2 M aqueous HCl. After stirring for 17 h, the solution was neutralized with an aqueous NaH$_2$PO$_4$ buffer and the solvents were removed evaporation. Purification by preparative HPLC gave 65 mg (69%) of the pure product.

MS (ESP, m/e): 756 ([M+Na]$^+$, 100%).

EXAMPLE 12

N,N'-Bis(2,3-dihydroxypropionyl)-3,5-diamino-2,4,6-trijodobenzylalcohol a. N,N'-Bis(2,2-dimethyl-1,3-dioxolane-4-carbonyl)-3,5-diamino-2,4,6-triiodobenzylacetate 3,5-Diamino-2,4,6-triiodobenzylacetate (3.54 g, 6.3 mmol) and 2,2-dimethyl-1,3-dioxolane-4-carboxylic acid chloride (3.13 g, 19 mmol) were dissolved in dimethylacetamide (40 ml) and the solution was stirred for 3.5 h. The solvent was removed by evaporation and the residue was treated with an aqueous solution of NaHCO$_3$. The crystalline residue was filtered off, washed with water and dried. Purification by flash chromatography using a mixture of CH$_2$Cl$_2$ and CH$_3$CN (3:1) as the eluent gave 1.90 g (37%) of the pure product.

$^1$H NMR (DMSO-d$_6$): 9.93–10.02 (mn, 2H), 5.30 (s, 2H), 4.58 (t, J=6.2 Hz, 1H), 4.29 (t, J=7.3 Hz, 1H), 4.10 (t, J=6.1 Hz, 1H), 2.06 (s, 3H), 1.54 (s, 3H), 1.38 (s, 3H).

MS (ESP, m/e): 902 ([M+dimethylacetamide]$^+$, 100%).

b. N,N'-Bis(2,3-dihydroxypropionyl)-3,5-diamino-2,4,6-triiodobenzylalcohol

N,N'-Bis(2,2-dimethyl-1,3-dioxolane-4-carbonyl)-3,5-diamino-2,4,6-triiodobenzylacetate (1.25 g, 1.55 mol) was dissolved in a mixture of water (50 ml), methanol (25 ml) and concentrated HCl (0.5 ml). After stirring for 4 h, the solution was neutralized with aqueous NaH$_2$PO$_4$ and the solvents were removed by evaporation. The residue was dissolved in water (10 ml) and the pH was adjusted to 12 with aqueous NaOH. After 30 min, the solution was again neutralized and the solvent was evaporated. The product was purified by preparative HPLC. Yield: 483 mg (45%).

$^1$H NMR (9.65–9.83 (m, 2H), 5.77 (s, 2H), 5.20 (s, 1H), 4.95–5.03 (m, 2H), 4.81 (s, 2H), 4.00–4.08 (m, 2H), 3.72–3.82 (m, 2H), 3.50–3.63 (m, 2H).

MS (ESP, m/e): 692 (M$^+$, 62%), 714 ([M+Na]$^+$, 100%).

EXAMPLE 13

N,N'-Bis(2,3-dihydroxypropionyl)-N-(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol)

was dissolved in a mixture of dimethylacetamide (4 ml) and DMSO (2.5 ml) containing $Cs_2CO_3$ (650 mg, 2.0 mmol) and 2-bromoethyl acetate (0.035 ml, 0.31 mmol). After stirring for 1 week, ether (150 ml) and a $NaH_2PO_4$ buffer (100 ml) were added, the organic phase was separated and the aqueous phase was extracted with ether (150 ml). The combined organic phases were then washed with water (6×100 ml), dried ($Na_2SO_4$) and evaporated. The residue was dissolved in a mixture of methanol (20 ml) and water (20 ml) and pH was adjusted to 12 with aqueous NaOH. After stirring for 1 h, the pH was adjusted to 1.5 with concentrated HCl and stirred for another 16 h. The solution was neutralized with aqueous $NaH_2PO_4$ and the solvents were evaporated. Preparative HPLC gave 55 mg (30%) of the pure product.

MS (ESP, m/e): 736 ($M^+$, 28%), 758 ($[M+Na]^+$, 100%).

EXAMPLE 14

N,N'-Bis(2,3-dihydroxypropionyl)-N,N'-bis(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol) was dissolved in a mixture of dimethylacetamide (5 ml) and DMSO (1.5 ml) containing $K_2CO_3$ (276 mg, 2.0 mmol) and 2-bromoethyl acetate (0.44 ml, 4.0 mmol). After stirring for 48 h, an aqueous $NaH_2PO_4$ buffer was added and the mixture was extracted with ether (2×150 ml). The combined organic phases were washed with water (6×100 ml), dried ($Na_2SO_4$) and evaporated. The solid residue was dissolved in a mixture of methanol (12 ml) and water (12 ml) and the pH was adjusted to 12 with aqueous NaOH. After stirring for 18 h, the solution was acidified with concentrated HCl (0.70 ml) and stirring was continued for 3 h. The solution was neutralized and the solvents were removed by evaporation. The product was purified by preparative HPLC. Yield: 98 mg (50%).

MS (ESP, m/e): 802 ($[M+Na]^+$n 100%).

EXAMPLE 15

N,N'-Bis(2,3-dihydroxypropionyl)-N-(2,3-dihydroxypropyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (408 mg, 0.50 mmol) was dissolved in a mixture of dimethylacetamide (4 ml) and DMSO (4 ml) containing $Cs_2CO_3$ (1.80 g, 5.52 mmol) and 2,2-dimethyl-1,3-dioxolane-4-carboxylic acid chloride (2.0 ml). After stirring for 8 days, aqueous $NaH_2PO_4$ (100 ml) was added and the mixture was extracted with diethyl ether (2×150 ml). The combined organic phases were washed with water (6×100 ml), dried ($Na_2SO_4$) and evaporated. The residue was dissolved in a mixture of methanol (10 ml) and water (10 ml) and pH was adjusted to 12 with aqueous NaOH. After stirring for 2 h, concentrated HCl (1.0 ml) was added and stirring was continued for 16 h. After neutralization, the solvents were evaporated and the residue was purified by preparative HPLC. Yield: 149 mg (39%).

MS (ESP, m/e): 766 ($M^+$, 60%), 788 ($[M+Na]^+$, 100%).

EXAMPLE 16

Oxalic bis[3-hydroxymethyl-5-(2,3-dihydroxypropylaminocarbonyl)-2,4,6-triiodobenzeneamide]

a. 3-Acetoxymethyl-5-(2,3-diacetoxypropylaminocarbonyl)-2,4,6-triiodoaniline

3-Hydroxymethyl-5-(2,3-dihydroxypropylaminocarbonyl)-2,4,6-triiodoaniline (1.89 g, 3.06 mmol) prepared according to Example 3d, was dissolved in a mixture of acetic anhydride (5 ml) and pyridine (5 ml). The mixture was stirred at room temperature for 24 h, $CH_2Cl_2$ (100 ml) was added and the solution was washed with water (3×25 ml), with a saturated aqueous solution of $NaHCO_3$, dried ($Na_2SO_4$) and evaporated. The product was purified by flash chromatography on silica gel using a mixture of $CH_2Cl_2$ and methanol (98:2) as the eluent. Yield: 1.30 g (57%).

$^1$H NMR ($CDCl_3$): 6.10–6.25 (m, 1H), 5.48 (s, 2H), 5.20–5.28 (m, 1H), 4.22–4.43 (m, 2H), 3.53–3.89 (m, 2H), 2.06–2.13 (m, 9H).

MS (ESP, m/e): 744 ($M^+$, 100%).

b. Oxalic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) was dissolved in dioxane (1.0 ml) and the solution was heated to 90° C. Oxalyl chloride (0.096 mmol) was added and the mixture was stirred at 78° C. for 17 h. After cooling to room temperature, water (1.0 ml) was added and pH was adjusted to 12 with aqueous NaOH. After stirring for 4 h, the solution was neutralized, the solvents were evaporated and the residue was purified by preparative HPLC. Yield: 14 mg (16%).

$^1$H NMR ($CD_3OD$): 5.24 (s, 2H), 3.38–4.03 (m, 10H).

MS (ESP. m/e): 1290 ($M^+$, 33%), 1312 ($[M+Na]^+$, 100%).

EXAMPLE 17

Malonic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) prepared according to Example 16a, was dissolved in dioxane (1.0 ml) and malonyl chloride (0.097 mmol) was added. The mixture was stirred at 90° C. for 2 h and the solution was allowed to cool to room temperature. Water (1 ml) was added and pH was adjusted to 12 with aqueous NaOH. After stirring at 60° C. for 18 h, the solution was neutralized and the solvents were evaporated. The product was purified by preparative HPLC. Yield: 34 mg (39%).

MS (ESP, m/e): 1304 ($M^+$, 68%), 1326 ($[M+Na]^+$, 100%).

EXAMPLE 18

N,N'-diacetyl-N,N'-bis[3-hydroxymethyl-5-(2,3-dihydroxypropylaminocarbonyl)-2,4,6-triiodophenyl]-1,3-diamino-2-hydroxypropane N-acetyl-3-acetoxymethyl-5-(2,3-acetoxypropylaminocarbonyl)-2,4,6-triiodoaniline (300 mg, 0.38 mmol) prepared according to Example 3e was dissolved in a mixture of water (1.2 ml) and methanol (0.2 ml) and pH was adjusted to 12 with aqueous NaOH. Epichorohydrine (0.28 mmol) was added and the mixture was stirred at room temperature for 65 h. The solution was neutralized and the product was isolated by preparative HPLC. Yield: 60 mg (20%).

MS (ESP, m/e): 1398 ($[M+Na]^+$, 100%).

EXAMPLE 19

N-[3-hydroxymethyl-5-(2,3-dihydroxypropylaminocarbonyl)-2,4,6-triiodophenyl]-N'[3,5-bis(2,3-dihydroxypropylaminocarbonyl)-2,4,6-triiodophenyl]urea a. N-[3-acetoxymethyl-5-(2,3-diacetoxypropylaminocarbonyl)-2,4,6-triiodophenyl]-N'[3, 5-bis(2,3-dihacetoxypropylaminocarbonyl)-2,4,6-triiodophenyl]urea 3,5-Bis(2,3-diacetoxypropylaminocarbonyl)-2,4,6-triiodoaniline (260 mg, 0.30 mmol) was dissolved in dioxane (1.0 ml) and a solution of phosgene in toluene (1.93 M,1.8 ml) was added. The flask was tightly sealed and then heated to 60° C. for 17 h. After cooling to room temperature, the solvent was distilled off at reduced pressure. Dioxane (3 ml) was added and distilled off again. This procedure was repeated twice. Dioxane (1 ml) was added followed by 3-acetoxymethyl-5-(2,3-diacetoxypropylaminocarbonyl)-2,4,6-triiodoaniline (0.245 g, 0.31 mmol), prepared according to Example 16a, and $Hg(OCOCF_3)_2$ (20 mg). The mixture was stirred for 16 h at room temperature, the solvent was evaporated and the residue was purified by preparative HPLC. Yield: 0.192 g (39%).

MS (ESP, m/e): 1643 ($M^+$, 100%), 1665 ($[M+Na]^+$, 34%).

b. N-[3-hydroxymethyl-5-(2,3-dihydroxypropylaminocarbonyl)-2,4,6-triiodophenyl]-N'[3,5-bis(2,3-dihydroxypropylaminocarbonyl)-2,4,6-triiodophenyl]urea The product from Example 19a was dissolved in a mixture of methanol (5 ml) and water (5 ml) and the pH was adjusted to 12 using a 2 M aqueous solution of NaOH. After stirring for 2 h, the pH was adjusted to 6.5 using aqueous HCl and the solvents were evaporated. The product was purified using preparative HPLC. Yield: 68 mg (44%).

MS (ESP, m/e): 1349 ($M^+$, 15%), 1372 ($[M+Na]^+$, 100%).

EXAMPLE 20

N-Hydroxyacetyl-3-(1,2-dihydroxyethyl)-5-(2,3-dihydroxypropylaminocarbonyl)-2,4,6-triiodoaniline a. 3-Nitro-5-(2-trimethylsilylvinyl)benzoic acid methyl ester A mixture of 3-iodo-5-nitrobenzoic acid methyl ester (307 mg, 1.0 mmol), $Pd(OAc)_2$ (67 mg, 0.30 mmol), triphenylphosphine (0.032 g, 0.60 mmol), $AgNO_3$ (170 mg, 1.0 mmol), triethylamine (0.167 ml, 1.2 mmol) and vinyltrimethylsilane (0.309 ml, 2.0 mmol) was dissolved in acetonitrile (10 ml) and the solution was heated to 60° C. in a closed vessel for 48 h. The precipitated salts were filtered off and the filtrate was evaporated. The residue was chromatographed on silica gel using a mixture of ethyl acetate and heptane (1:11) as the eluent. Yield: 210 mg (75%).

$^1$H NMR ($CDCl_3$): 8.70–8.73 (m, 1H), 8.36–8.47 (m, 2H), 6.93 (d, J=19.2 Hz, 1H), 6.75 (d, J=19.2 Hz, 1H), 3.99 (s, 3H), 0.20 (s, 9H).

MS (APci, m/e): 279 ($M^+$, 100%).

b. 3-Nitro-5-vinylbenzoic acid methyl ester

3-Nitro-5-(2-trimethylsilylvinyl)benzoic acid methyl ester (2.44 g, 8.71 mmol) was dissolved in acetonitrile (150 ml), the solution was heated to reflux temperature and HCl gas was bubbled through the solution until the starting material had disappeared according to HPLC analysis. The solution was allowed to cool and the solvent was removed by evaporation. The residue was >95% pure according to HPLC and was used without further purification. Yield: 2.02 g (89%).

$^1$H NMR ($CD_3CN$): 8.64 (s, 1H), 8.54 (s, 1H) , 8.45 (s, 1H), 6.96 (dd, $J_1$=10.8 Hz, $J_2$=17.4 Hz, 1H), 6.11 (d, J=17.4 Hz, 1H), 5.59 (d, J=10.8 Hz, 1H), 4.00 (s, 3H).

c. 3-Nitro-5-(1,2-dihydroxyethyl)benzoic acid methyl ester

3-Nitro-5-vinylbenzoic acid methyl ester (2.02 g, 9.76 mmol) was dissolved in a mixture of acetone and water (200 ml, 9:1), and, after cooling to 0° C., $OsO_4$ (60 mg, 0.24 mmol) was added followed by N-methylmorpholine-N-oxide (2.34 g, 20.0 mmol). After stirring for 46 h at room temperature, an aqueous solution of $Na_2S_2O_5$ (3.7 g) in water (150 ml) was added and the solution was acidified with dilute aqueous HCl. The volume of the solution was reduced to 150 ml by evaporation and the residue was extracted with ethyl acetate (3×100 ml). The combined organic phases were evaporated and the residue was purified by column chromatography on silica gel using ethyl acetate as the eluent. Yield: 1.60 g (60%).

$^1$H NMR ($CD_3CN$): 8.62–8.66 (m, 1H) 8.44–8.48 (m, 1H), 8.36–8.40 (m, 1H), 4.88–4.94 (m, 1H), 3.98 (s, 3H), 3.60–3.79 (m, 4H).

d. 1-(2,3-Dihydroxypropylaminocarbonyl)-3-nitro-5-(1,2-dihydroxyethyl)benzene

3-Nitro-5-(1,2-dihydroxyethyl)benzoic acid methyl ester (0.40 g, 1.69 mmol) and 2,3-dihydroxypropylamine (0.17 g, 1.86 mmol) were dissolved in methanol (2 ml) and the solution was stirred at 75° C. for 1 h. The pressure was then reduced to 200 mm Hg and stirring was continued at 95° C. for 2 h. The crude reaction mixture was purified by preparative HPLC. Yield: 0.40 g (78%).

MS (ESP. m/e): 299 ($[M-1]^+$, 100%).

e. 3-(2,3-Dihydroxypropylaminocarbonyl)-5-(1,2-dihydroxyethyl)aniline 1-(2,3-Dihydroxypropylaminocarbonyl)-3-nitro-5-(1,2-dihydroxyethyl)benzene (0.40 g, 1.32 mmol) was dissolved in a mixture of methanol (40 ml) and water (20 ml). The solution was hydrogenated at 60 psi using a Pd/C catalyst (10%, 50 mg). The solution was filtered through celite and the solvents were removed by evaporation. The product was >95% pure by HPLC analysis and was used without further purification.

MS (ESP, m/e): 271 ($[M+1]^+$, 100%), 293 ($[M+Na]^+$, 45%).

f. 3-(2,3-Dihydroxypropylaminocarbonyl)-5-(1,2-dihydroxyethyl)-2,4,6-triodoaniline 3-(2,3-Dihydroxypropylaminocarbonyl)-5-(1,2-dihydroxyethyl)aniline (0.37 g, 1.35 mmol) was dissolved in a mixture of methanol (30 ml) and water (90 ml). $KICl_2$ (1.37 g, 4.05 mmol) was added and the solution was stirred at 35° C. for 24 h. Additional $KICl_2$ (1.0 mmol) was added, and stirring was continued at 60° C. for 72 h. An aqueous solution of $Na_2S_2O_5$ (1.0 g in 50 ml) was added and the solvents were removed by evaporation. Purification by preparative HPLC gave 87 mg (10%) of the pure product.

$^1$H NMR ($CD_3OD$): 8.60 (m, 1H), 5.38–5.47 (m, 1H), 3.96–4.26 (m, 3H), 3.30–3.84 (m, 10 H).

MS (ESP, m/e): 648 ($M^+$, 15%), 670 ($[M+Na]^+$, 100%).

g. N-Hydroxyacetyl-3-(2,3-dihydroxypropylaminocarbonyl)-5-(1,2-dihydroxyethyl)-2,4,6-triodoaniline 3-(2,3-Dihydroxypropylaminocarbonyl)-5-(1,2-dihydroxyethyl)-2,4,6-triodoaniline (0.059 d, 0.091 mmol) was mixed with acetoxyacetyl chloride (1.0 ml) containing N,N-dimethylacetamide (0.4 ml) and the mixture was stirred at 60° C. for 48 h. The mixture was allowed to cool to room temperature, water was added and the solvents were removed by evaporation. The residue was dissolved in a mixture of methanol (10 ml) and water (5 ml) and an aqueous solution of NaOH (5 M, 1 ml) was added. The solution was stirred at room temperature for 1 h, the solution was neutralized with aqueous HCl and the solvents were evaporated. Purification by HPLC gave the pure product.

MS (ESP, m/e): 706 ($M^+$, 100%).

EXAMPLE 21

3,5-Di(hydroxyacetylamino)-2,4,6-triiodoacetophenone a. 1,3-Diamino-5-(1-hydroxyethyl)benzene 3,5-Dinitroacetophenone (2.02 g, 9.5 mmol) which had been prepared according to the literature procedure (Y. Nagase et al., Macromol. Chem. Rapid Comm. (1990) 11, 185–191) was dissolved in methanol (100 ml) and hydrogenated at 60 psi using a Pd/C catalyst (5%, 100 mg). The catalyst was filtered off and the solvent was removed by evaporation. The product was used without purification in the next step. Yield: 1.22 g (84%).

$^1$H NMR (CDCl$_3$): 6.20 (d, J=2.0 Hz, 2H), 6.08 (t, J=2.0 Hz, 1H), 4.90 (br s, 4H), 4.62 (q, J=7.0 Hz, 1H), 3.37 (d, J=7.0 Hz, 3H).

MS (ESP, m/e): 151 ([M–1]$^+$, 100%).

b. 1,3-Diamino-2,4,6-triiodoacetophenone 1,3-Diamino-5-(1-hydroxyethyl)benzene (1.18 g, 7.72 mmol) was dissolved in a mixture of methanol and water (5:1, 168 ml) containing 1 M aqueous HCl (16 ml). An aqueous solution of KICl$_2$ (7.31 g, 30.9 mmol) was added quickly, and, after stirring for 50 min, the solid was filtered off, washed with water and dried. The product was pure by TLC and $^1$H NMR analysis. Yield: 3.62 g (89%).

$^1$H NMR CDCl$_3$): 4.86 (br s, 4H), 2.62 (s, 3H).

$^{13}$C NMR (CDCl$_3$): 204.7, 151.1, 146.8, 28.7.

MS (APci, m/e): 528 (M$^+$, 100%).

c. 1,3-Di(acetoxyacetylamino)-2,4,6-triiodoacetophenone 1,3-Diamino-2,4,6-triiodoacetophenone (1.8 g, 3.41 mmol) was dissolved in dimethylacetamide (15 ml) containing acetoxyacetyl chloride (1.1 ml, 10.2 mmol) and the solution was stirred for 65 h at room temperature. The solvents were removed by evaporation and the residue was purified by preparative HPLC. Yield: 1.69 g (68%).

$^1$H NMR DMSO-d$_6$): 10.13–10.27 (m, 2H), 4.65 (s, 4H), 2.56 (s, 3H), 2.12 (s, 6H).

MS(ESP, m/e): 750 ([M+Na]$^+$, 100%), 766 ([M+K]$^+$, 26%).

d. 1,3-Di(hydroxyacetylamino)-2,4,6-triiodoacetophenone 1,3-Di(acetoxyacetylamino)-2,4,6-triiodoacetophenone (0.171 g, 0.23 mmol) was dissolved in a mixture of methanol (30 ml) and water (5 ml) containing 2 M aqueous NaOH (3 ml). The solution was stirred for 90 min and was then neutralized using a strongly acidic cation exchange resin. The solvents were removed by evaporation and the residue was purified by preparative HPLC. Yield: 98 mg (54%).

MS (ESP, m/e): 644 (M$^+$, 100%), 666 ([M+Na]$^+$, 95%).

EXAMPLE 22

3,5-Di(hydroxyacetylamino)-1-hydroxyacetyl-2,4,6-triiodobenzene a. 3,5-Di(acetoxyacetylamino)-1-bromoacetyl-2,4,6-triiodobenzene 1,3-Di(acetoxyacetylamino)-2,4,6-triiodoacetophenone (0.20 g, 0.279 mmol) was dissolved in glacial acetic acid and bromine (0.044 g, 0.28 mmol) was added. The reaction was stirred at 2.5 h at 75° C. and then allowed to cool. The solvents were removed by evaporation and the residue was used directly in the next step.

MS (ESP, m/e): 806 (M$^+$, 100%), 808 (M$^+$, 98%).

b. 3,5-Di(acetoxyacetylamino)-1-acetoxyacetyl-2,4,6-triiodobenzene 3,5-Di(acetoxyacetylamino)-1-bromoacetyl- 2,4,6-triiodobenzene (10 mg, 0.12 mmol) was converted into the corresponding acetate by heating to 110° C. in glacial acetic acid (5 ml) containing sodium acetate (1 mmol) and AgO-COCF$_3$ (0.11 g, 0.5 mmol) for 16 h. The product was purified by preparative HPLC. The yield was not determined.

MS (ESP, m/e): 786 (M$^+$, 100%).

c. 3,5-Di(hydroxyacetylamino)-1-hydroxyacetyl-2,4,6-triiodobenzene

Hydrolysis of 3,5-di(acetoxyacetylamino)-1-acetoxyacetyl-2,4,6-triiodobenzene was carried out analogous to Example 4e. The crude product was purified by preparative HPLC. The yield was not determined.

MS (ESP, m/e): 687 ([M+HCOOH]$^+$, 100%).

EXAMPLE 23

3,5-Di(hydroxyacetylamino)-1-(1,2-dihydroxyethyl)-2,4,6-triiodobenzene a. 3,5-Dinitrophenylethanol 3,5-Dinitroacetophenone (3.27 g, 0.0156 mol) was dissolved in a mixture of absolute ethanol (75 ml) and THF (37.5 ml) and the mixture was cooled to –10° C. NaBH$_4$ (0.30 g, 7.9 mmol) was added and the mixture was stirred for 1 h at –10° C. Water (80 ml) and ethyl acetate were added, the phases were separated and the organic phase was washed with water (80 ml) and dried (Na$_2$SO$_4$). The solvents were removed by evaporation and the residue was purified by chromatography on neutral alumina using a mixture of pentane and ethyl acetate (1:1) as the eluent. Yield: 2.52 g (76%).

$^1$H NMR (CDCl$_3$): 8.95 (t, J=2.0 Hz, 1H), 8.60 (d, J=2.0 Hz, 1H), 8.59 (d, J=2.0 Hz, 1H), 5.15 (q, J=7.5 Hz, 1H), 1.61 (d, J=7.5 Hz, 3H).

b. 3,5-Dinitrostyrene 3,5-Dinitrophenylethanol (1.0 g, 4.7 mmol) was mixed with P$_2$O$_5$ (1.0 g, 0.71 mmol) and the stirred mixture was heated to 100° C. After 3 h, the mixture was allowed to cool to room temperature and water (0.4 ml) was added. The pH was adjusted to 9 using 1 M aqueous NaOH and extracted with diethyl ether (2×25 ml). The combined organic phases were dried (Na$_2$SO$_4$) and evaporated. The crude product was used without further purification in the next step.

$^1$H NMR CDCl$_3$): 8.92 (t, J=2.0 Hz, 1H), 8.56 (d, J=2.0 Hz, 2H), 6.86 (dd, J$_1$=18.4 Hz, J$_2$=10.9 Hz, 1H), 6.08 (d, J=18.0 Hz, 1H), 5.67 (d, J=10.9 Hz, 1H).

c. 1-(1,2-Dihydroxyethyl)-3,5-dinitrobenzene 3,5-Dinitrostyrene (0.50 g, 2.58 mmol) was dissolved in a mixture of acetone and water (8:1, 70 ml) and the solution was cooled to 0° C. OsO$_4$ (0.046 g, 0.18 mmol) and NMO (0.60 g, 5.15 mmol) were added and the solution was stirred at room temperature for 16 h. A solution of Na$_2$S$_2$O$_5$ (1.5 g) in water (120 ml) was added and the organic solvent removed by evaporation. The aqueous phase was extracted with ethyl acetate (2×70 ml) and the combined organic phases were dried (Na$_2$SO$_4$) and evaporated. The product was purified by preparative HPLC. Yield: 0.44 g (75%).

$^1$H NMR (CD$_3$CN): 8.87 (t, J=2.0 Hz, 1H), 8.63 (t, J=2.0 Hz, 2H), 4.98 (t, J=6.0 Hz, 1H), 3.64–3.79 (m, 2H), 2.34 (s, 2H).

MS (ESP$^-$, m/e): 227 (M$^-$, 50%), 197 ([M–CH$_2$O]$^-$, 100%).

d. 1-(1,2-Dihydroxyethyl)-3,5-diaminobenzene 1-(1,2-Dihydroxyethyl)-3,5-dinitrobenzene (0.10 g, 0.44 mmol) was dissolved in methanol (35 ml) and hydrogenation was carried out at 60 psi using a Pd/C catalyst (10%, 50 mg). The catalyst was filtered off and the solution was evaporated. Yield: 0.074 g (100%).

$^1$H NMR (CD$_3$OD): 6.14 (d, J=2.0 Hz, 2H), 6.06 (t, J=2.0 Hz, 1H), 4.98 (br s, 6H), 4.43–4.50 (m, 1H), 3.52–3.57 (m, 2H).

MS (ESP, m/e): 170 (M+, 100%), 210 ([M+K]+, 18%).

e. 1-(1,2-Dihydroxyethyl)-3,5-diamino-2,4,6-triiodobenzene 1-(1,2-Dihydroxyethyl)-3,5-diaminobenzene (0.0584 g, 0.242 mmol) was dissolved in a mixture of methanol (5 ml) and aqueous 2 M HCl (1.2 ml) and a solution of KICl$_2$ (70% in water, 0.97 mmol) was added in one portion. After stirring for 20 min at room temperature, a 10% aqueous NaHSO$_3$ solution (0.2 ml) was added, the solvents were removed by evaporation and the residue was purified by preparative HPLC. Yield: 31.4 mg (24%).

$^1$H NMR (CD$_3$OD): 5.56–5.63 (m, 1H), 4.03–4.12 (m, 1H), 3.79–3.87 (m, 1H), 5.06 (br s, 4H).

f. 1-(1 2-Dihydroxyethyl)-3,5-di(hydroxyacetylamino)-2,4,6-triiodobenzene 1-(1,2-Dihydroxyethyl)-3,5-diamino-2,4,6-triiodobenzene is acylated with acetoxyacetyl chloride using for example such a procedure as described in Example 4d. The crude product is then hydrolyzed analogous to Example 4e to give the final product. Purification of the crude product is carried out using preparative HPLC.

EXAMPLE 24

5-(Hydroxyacetamido)-3-hydroxymethyl-N-(2,3-dihydroxypropyl)-2,4,6-triiodobenzamide a. Methyl-(5-nitro-3-hydroxymethyl)-benzoate 5-Nitro-monomethylphthalate (100 g, 0.44 mol) was dissolved in 2.5 l of dry tetrahydrofuran in a three-necked flask. Boron trifluoride diethyl etherate (126.0 g, 0.88 mol) was added with efficient stirring at room temperature and under inert atmosphere. Sodium borohydride (22.6 g, 0.60 mol) was added portionwise during 1h. After stirring overnight, ethanol (100 ml) was added to the reaction mixture. Diethyl-ether (2 l) and water (0.5 l) were then added and the phases separated. The organic phase was washed with a saturated solution of sodium hydrogen carbonate (1000 ml). The organic phase was dried (Na$_2$SO$_4$) and the solvent evaporated leaving 91.0 g (97%) of a light yellow crystalline residue.

$^1$H NMR (DMSO-d$_6$): 8.64 (d, 1H, J=2 Hz), 8.44 (d, 1H, J=2 Hz), 8.35 (t, 1H), 4.79 (s, 2H), 3.96 (s, 3H).

b. 5-Nitro-3-hydroxymethylbenzoic acid

Methyl-(5-nitro-3-hydroxymethyl)-benzoate (85.0 g, 0.40 mol) was dissolved in 15 ml of tetrahydrofuran by warming. After cooling to room temperature, a solution of sodium hydroxide (16.1 g, 0.40 mol) in water (150 ml) was slowly added with efficient stirring. After 30 minutes, the mixture was acidified to pH=2 with 6M hydrochloric acid. A white precipitate was formed, and after cooling in an ice-bath, the precipitate was filtered off and sucked dry on a filter. Yield after drying under vacuum was 79.2 g (100%).

$^1$H NMR (DMSO-d$_6$): 8.27–8.74 (m. 2H), 7.67–8.02 (m, 1H), 4.63 (d, 2H, J=3 Hz), 4.15 (br. s, 2H).

$^{13}$C NMR (DMSO-d$_6$): 166.0, 148.3, 146.4, 145.2, 133.2, 132.7, 130.8, 124.9, 122.4, 119.4, 62.3, 61.9.

c. 5-Amino-3-hydroxymethylbenzoic acid

5-Nitro-3-hydroxymethyl benzoic acid (39.6 g, 0.20 mol) was suspended in a mixture of dioxane (25 ml) and water (50 ml). Palladium on carbon (5%) was added and the mixture was hydrogenated in a Parr apparatus until the stoichiometric amount of hydrogen had been consumed. The catalyst was filtered off and the filtrate passed into concentrated hydrochloric acid (12M, 17 ml). The filtrate was evaporated to dryness to give 40.6 g of a crystalline product. Yield is almost quantitative. The product was used without further purification.

MS (ESP, m/e): 166 ([M]+, 100%).

d. 5-Amino-3-hydroxymethyl-2,4,6-triiodobenzoic acid

5-Amino-3-hydroxymethylbenzoic acid-hydrochloride salt (20.4 g, 0.10 mol) was dissolved in water (800 ml) and concentrated hydrochloric acid (40 ml) was added. A 70% w/w solution of potassium iododichloride (79.0 g, 0.23 mol) was added dropwise during 2 h at room temperature with efficient stirring. Another portion of KICl$_2$ solution (39.5 g, 0.12 mol) was then added quickly and the mixture was stirred at 50° C. for 12 h. After cooling, the brown precipitate was filtered off. The filtercake was dissolved in 340 ml of 2% solution of sodium hydroxide containing sodium hydrogen sulphite (1.0 g) and stirred for 15 min, at room temperature. The solution was then acidified to pH=2 with concentrated hydrochloric acid. The precipitate formed was filtered off and dried. The dried filtercake was triturated with a mixture of 95% methylene chloride and 5% methanol (2×100 ml). After drying 45.6 g (84%) of a white to grey powder was obtained $^1$H NMR (DMSO-d$_6$): 5.53 (s, 2H), 5.48 (s, 1H), 5.10 (s, 2H), 3.92 (s, 1H).

MS (ESP, m/e): 544 ([M]+, 100%).

e. 5-Amino-3-acetoxymethyl-2,4,6-triiodobenzoic acid

5-Amino-3-hydroxymethyl-2,4,6-triiodobenzoic acid (41.2 g, 0.076 mol) was dissolved in pyridine (100 ml), and acetic anhydride (80 ml) was added slowly with efficient stirring at room temperature. Stirring was continued overnight. The reaction mixture was then evaporated to a semisolid mass and treated with hydrochloric acid (2M, 250 ml). The white to grey precipitate formed was filtered off and washed with water (2×40 ml) and then dried. 44.2 g (100%) of product was isolated.

$^1$H NMR (DMSO-d$_6$): 5.43 (br. s, 2H), 5.35 (s, 2H), 3.45 (br. s, 1H), 2.03 (s, 3H).

$^{13}$C NMR (DMSO-d$_6$): 170.2, 170.0, 148.7, 148.6, 139.9, 88.2, 80.3, 79.5, 76.9, 20.4.

f. 5-Amino-3-acetoxymethyl-2,4,6-triiodobenzoyl chloride

5-Amino-3-acetoxymethyl-2,4,6-triiodobenzoic acid (43.9 g, 0.075 mol) was suspended in 1,2-dichloroethane (40 ml) and thionyl chloride (24.9 ml, 0.34 mol) was added. The mixture was heated to reflux temperature for 3 h. After evaporation to dryness, the residue was dissolved in tetrahydrofuran (50 ml). Sodium hydrogen carbonate (15 g) and crystalline sodium carbonate (5 g) were added to the solution and the mixture was stirred at room temperature for 3 h. The mixture was filtered and the filtrate evaporated to dryness. After pump-drying, a foam was formed, yield 44.6 g (98%).

This material was used directly in the next step.

g. 5-Amino-3-acetoxymethyl-N-(2,3-dihydroxypropyl)-2,4,6-triiodobenzamide

5-Amino-3-acetoxymethyl-2,4,6-triiodobenzoyl chloride (12.0 g, 0.020 mol) was dissolved in 10 ml of dioxane and sodium carbonate (2.1 g, 0.020 mol) was added. To this solution was added a solution of 2,3-dihydroxypropylamine (1.8 g, 0.020 mol) dissolved in 15 ml of dioxane. The mixture was heated to reflux for 10 h. After cooling to room temperature, methanol (25 ml), strongly acidic ion exchange resin (Amberlyst 15, 50 g) and water (25 ml) were added to bring the pH to 3 to 4. After stirring at room temperature for 20 min, the resin was filtered off and the filtrate was evaporated to dryness. The semisolid dark crude product (12.6 g) was acetylated directly in the next step.

MS (ESP, m/e): 660 ([M]+, 100%).

h. 5-Amino-3-acetoxymethyl-N-(2,3-diacetoxypropyl)-2,4,6-triiodobenzamide

5-Amino-3-acetoxymethyl-N-(2,3-dihydroxypropyl)-2,4,6-triiodobenzamide (2.13 g, 3.23 mmol) was dissolved in pyridine (12 ml). Acetic anhydride (10 ml) was added dropwise with efficient stirring. Stirring was continued at ambient temperature for 10 h. The reaction mixture was then evaporated to a solid residue, which was taken up in chloroform (70 ml). The organic phase was washed with aqueous hydrochloric acid (1M) until pH=2, then twice with water (40 ml) and last with a saturated solution of sodium hydrogen carbonate until pH=8–9. After drying ($Na_2SO_4$), the solvent was evaporated to yield a dark solid residue. This was taken up in a mixture of methylene chloride/ethyl acetate (90/10) and eluted through a pad of alumina. After evaporation of the solvent, 2.1 g (87%) of a white crystalline residue was left.

MS (ESP, m/e): 744 ($[M]^+$, 100%), 766 ($[M+Na]^+$, 20%).

$^1$H NMR (DMSO-$d_6$): 6.14 (t, 1H, J=6 Hz), 5.49 (s, 2H), 5.22–5.31 (m, 1H), 5.12 (s, 2H), 4.37–4.45 (m, 1H), 4.21–4.32 (m, 1H), 3.73–3.93 (m, 1H), 3.48–3,68 (m, 1H), 2.21 (s, 3H), 2.10 (br. s, 6H).

i. 5-Acetoxyacetamido-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (3.0 g, 4.03 mmol) was dissolved in dry N,N-dimethylacetamide (8 ml) at ambient temperature. With efficient stirring acetoxyacetyl chloride (4.39 ml, 40.3 mmol) was added dropwise, and the mixture was stirred overnight. The mixture was then added slowly with stirring into a saturated solution of sodium hydrogen carbonate (80 ml). The precepitate formed was filtered off and dissolved in chloroform (80 ml). The organic solution was washed with an aqueous saturated solution of $NaHCO_3$ (25 ml), and then evaporated to dryness. The solid residue was dissolved in acetone and filtered through a pad of alumina with acetone as eluent. Evaporation of the solvent gave 3.38 g (100%) of a white crystalline product.

MS (ESP, m/e): 845 ($[M]^+$, 100%), 784 ($[M-OAc]^+$, 15%).

$^1$H NMR (DMSO-$d_6$): 9.14 (br. s, 1H), 7.05–7.13 (m, 1H), 5.51 (s, 2H), 5.20–5.30 (m, 1H), 4.76 (s, 2H), 4.35–4.45 (m, 1H), 4.18–4.28 (d, 1H, J=7 Hz), 3.72–3.86 (m, 1H), 3.51–3.65 (m, 1H), 2.06 (s, 3H), 2.03 (s, 9H).

$^{13}$C NMR (DMSO-$d_6$): 170.7, 170.6, 170.4, 170.3, 166.0, 150.1, 142.6, 106.8, 98.1, 97.3, 97.2, 70.0, 63.1, 63.0, 40.0, 21.5, 21.1, 20.5.

j. 5-Hydroxyacetamido-3-hydroxymethyl-N-(2,3-dihydroxyproryvl)-2,4,6-triiodobenzamide 5-Acetoxyacetamido-3-acetoxymethyl-N-( 2,3-diacetoxypropyl)-2,4,6-triiodobenzamide (1.0 g, 1.2 mmol) was dissolved in methanol (1 ml) at room temperature. A solution of sodium hydroxide (2 M, 3.5 ml) was slowly added with efficient stirring. After 30 minutes the reaction mixture was neutralized with a strong acidic ion exchange resin (Amberlyst 15). The resin was filtered off and the aqueous solution was evaporated to dryness. The residue was purified by preparative HPLC. Yield: 0.64 g (79%).

MS (ESP, m/e): 678 ($[M]^+$, 100%).

$^1$H NMR (DMSO-$d_6$): 9.79 (s, 1H), 8.33, 8.50 (2 t, 1H, J=5 Hz), 5.66 (s, 1H), 5.19 (s, 1H), 4.96 (s, 2H), 4.68 (s, 1H), 4.48 (s, 1H), 4.01 (br. d, 2H, J=6 Hz), 3.65–3.77 (m, 1H), 3.40–3.58 (m, 2H), 3.08–3.30 (m, 2H).

$^{13}$C NMR (DMSO-$d_6$): 170.5, 170.4, 170.2, 150.3, 146.0, 143.3, 143.1, 106.6, 98.7, 97.4, 97.3, 74.6, 70.0, 64.0, 61.9, 42.7.

EXAMPLE 25

5-[N'-(2-Hydroxyethyl)-hydroxyacetamido]-3-hydroxymethyl-N-(2,3-dihydroxyoropyl)-2,4,6-triiodobenzamide a. 5-[N'-(2-Acetoxyethyl)-acetoxyacetamido]-3-acetoxymethyl-N-(2,3-diacetoxypropyl)-2,4,6-triiodobenzamide 5-Acetoxyamido-3-acetoxymethyl-N-(2,3-diacetoxypropyl)-2,4,6-triiodobenzamide (2.58 g, 3.05 mmol) was dissolved in dimethyl sulfoxide (5 ml) at room temperature. 2-Bromoethyl acetate (0.40 ml, 3.66 mmol) was added and the mixture cooled in an ice bath. Cesium carbonate (0.99 g, 3.05 mmol) was added portionwise. The mixture was stirred at room temperature for 5 h. The reaction mixture was added to aqueous hydrochloric acid (0.5 M, 50 ml). The precipitate formed and was filtered off, redissolved in methylene chloride (60 ml) and the solution washed with water (5×30 ml). The organic phase was dried ($Na_2SO_4$), and the solvent evaporated. A light yellow crystalline residue of 2.76 g (97%) was left.

MS (ESP, m/e): 932 ($[M]^+$, 100%), 1061 ($[M+Cs]^+$, 15%).

$^1$H NMR (CDCl$_3$): 6.26–6.52 (2m, 1H), 5.57 (br. s, 2H), 5.23–5.31 (m, 1H), 3.47–4.64 (m, 10H), 2.10 (br. s, 15H).

$^{13}$C NMR (CDCl$_3$): 170.9, 170.8, 170.7, 166.3, 166.1, 151.6, 145.9, 144.2, 144.1, 108.0, 99.3, 99.0, 97.4, 70.1, 70.0, 63.8, 62.9, 62.8, 61.9, 61.0, 40.2, 28.6, 21.2, 21.0, 20.8, 20.7, 20.5.

b. 5-[N'-(2-Hydroxyethyl)-hydroxyacetamido]-3-hydroxymethyl-N-(2,3-dihydroxypropyl)-2,4,6-triiodobenzamide 5-[N'-(2-acetoxyethyl)-acetoxyacetamido]-3-acetoxymethyl-N-(2,3-diacetoxypropyl)-2,4,6-triiodobenzamide (2.76 g, 2.96 mmol) was dissolved in methanol (4 ml) at room temperature. An aqueous solution of sodium hydroxide (2M, 11.1 ml) was slowly added with efficient stirring. After 30 minutes, the pH of the solution was adjusted to 6 by the addition of a strongly acidic ion exchange resin (Amberlyst 15). The resin was filtered off and the solution was evaporated to a crystalline residue. The product was purified by preparative HPLC. Yield: 1.80 g (84%).

$^1$H NMR (DMSO-$_6$): 8.44–8.58 (m, 1H), 5.25 (br. s, 1H), 4.97 (s, 2H), 4.72 (br. s, 2H), 3.00–3.75 (m, 11H).

$^{13}$C NMR (DMSO-$d_6$): 171.3, 170.9, 170.1, 170.0, 151.7, 147.4, 145.6, 107.4, 100.0, 99.3, 74.7, 70.1, 69.9, 64.0, 63.9, 61.7, 61.5, 58.5, 58.3, 51.5, 51.3, 42.5.

EXAMPLE 26

5-[N'-(2,3-Dihydroxypropyl)-hydroxyacetamido]-3-hydroxymethyl-N-(2,3-dihydroxypropyl)-2,4,6-triiodobenzamide a. 5-[N'-(2,2-Dimethyl-1,3-dioxolane-4-methyl)-acetoxyacetamido]-3-acetoxymetyl-N-(2,3-diacetoxypropyl)-2,4,6-triiodobenzamide 5-Acetoxyacetamido-3-acetoxymethyl-N-(2,3-diacetoxypropyl)-2,4,6-triiodobenzamide (0.97 g, 1.15 mmol) was dissolved in dimethyl sulfoxide (3.0 ml) and cesium carbonate (0.38 g, 1.15 mmol) was added at room temperature. 4-Bromomethyl-2,2-dimethyl-1,3-dioxolane (0.34 g, 1.74 mmol) was added and the mixture was heated to 55° C. with efficient stirring. After 48 h the reaction mixture was cooled and poured into water (60 ml). The precipitate formed was filtered off and dissolved in ethyl acetate (60 ml). The organic phase was washed with a saturated sodium chloride solution (7×45 ml). After drying ($Na_2SO_4$), the solvent was evaporated leaving a yellow foam of 1.0 g (91%).

MS (ESP, m/e): 958 ($[M]^+$, 100%), 1089 ($[M+Cs]^+$, 15%).

$^1$H NMR (CDCl$_3$): 6.10–6.30 (m,1H), 5.59 (br. s, 2H), 5.17–5.36 (m,1H), 4.02–4.60 (m, 9H), 3.28–3.94 (m, 2H), 2.08, 2.20 (2s, 12H), 1.44 (s, 3H), 1.35 (s, 3H).

b. 5-[N'-(2,3-Dihyroxypropyl)-hydroxyacetamido]-3-hydroxymethyl-N-(2,3-dihydroxypropyl)-2,4,6-triiodobenzamide 5-[N'-(2,2-dimethyl-1,3-dioxolane-4-methyl]-3-acetoxymethyl-N-(2,3-diacetoxypropyl)-2,4,6-triiodobenzamide (1.05 g, 1.10 mmol) was dissolved in methanol (10 ml), and potassium carbonate (0.30 g, 2.2 mmol) was added. The mixture was stirred at room temperature for 17 h, filtered and the filtrate was then acidified with hydrochloric acid (5M) to pH=1. This solution was then stirred at room temperature for 5 h, and then evaporated to dryness. The residue was purified by preparative HPLC giving 0.36 g (44%) of the product, as a white solid.

MS (ESP, m/e): 781 ([M]$^+$, 100%).

$^1$H NMR (DMSO-d$_6$): 8.16, 7.83 (2t, 1H, J=6–8 Hz), 5.22 (t, 1H, J=6 Hz), 4.98 (s, 2H), 4.87 (br. s, 1H), 4.63, 476 (2s, 2H), 4.55, 4.47, 4.44 (3s, 3H), 3.64–4.4(m, 6H), 3.40–3.62 (m, 5H), 3.16–3.32 (m, 2H).

$^{13}$C NMR (DMSO-d$_6$): 172.6, 172.4, 172.0, 171.7, 169.9, 169.7, 151.9, 151.7, 147.4, 147.1, 147.0, 146.0, 107.6, 106.9, 100.0, 99.4, 98.7, 74.9, 74.6, 69.8, 68.8, 64.6, 64.4, 63.7, 63.5, 61.9, 61.7, 58.7, 54.0, 53.0, 52.2, 52.0.

EXAMPLE 27

5-(2-Hydroxypropionylamino)-3-hydroxymethyl-N-(2,3-dihydroxypropyl)-2,4,6-triiodobenzamide a. 5-(2-Acetoxypropionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (3.20 g, 4.3 mmol) was dissolved in dry dimethylacetamide (4 ml). 2-Acetoxypropionyl chloride (2.17 ml, 17.2 mmol) was then added dropwise with efficient stirring. Stirring was continued over night. After work up according to the procedure in Example 24i, 3.66 g (100%) of product was isolated.

MS (ESP, m/e): 857([M]$^+$, 100%).

$^1$H NMR (CDCl$_3$): 8.53–8.59 (s, 1H), 6.56–6.59 (m, 1H), 5.54 (br. s, 2H), 5.42 (q, 1H, J=6 Hz), 5.20–5.31 (m, 1H), 4.35–4.45 (m, 1H), 4.18–4.30 (m, 1H), 3.73–3.80 (m, 1H), 3.53–3.68 (m, 1H), 2.08 (s, 3H), 2.06 (s, 9H), 1.63 (d, 3H, J=6 Hz).

$^{13}$C NMR (CDCl$_3$): 170.7, 170.6, 170.3, 170.1, 169.5, 168.7, 150.1, 142.8, 106.6, 97.4, 70.6, 70.5, 70.0, 63.0, 40.0, 21.5, 21.2, 20.8, 20.6, 17.7.

b. 5-(2-Hydroxypropionylamino)-3-hydroxymethyl-N-(2,3-dihydroxypropyl)-2,4,6-triiodobenzamide 5-(2-Acetoxypropionylamino)-3-acetoxymethyl-N-(2,3-diacetoxypropyl)-2,4,6-triiodo benzamide was hydrolysed according to the procedure described in Example 24j. The product was purified by preparative HPLC and isolated in 44% yield.

MS (ESP, m/e): 692 ([M]$^+$, 100%).

$^1$H NMR (DMSO-$_6$): 9.96, 9.73 (2s, 1H) , 8.34–8.51 (m, 1H), 5.58–5.67 (m, 1H), 5.18 (q, 1H, J=5 Hz), 4.96 (br. s, 2H), 4.69 (t, 1H, J=5 Hz), 4.48 (q, 1H, J=6 Hz), 4.09–4.20 (m, 1H), 3.64–3.76 (m, 1H), 3.35–3.53 (m, 2H), 3.06–3.33 (m, 2H), 1.38 (d, 3H, J=7 Hz).

$^{13}$C NMR (DMSO-d$_6$): 173.1, 173.0, 170.6, 150.7, 146.4, 144.0, 143.7, 143.5, 107.2, 107.1, 99.1, 99.0, 97.8, 97.7, 75.0, 70.4, 70.3, 68.0, 64.4, 43.1, 21.5.

EXAMPLE 28

5-[N'-(2-Hydroxyethyl)-2-hydroxypropionylamino]-3-hydroxymethyl-N-(2,3-dihydroxypropyl)-2,4,6-triiodobenzamide a. 5-[N'-(2-Acetoxyethyl)-2-acetoxypropionylamino]-3-acetoxymethyl-N-(2,3-di-acetoxypropyl)-2,4,6-triiodobenzamide 5-(2-Acetoxypropionylamino)-3-acetoxymethyl-N-(2,3-diacetoxypropyl)-2,4,6-triiodobenzamide was alkylated with 2-bromoethyl acetate according to the general procedure described in Example 25a. After work up the product was isolated in 95% yield.

MS (ESP, m/e) 943 ([M]$^+$, 100%), 1073 ([M+Cs]$^+$, 20%).

$^1$H NMR (CDCl$_3$): 6.27–6.56 (m, 1H), 4.98–5.60 (m, 4H), 3.46–4.44 (m, 8H), 2.16 (s, 3H), 2.09 (s, 12H), 1.33–1.43 (m, 3H).

$^{13}$C NMR (CDCl$_3$): 170.8, 170.7, 170.6, 170.5, 151.5, 147.3, 143.9, 143.7, 108.2, 108.1, 100.2, 98.6, 98.5, 97.7, 97.4, 70.1, 70.0, 69.9, 68.3, 65.9, 63.8, 63.0, 62.9, 61.8, 61.7, 49.6, 48.5, 40.1, 40.0, 30.9, 28.6, 21.1, 21.0, 20.8, 20.7, 20.6, 18.6, 17.1.

b. 5-[N'-(2-Hydroxyethyl)-2-hydroxypropionylamino]-3-hydroxymethyl-N-(2,3-dihydroxypropyl)-2,4,6-triiodobenzamide 5-[N'(2-Acetoxyethyl)-2-acetoxypropionylamino]-3-acetoxymethyl-N-(2,3-diacetoxypropyl)-2,4,6-triiodobenzamide was hydrolysed according to the general procedure in Example 24j. The product was isolated in 47% yield, after purification by HPLC.

MS (ESP, m/e): 734 ([M]$^+$, 100%).

$^1$H NMR (DMSO-d$_6$): 8.42–8.61 (m, 1H), 5.14–5.30 (m, 1H), 5.00 (br. s, 2H), 4.73–4.92 (m, 3H), 4.44–4.64 (m, 1H), 2.98–3.78 (m, 10H), 1.07–1.14, 1.33–1.37 (2m, 3H).

$^{13}$C NMR (DMSO-d$_6$): 174.4, 174.0, 170.6, 152.0, 147.6, 147.5, 147.2, 147.0, 109.2, 108.1, 101.5, 101.4, 99.2, 75.4, 75.1, 70.5, 70.3, 65.5, 65.4, 65.3, 65.0, 64.9, 64.4, 58.8, 58.6, 52.4, 52.1, 43.1, 42.9, 22.0, 21.7, 21.1.

EXAMPLE 29

5-(2,3-Dihyroxypropionylamino)-3-hydroxymethyl-N-(2,3-dihydroxyropyl)-2,4,6-triiodobenzamide a. 5-(2,2-Dimethyl-1,3-dioxolane-4-carbamido)-3-acetoxymethyl-N-(2,3-diacetoxypropyl)-2,4,6-triiodobenzamide Potassium 2,2-dimethyl-1,3-dioxolane-4-carboxylate (1.84g, 10 mmol) was suspended in 35 ml of dry ether. Oxalyl chloride (0.87 ml, 10 mmol) was added very slowly with efficient stirring at 0° C. under inert atmosphere.

After stirring at this temperature for 2 h, the temperature was allowed to reach room temperature and stirring was continued for 20 h. The precipitate formed was filtered off, and the filtrate evaporated to give an oil.

5-Amino-3-acetoxymethyl-N-(2,3-diacetoxypropyl)-2,4,6-triiodobenzamide was dissolved in dry dimethylacetamide (10 ml) and added dropwise to the oil above under an inert atmosphere. Stirring was continued at room temperature for 48 h. The reaction mixture was slowly added to 2% aqueous solution of sodium hydrogen carbonate (100 ml). A very light tan coloured precipitate was formed, filtered off, washed with water (25 ml) and dried. The isolated product (2.02 g , 70%) was used without further purification.

MS (ESP, m/e): 872 ([M]$^+$, 100%).

$^1$H NMR (DMSO-d$_6$): 10.70, 9.92 (2 br s, 1H), 8.77–8.90 (m, 1H), 5.46 (s, 2H), 5.09 (t, 1H, J=6 Hz), 4.59 (m, 1H), 4.23–4.38 (m, 2H), 4.05–4.22 (m, 2H), 3.30–3.58 (m, 2H), 1.98–2.11 (2s, 9H), 1.56 (s, 3H), 1.38 (s, 3H).

$^{13}$C NMR (DMSO-d$_6$): 170.7, 170.5, 170.4, 169.4, 169.3, 150.0, 143.8, 141.5, 111.1, 108.3, 101.0, 99.0, 98.8, 77.4, 75.3, 69.9, 63.5, 35.0, 21.8, 21.5, 21.0, 20.7.

b. 5-(2,3-Dihydroxypropionylamino)-3-hydroxymethyl-N-(2,3-dihydroxypropyl)-2,4,6 -triiodobenzamide 5-(2,2-Dimethyl-1,3-dioxolane-4-carbamido)-3-acetoxymethyl-N-(2,3-diacetoxypropyl)-2,4,6-triiodobenzamide (0.80 g, 9.16 mmol) was dissolved in methanol (7 ml) and potassium carbonate (0.17 g, 12,3 mmol) was added. The mixture was stirred at room temperature for 17 h. The mixture was filtered and pH of the filtrate was adjusted to 1 using aqueous 5M hydrochloric acid, and the mixture was stirred for further 5 h at room temperature. The reaction mixture was then evaporated to a solid residue, which was purified by preparative HPLC. Yield: 0.41 g (49%) of a white freeze dried product.

MS (ESP, m/e): 706 ([M]$^+$, 100%)

$^1$H NMR (DMSO-d$_6$): 9.77 (s, 1H), 8.32–8.48 (m, 1H, J=5 Hz), 5.76–5.84 (m, 1H), 5.18 (br. s, 1H), 4.95 (br. s, 2H), 4.83 (s, 1H), 4.70 (s, 1H), 4.46–4.53 (m, 1H), 4.03–4.11 (m, 1H), 3.46–3.83 (m, 5H,), 3.07–3.34 (m, 2H,).

$^{13}$C NMR (DMSO-d$_6$): 170.5, 170.4, 170.2, 150.3, 146.0, 143.3, 143.1, 98.7, 97.3, 97.2, 74.7, 73.8, 70.0, 64.2, 64.0, 42.7.

EXAMPLE 30

5-[N'-(2-Hydroxyethyl)-2,3-dihyroxypropionylamino]-3-hydroxymethyl-N-(2,3-dihyroxypropyl)-2,4,6-triiodobenzamide a. 5-[N'-(2-Acetoxyethyl)-2,2-dimethyl-1,3-dioxolane-4-carboxamido]-3-acetoxymethyl-N-(2,3-diacetoxypropyl)-2,4,6-triiodobenzamide 5-(2,2-Dimethyl-1,3-dioxolane-4-carboxamido)-3-acetoxymethyl-N-(2,3-diacetoxypropyl)-2,4,6-triiodobenzamide (0.44 g, 0.50 mmol) was dissolved in dimethylsulfoxide (3 ml) and cesmium carbonate (0.33 g, 1.0 mmol) was added. 2-Bromoethyl acetate (0.25 g, 2.5 mmol) was added dropwise. The mixture was stirred at 45° C. for 17 h then added slowly into water (50 ml). A precipitate was formed, filtered off and the filtercake was dissolved in chloroform (60 ml). The organic phase was washed with water (2×30 ml), then dried (Na$_2$SO$_4$) and evaporated to a solid product. Yield: 0.46 g (93%).

MS (ESP, m/e): 958 ([M]$^+$, 100%), 1090 ([M+Cs]$^+$, 20%).

$^1$H NMR (CDCl$_3$): 6.43, 6.25 (2 br. d, 1H, J=6 Hz), 5.59 (t, 1H, J=5 Hz), 5.23–5.32 (m,1H), 3.52–4.65 (m, 12H), 2.11 (s, 12H).

$^{13}$C NMR (CDCl$_3$): 170.8, 170.7, 149.6, 144.1, 140.1, 140.0, 139.6, 136.2, 128.5, 127.7, 103.0, 98.7, 98.6, 70.8, 70.1, 70.0, 63.8, 63.0, 62.9, 62.2, 61.7, 40.9, 30.9, 28.6, 20.8, 20.6.

b. 5-[N'-(2-Hydroxyethyl)-2,3-dihydroxypropionylamino]-3-hydroxymethyl-N-(2,3-dihydroxypropyl)-2,4,6-triiodobenzamide 5-[N'-(2-Acetoxyethyl)-2,2-dimethyl-1,3-dioxolane-4-carboxamido]-3-acetoxymethyl-N-(2,3-diacetoxypropyl)-2,4,6-triiodobenzamide (47 mg, 0.049 mmol) was dissolved in methanol (0.5 ml) and an aqueous solution of sodium hydroxide (2M, 0.25 ml) was added slowly followed by water (2 ml). After stirring at room temperature for 20 minutes, the reaction mixture was neutralized with a strongly acidic ion exchange resin. The resin was filtered off, and the filtrate acidified to pH=1 using hydrochloric acid (5M). After stirring at room temperature for 3.5 hours the reaction mixture was evaporated to dryness and the solid residue was purified by preparative HPLC giving 28 mg (76%) of product.

MS (ESP, m/e): 749 ([M]$^+$, 100%).

$^1$H NMR (DMSO-d$_6$): 8.34–8.55 (m, 1H), 5.09–5.30 (m, 2H), 5.10 (br. d, 2H, J=6 Hz), 4.35–4.89 (m, 6H), 3.00–3.74 (m, 10H).

$^{13}$C NMR (DMSO-d$_6$): 171.9, 170.5, 151.9, 147.5, 147.1, 146.9, 109.1, 100.1, 99.4, 99.2, 96.0, 75.4, 75.2, 71.3, 70.5, 70.3, 70.2, 64.4, 64.2, 64.0, 63.7, 58.6, 52.1, 43.0.

EXAMPLE 31

5-(3-Hydroxy-2-hydroxymethylpropionylamino)-3-hydroxymethyl-N-(2,3-dihydroxypropyl)-2,4,6-triiodobenzamide a. 5-[5-(2,2-Dimethyl-dioxane-1,3-yl)-carboxamido]-3-acetoxymethyl-N-(2,3-diacetoxypropyl)-2,4,6-triiodobenzamide 5-(2,2-Dimethyl-dioxane-1,3-yl)-carboxylic acid (1.8 g, 11.2 mmol) was dissolved in dimethylformamide (17 ml). The solution was cooled to 0° C. and thionyl chloride (0.82 ml, 11.2 mmol) was added slowly with efficient stirring. Stirring was continued at 25° C. for 5 h. 5-Amino-3-acetoxymethyl-N-(2,3-diacetoxypropyl)-2,4,6-triiodobenzamide (1.19 g, 1.6 mmol) was then added in one portion and the mixture was stirred at 45° C. for 24 h. After cooling to room temperature the reaction mixture was added slowly into a 2% aqueous solution of sodium hydrogen carbonate (150 ml). A precipitate was formed, filtered off and purified by preparative HPLC to give 0.64 g (48%) of a white crystalline product.

MS (ESP, m/e): 886 ([M]$^+$, 100%).

$^1$H NMR (CDCl$_3$): 8.19–8.30 (m, 1H), 7.28–7.32 (m, 1H), 5.52 (s, 2H), 5.18–5.26 (m, 1H), 4.33–4.41 (m, 1H), 4.17–4.24 (m, 1H), 3.96 (d, 3H, J=5 Hz), 3.67–3.82 (m, 3H), 3.41–3.60 (m, 1H), 2.68–2.76 (m, 1H), 2.04 (s,9H), 1.19 (s, 6H).

$^{13}$C NMR (CDCl$_3$): 171.0, 170.7, 170.6, 142.6, 142.4, 140.5, 140.1, 105.7, 97.8, 97.0, 96.9, 70.1, 63.2, 39.7, 21.0, 20.6, 20.4.

b. 5-(3-Hydroxy-2-hydroxymethyl-propionylamino)-3-hydroxymethyl-N-(2,3-dihydroxypropyl)-2,4,6-triiodobenzamide 5-[5-(2,2-Dimethyl-dioxane-1,3-yl)-carboxamido]-3-acetoxymethyl-N-(2,3-diacet-oxypropyl)-2,4,6-triiodobenzamide (0.19 g, 0.21 mmol) was dissolved in methanol (2 ml) and an aqueous solution of sodium hydroxide (2M, 2 ml) was added. After stirring at room temperature for 30 min, the mixture was neutralized with strong acidic ion-exchange resin. The resin was filtered off and pH was adjusted to 1 using aqueous hydrochloric acid (5M). After stirring for 5 h , the mixture was evaporated to a solid residue. Purification by preparative HPLC gave 80 mg (52%) of a white product.

MS (ESP, m/e): 720 ([M]$^+$, 100%).

$^1$H NMR (DMSO-d$_6$): 9.92 (s, 1H) , 8.38, 8.42 (2t, 1H, J=6 Hz), 5.17 (q, 1H, J=6 Hz), 4.96 (s, 2H), 4.68 (s, 1H), 4.62 (s, 1H), 4.49 (s, 1H), 3.61–3.92 (m, 5H), 3.45–3.56 (m, 2H), 3.02–3.27 (m, 2H), 2.70 (m, 1H).

$^{13}$C NMR (DMSO-d$_6$): 170.8, 170.6, 170.2, 150.4, 146.1, 143.4, 143.2, 106.7, 106.6, 98.7, 97.3, 74.7, 70.0, 69.9, 64.1, 64.0, 59.7, 51.3, 51.2, 42.7.

EXAMPLE 32

5-(3-Hydroxy-2-methyl-2-hydroxymethyl-propionylamino)-3-hydroxymethyl-N-(2,3-dihyroxypropyl)-2,4,6-triiodobenzamide a. 5-(3-Acetoxy-3-methyl-2-acetoxymethylpropionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (2.48 g, 3.30 mmol) was dissolved in dimethylacetamide (10 ml) and added dropwise to 2,2-diacetoxymethylpropionyl chloride (2.36 g, 10 mmol). Stirring was continued at 60° C. for 48 h. The reaction mixture was cooled and added to a 2% aqueous solution of sodium hydrogen carbonate (120 ml). A precipitate was formed and filtered off, redissolved in chloroform (140 ml) and the organic phase was washed with water (5×40 ml). After drying (Na$_2$SO$_4$), the solvent was evaporated leaving a gum (ca. 3 g). MS analysis showed the product to consist of two compounds:

5-(3-Acetoxy-3-methyl-2-acetoxymethylpropionylamino)-3-acetoxymethyl-N-(2,3-diacetoxypropyl)-2,4,6-triiodobenzamide with MS (ESP, m/e): 944 ([M]$^+$, 100%).

5-Acetamido-3-acetoxymethyl-N-(2,3-diacetoxypropyl)-2,4,6-triiodobenzamide with MS (ESP, m/e): 786 ([M]+, 80%).

The product was used in the next step without further purification.

b. 5-(3-Hydroxy-3-methyl-2-hydroxymethyl-propionylamino)-3-hydroxymethyl-N-(2,3-dihydroxypropyl)-2,4,6-triiodobenzamide The product mixture from Example 32a, was dissolved in acetonitrile (10 ml). Aqueous sodium hydroxide (2M, 17 ml, 33 mmol) was added and the mixture stirred at room temperature for 1 h. The mixture was then neutralized with a strongly acidic ion exchange resin. The resin was filtered off and the filtrate was evaporated to dryness. A semisolid residue was left which was purified by preparative HPLC. Yield: 1.02 g (42%).

MS (ESP, m/e): 734 ([M]+, 100%).

$^1$H NMR (DMSO-d$_6$): 9.57 (s, 1H), 8.32, 8.41 (2t, 1H, J=5 Hz), 5.17 (t, 1H, J=6 Hz), 4.96 (br. s, 2H), 4.82, 4.95 (2s, 2H), 4.68 (d, 1H, J=6 Hz), 4.47, 4.49 (2d, 1H, J=6 Hz), 3.58–3.78 (m, 5H), 3.42–3.51 (m, 2H), 3.06–3.20 (m, 2H), 1.17, 1.15 (2s, 3H).

$^{13}$C NMR (DMSO-d$_6$): 173.3, 173.2, 170.2, 150.4, 146.1, 143.2, 106.5, 106.3, 98.5, 97.2, 74.6, 70.0, 69.9, 64.1, 63.5, 48.5, 48.4, 42.7, 17.1.

The by-product 5-acetamino-3-hydroxymethyl-N-(2,3-dihydroxypropyl)-2,4,6-triiodobenzamide was isolated in a yield of 16%.

EXAMPLE 33

5-(3-Hydroxy-2,2-dihydroxymethyl-propionylamino)-3-hydroxymethyl-N-(2,3-dihydroxyiropyl)-2,4,6-triiodobenzamide a. 5-(3-Acetoxy-2,2-diacetoxymethyl-propionylamino)-3-acetoxymethyl-N-(2,3-diacetoxypropyl)-2,4,6-triiodobenzamide 5-Amino-3-acetoxymethyl-N-(2,3-diacetoxypropyl)-2,4,6-triiodobenzamide (1.05 g, 1.43 mmol) was dissolved in dimethylacetamide (2 ml) and added to trisacetoxymethylacetyl chloride (2.17 g, 7.4 mmol). The mixture was stirred at 60° C. for 5 days, and after cooling the mixture was added to an aqueous solution of sodium hydrogen carbonate (60 ml , 2%). The precipitate formed was filtered off and dissolved in chloroform (90 ml). The organic phase was washed with water (4×40 ml), dried (Na$_2$SO$_4$), and the solvent evaporated. A semisolid residue (1.16 g) was left, which according to MS analysis consisted of the two compounds:

5-(3-Acetoxy-2,2-diacetoxymethyl-propionylamino)-3-acetoxymethyl-N-(2,3-diacetoxypropyl)-2,4,6-triiodobenzamide with MS (ESP, m/e): 1002 ([M]+, 100%) and 5-acetamido-3-acetoxymethyl-N-(2,3-diacetoxypropyl)-2,4,6-triiodobenzamide with MS (ESP, m/e): 786 ([M]+, 70%).

HPLC analysis showed two compounds in ratio 2:3. The product mixture was used without further purification.

b. 5-(3-Hydroxy-2,2-dihydroxymethyl-propionylamino)-3-hydroxymethyl-N-(2,3-dihydroxypropyl)-2,4,6-triiodobenzamide The product mixture in Example 33 a was dissolved in acetonitrile (3 ml) and hydrolysed according to the procedure in Example 32b. After preparative HPLC and freeze drying 0.30 g (29.8%) of a white product was isolated.

MS (ESP, m/e): 750 ([M]+, 100%).

$^1$H NMR (DMSO-d$_6$): 9.61 (s, 1H), 8.25–8.45 (m, 1H), 5.17 (s, 1H), 4.95 (s, 2H), 4.64, 4.88 (2s, 4H), 4.48 (s, 1H), 3.80 (s, 6H), 3.65–3.74 (m, 1H), 3.45–3.49 (m, 2H), 3.06–3.28 (m, 2H).

$^{13}$C NMR (DMSO-d$_6$): 172.0, 170.1, 150.4, 146.1, 143.0, 142.7, 106.2, 106.1, 98.3, 97.2, 74.6, 69.9, 64.0, 60.9, 59.6, 53.2, 42.7, 42.6.

EXAMPLE 34

5-(Hydroxyacetamido)-3-hydroxymethyl-N-(1,3,4-trihydroxybut-2-yl)-2,4,6-triiodobenzamide a. 5-Amino-3-acetoxymethyl-N-(1,3,4-trihydroxybut-2-yl)-2,4,6-triiodobenzamide 5-Amino-3-acetoxymethyl-2,4,6-triiodobenzoyl chloride (12.0 g, 19.8 mmol) was dissolved in dioxane (40 ml). 6-Amino-2,2-dimethyl-1,3-dioxepane-5-ol (3.20 g, 19.8 mmol) and sodium carbonate (2.10 g, 19.8 mmol) were added and the mixture heated to reflux for 10 h. The reaction mixture was cooled, methanol (100 ml) and water (50 ml) were added and the solution was neutralized with a strongly acidic ion exchange resin. The resin was filtered off and a aqueous solution of hydrochloric acid (2M, 20 ml) was added. The mixture was stirred at 60–70° C. for 30 min, and then evaporated to dryness, which gave a semisolid residue (13.6 g) which was used without further purification in the next steps.

MS (ESP, m/e): 689 ([M]+, 100%).

b. 5-Amino-3-acetoxymethyl-N-(1,3,4-triacetoxybut-2-yl)-2,4,6-triiodobenzamide

The crude product from Example 34a (13.6 g) was dissolved in pyridine (100 ml). Acetic anhydride (80 ml) was added dropwise, and stirring was continued at ambient temperature overnight. The reaction mixture was then evaporated to dryness. The dark residue was taken up in methylene chloride (250 ml) and the organic phase was washed with 1 M hydrochloric acid until pH=1–2 in the water phase. The organic phase was then washed with water (2×50 ml) and an aqueous saturated solution of sodium hydrogen carbonate. The organic phase was dried (Na$_2$SO$_4$) and the solvent evaporated. The residue was dissolved in a mixture of methylene chloride/ethyl acetate (4/1) and applied to a column of alumina. Elution and evaporation of eluent gave a white crystalline product (11.2 g, 69%).

MS (ESP, m/e): 816 ([M]+, 100%).

$^1$H NMR (CDCl$_3$): 6.02–6.09 (m, 1H), 5.51 (s, 2H), 5.47 (br. s, 2H), 4.68–4.76 (m, 1H), 4.20–4.45 (m, 4H), 2.81–2.85 (m, 1H), 2.11, 2.08 (2s, 12H).

$^{13}$C NMR (CDCl$_3$): 170.4, 169.9, 169.8, 148.3, 147.9, 147.8, 140.9, 88.0, 70.1, 69.6, 69.5, 63.0, 62.1, 62.0, 48.4, 35.8, 21.1, 20.9, 20.8, 20.6.

c. 5-(Acetoxyacetamido)-3-acetoxymethyl-N-(1,3,4-triacetoxybut-2-yl)-2,4,6-triiodobenzamide The general acylation procedure in Example 24i was applied to the product in Example 34b. The yield was 95%.

MS (ESP, m/e): 916 ([M]+, 100%).

$^1$H NMR (CDCl$_3$): 8.55, 8.57 (2s, 1H), 6.40 (t, 1H, J=7 Hz), 5.55 (s, 2H), 5.43–5.46 (m, 1H), 4.78 (br. s, 2H), 4.64–4.75 (m, 1H), 4.20–4.44 (m, 4H), 2.26 (s, 3H), 2.06, 2.08, 2.09 (3s, 12H).

$^{13}$C NMR (CDCl$_3$): 170.4, 170.3, 170.2, 169.8, 169.7, 149.6, 143.2, 143.1, 143.0, 142.4, 142.3, 107.3, 97.8, 97.4, 69.5, 69.2, 63.1, 63.0, 62.0, 61.9, 61.8, 48.3, 48.2, 21.1, 20.9, 20.8, 20.6.

d. 5-(Hydroxyacetamido)-3-hydroxymethyl-N-(1,3,4-trihydroxybut-2-yl)-2,4,6-triiodobenzamide Following the procedure in Example 24j, 5-(acetoxyacetamido)-3-acetoxymethyl-N-(1,3,4-triacetoxybut-2-yl)-2,4,6-triiodobenzamide was converted into the product. Yield: 77%.

MS (ESP, m/e): 708 ([M]+, 100%).

$^1$H NMR (DMSO-d$_6$): 9.78, 9.95 (2s, 1H), 7.67–7.83 (m, 1H), 4.95 (s, 2H), 3.85–4.15 (m, 4H), 3.47–3.75 (m, 4H), 3.40 (br. s, 5H).

13C NMR (DMSO-d₆): 170.5, 170.4, 169.7, 150.2, 146.1, 146.0, 143.3, 143.0, 106.7, 106.5, 99.1, 98.9, 98.4, 97.7, 97.6, 97.1, 74.7, 69.1, 63.6, 63.6, 61.9, 58.8, 52.5, 52.4, 52.3.

EXAMPLE 35

5-[N'-(2-Hydroxyethyl)-hydroxyacetamido]-3-hydroxymethyl-N-(1,3,4-trihydroxybut-2-yl)-2,4,6-triiodobenzamide a. 5-[N-(2-Acetoxyethyl)-acetoxyacetamido]-3-acetoxymethyl-N-(1,3,4-triacetoxybut-2-yl)-2,4,6-triiodobenzamide 5-(Acetoxyacetamido)-3-acetoxymethyl-N-(1,3,4-triacetoxybut-2-yl)-2,4,6-triiodobenzamide was alkylated with 2-bromoethyl acetate according to the procedure in Example 25a. Yield of crude product=97%.

MS (ESP, m/e): 1004 ([M]⁺, 100%).

¹H NMR (CDCl₃): 6.36–6.58 (m, 1H), 5.54 (br. s, 2H), 5.41–5.49 (m, 1H), 4.66 (br. s, 2H), 4.16–4.41 (m, 7H), 3.78–3.94 (m, 1H), 3.47 (t, 1H, J=6 Hz), 2.03, 2.10 (2s, 18H).

¹³C NMR (CDCl₃): 170.5, 170.4, 170.3, 170.1, 169.9, 166.2, 166.0, 151.2, 146.8, 146.1, 145.9, 144.2, 108.3, 108.1, 100.5, 99.9, 99.6, 99.3, 99.1, 98.8, 98.4, 69.6, 69.5, 63.8, 62.9, 62.8, 61.8, 60.9, 60.3, 48.9, 48.7, 48.5, 48.4, 47.6, 47.2, 28.7, 21.0, 20.8, 20.7, 20.5.

b. 5-[N'-(2-Hydroxyethyl)-hydroxyacetamido]-3-hydroxymethyl-N-(1,3,4-trihydroxybut-2-yl)-2,4,6-triiodobenzamide The product of Example 35a was hydrolysed according to the procedure in Example 25b. The yield after preparative HPLC was 46%.

MS (ESP, m/e): 751 ([M]⁺, 100%).

¹H NMR (DMSO-d₆): 7.70–8.16 (m, 1H), 5.00 (br. s, 2H), 3.44–4.92 (m, 18H).

¹³C NMR (DMSO-d₆): 171.9, 171.8, 171.3, 170.3, 170.2, 170.1, 152.3, 152.1, 147.8, 147.7, 147.6, 146.0, 145.9, 107.8, 107.6, 107.5, 100.9, 100.8, 100.0, 99.3, 64.1, 64.0, 62.2, 61.9, 59.1, 58.9, 52.8, 52.5, 52.4, 51.9, 51.7.

EXAMPLE 36

5-[N'-(2,3-Dihydroxypropyl)-hydroxyacetamido]-3-hydroxymethyl-N-(1,3,4-trihydroxybut-2-yl)-2,4,6-triiodobenzamide a. 5-[N'-(2,2-Dimethyl-1,3-dioxolane-4-methyl)-acetoxyacetamido]-3-acetoxymethyl-N-(1,3,4-triacetoxybut-2-yl)-2,4,6-triiodobenzamide Acylation of 5-amino-3-acetoxymethyl-N-(1,3,4-triacetoxybut-2-yl)-2,4,6-triiodobenzamide followed the procedure in Example 26a. Yield of crude product=97%.

MS (ESP, m/e): 1031 ([M]⁺, 100%), 1163 ([M+Cs]⁺, 21%).

¹H NMR (CDCl₃): 6.10–6.30 (m, 1H), 5.58 (br. s, 2H), 5.44–5.58 (m, 1H), 4.67–4.80 (m, 1H), 3.19–4.56 (m, 10H), 2.08, 2.12 (2s, 15H), 1.20, 1.25, 1.28, 1.34, 1.40, 1.45 (6s, 6H).

¹³C NMR (CDCl₃): 170.3, 170.2, 169.9, 169.0, 151.2, 146.9, 144.5, 144.4, 144.3, 109.8, 109.5, 99.3, 98.9, 98.8, 98.0, 97.9, 97.5, 75.2, 73.6, 69.6, 68.3, 66.3, 64.8, 62.8, 61.9, 32.7, 30.9, 26.9, 26.8, 25.4, 21.0, 20.9, 20.8, 20.6.

b. 5-[N'2,3-Dihydroxypropyl)-hydroxyacetamido]-3-hydroxymethyl-N-(1,3,4-trihydroxybut-2-yl)-2,4,6-triiodobenzamide Hydrolysis of the compound of Example 36a followed the procedure in Example 26b. Yield: 44% after preparative HPLC.

MS (ESP, m/e): 780 ([M]⁺, 100%).

¹H NMR (DMSO-d₆): 7.68–8.22 (m, 1H), 5.22 (t, 1H, J=6 Hz), 4.98 (s, 2H), 4.80–4.93 (s, 1H), 4.63, 4.76 (2s, 2H), 4.55, 4.46, 4.44 (3s, 3H), 3.64–4.04 (m, 6H), 3.40–3.62 (m, 5H), 3.16–3.32 (m, 2H).

¹³C NMR (DMSO-d₆): 172.6, 172.4, 172.0, 171.7, 169.9, 169.7, 151.9, 151.7, 147.4, 147.1, 147.0, 146.0, 107.6, 106.9, 100.0, 99.4, 98.7, 74.9, 74.6, 69.8, 69.1, 69.0, 68.8, 64.6, 64.4, 63.7, 63.5, 61.9, 61.7, 58.7, 54.0, 53.0, 52.2, 52.0.

EXAMPLE 37

5-(2-Hydroxypropionylamino)-3-hydroxymethyl-N-(1,3,4-tri-hydroxybut-2-yl)-2,4,6-triiodobenzamide a. 5-(2-Acetoxypropionylamino)-3-acetoxymethyl-N-(1,3,4-triacetoxybut-2-yl)-2,4,6-triiodobenzamide 5-Amino-3-acetoxymethyl-N-(1,3,4-triacetoxybut-2-yl)-2,4,6-triiodobenzamide was acylated according to the procedure of Example 27a. Yield of crude product=97%.

MS (ESP, m/e): 930 ([M]⁺, 100%).

¹H NMR (CDCl₃): 8.49, 8.55 (2s, 1H), 6.49–6.61 (m, 1H), 5.38–5.59 (m,4H), 4.64–4.76 (m, 1H), 4.18–4.46 (m, 4H), 2.22 (s, 3H), 2.60 (s, 12H), 1.63 (d, 3H, J=7 Hz).

¹³C NMR (CDCl₃): 170.6, 170.4, 170.3, 169.7, 169.6, 149.7, 143.0, 142.2, 107.0, 98.0, 97.9, 97.7, 97.6, 97.2, 70.6, 69.5, 69.3, 63.0, 62.0, 61.9, 48.2, 21.5, 21.1, 20.9, 20.8, 20.6, 17.7, 17.6.

b. 5-(2-Hydroxypropionylamino)-3-hydroxymethyl-N-(1,3,4-trihydroxybut-2-yl)-2,4,6-triiodobenzamide The product of Example 37a was hydrolysed according to the procedure of Example 24j. Yield (after preparative HPLC): 72%.

MS (ESP, m/e): 720 ([M]⁺, 100%).

¹H NMR (CDCl₃): 9.95, 9.72 (2s, 1H), 7.68–7.84 (m, 1H), 5.58–5.67 (m, 1H), 5.12–5.21 (m, 1H), 5.00 (br. s, 2H, J=6 Hz), 4.66–4.73 (m, 1H, J=6 Hz), 4.40–4.58 (m, 2H), 4.10–4.21 (m, 1H), 3.85–3.96 (m, 2H), 3.65–3.77 (m, 1H), 3.46–3.58 (m, 3H), 1.38 (d, 3H).

¹³C NMR (DMSO-d₆): 173.0, 170.1, 150.6, 146.4, 143.7, 143.5, 107.1, 99.5, 99.0, 98.7, 98.0, 97.4, 75.1, 69.5, 68.0, 64.0, 59.1, 52.8, 21.5.

EXAMPLE 38

5-(2,3-Dihydroxypropionylamino)-3-hydroxymethyl-N-(1,3,4-trihydroxybut-2-yl)-2,4,6-triiodobenzamide a. 5-(2,2-Dimethyl-1,3-dioxolane-4-carbamido)-3-acetoxymethyl-N-(1,3,4-triacetoxybut-2-yl)-2,4,6-triiodobenzamide 5-Amino-3-acetoxymethyl-N-(1,3,4-triacetoxybut-2-yl)-2,4,6-triiodobenzamide was acylated according to the procedure described in Example 29a. After work up the yield of crude product was 97%.

MS (ESP, m/e): 943 ([M]⁺, 100%).

¹H NMR (CDCl₃): 8.28–8.35 (2s, 1H), 6.15–6.32 (m, 1H), 5.58 (br. s, 2H), 5.42–5.53 (m, 2H,), 4.29–4.72 (m, 7H), 2.07, 2.13 (2s, 12H), 1.44, 1.51 (2s, 6H).

¹³C NMR (CDCl₃): 170.7, 170.6, 170.4, 170.3, 169.8, 169.7, 159.2, 156.2, 152.8, 149.9, 143.2, 143.1, 142.1, 140.4, 139.6, 128.5, 111.9, 111.6, 98.6, 97.6, 97.5, 97.3, 97.1, 96.6, 95.2, 75.2, 73.9, 72.9, 67.2, 62.7, 60.4, 26.9, 26.8, 26.3, 25.7, 25.4, 20.9, 20.8, 14.2.

b. 5-(2,3-Dihydroxypropionylamino)-3-hydroxymethyl-N-(1,3,4-trihydroxybut-2-yl)-2,4,6-triiodobenzamide The product of Example 38a was hydrolysed according to the procedure of Example 29b. After preparative HPLC the product was isolated in 52% yield.

MS (ESP, m/e): 736 ([M]⁺, 100%).

¹H NMR (DMSO-d₆): 9.75, 9.78 (2s, 1H), 7.66–7.82 (m, 1H), 5.73–5.84 (m, 1H), 5.10–5.38 (m, 1H), 4.95 (br. s, 2H), 4.64–4.88 (m, 2H), 4.38–4.60 (m, 2H), 4.02–4.11 (m, 2H), 3.85–3.95 (m, 2H), 3.64–3.82 (m, 2H), 3.47–3.62 (m, 3H).

¹³C NMR (DMSO-d₆): 170.8, 170.1, 150.6, 146.4, 143.7, 143.5, 99.5, 98.6, 98.0, 97.3, 75.1, 74.2, 69.4, 65.5, 64.6, 64.0, 59.1, 52.8.

EXAMPLE 39

5-[N'-(2-Hydroxyethyl)-2,3-dihydroxyropionylamino]-3-hydroxymethyl-N-(1,3,4-trihydroxybut-2-yl)-2,4,6-triiodobenzamide a. 5-[N'-(2-Acetoxyethyl)-2,2-dimethyl-1,3-dioxolane-4-carboxamido]-3-acetoxymethyl-N-(1,3,4-triacetoxybut-2-yl)-2,4,6-triiodobenzamide The product of Example 38a was N-alkylated with 2-bromoethyl acetate according to the general procedure in Example 30a. Yield of isolated crude product was 94%.

MS (ESP, m/e): 1030 ([M]⁺, 100%), 1161 ([M+Cs]⁺, 20%).

¹H NMR (CDCl₃): 6.10–6.53 (m, 1H), 5.55, 5.59, 5.62 (3s, 2H), 5.43–5.53 (m, 1H), 4.63–4.77 (m, 2H), 3.50–4.43 (m, 10H), 1.92, 1.96, 2.06, 2.11 (4s, 15H), 1.24, 1.32, 1.46, 1.50 (4s, 6H).

¹³C NMR (DMSO-d₆): 170.5, 170.4, 170.2, 170.0, 169.1, 150.9, 150.8, 150.5, 147.2, 144.0, 143.8, 143.7, 143.5, 111.5, 111.4, 99.9, 99.6, 98.3, 97.9, 97.5, 74.0, 73.8, 69.7, 69.6, 69.5, 68.1, 67.9, 67.3, 66.1, 63.8, 63.0, 62.9, 62.8, 62.0, 61.9, 60.4, 49.3, 49.2, 48.5, 48.4, 48.3, 48.1, 48.0, 47.9, 30.9, 28.7, 26.0, 25.7, 21.0, 20.9, 20.8, 20.6, 14.2.

b. 5-[N'-(2-Hydroxyethyl)-2,3-dihydroxypropionylamino]-3-hydroxymethyl-N-(1,3,4-trihydroxybut-2-yl)-2,4,6-triiodobenzamide The product of Example 39a was hydrolysed according to the procedure of Example 30b. After purification by preparative HPLC the product was isolated in 40% yield.

MS (ESP, m/e): 780 ([M]⁺, 100%).

¹H NMR (DMSO-d₆): 7.72–8.03 (m, 1H), 5.15–5.30 (m, 1H), 5.00 (s, 2H), 4.70–4.97 (m, 4H), 4.55–4.69 (m, 1H), 4.40–4.54 (m, 1H), 3.86–3.98 (m, 1H), 3.45–3.75 (m, 8H,), 3.15–3.34 (m, 4H).

¹³C NMR (DMSO-d₆): 172.0, 171.6, 171.3, 171.1, 170.0, 151.7, 151.5, 147.1, 147.0, 146.9, 146.7, 146.5, 146.4, 108.8, 108.6, 101.1, 100.7, 100.3, 99.9, 99.2, 99.1, 98.5, 98.3, 75.2, 75.0, 71.3, 71.0, 70.8, 69.1, 68.8, 68.6, 63.9, 63.7, 63.5, 63.3, 59.3, 58.7, 58.4, 58.2, 52.2, 52.5, 52.0, 51.8, 51.7, 51.5.

EXAMPLE 40

5-Hydroxyacetamido-3-hydroxymethyl-N,N-bis(2-hydroxyethyl)-2,4,6-triiodobenzamide a. 5-Amino-3-acetoxymethyl-N,N-bis(2-hydroxyethyl)-2,4,6-triiodobenzamide 5-Amino-3-acetoxymethyl-2,4,6-triiodobenzoyl chloride was reacted with diethanolamine according to the general procedure in Example 24g. Yield of isolated crude product was 98%.

¹H NMR (DMSO-d₆): 5.36 (br. s; 2H), 4.86 (br. s, 2H), 4.72 (s, 1H), 3.68 (t, 2H, J=7 Hz), 3.47–3.60 (m, 4H), 3.14 (t, 2H, J=6 Hz), 2.05 (s, 3H).

¹³C NMR (DMSO-d₆): 170.5, 170.1, 148.6, 147.8, 148.2, 147.8, 147.5, 145.1, 140.0, 88.0, 87.5, 82.4, 81.7, 81.6, 79.9, 76.9, 74.5, 66.4, 58.8, 57.7, 51.6, 48.0, 20.4.

b. 5-Amino-3-acetoxymethyl-N,N-bis(2-acetoxyethyl)-2,4,6-triiodobenzamide

The product in Example 40a was acetylated according to conditions in Example 24h. After work up and purification the product was isolated in 97% yield.

MS (ESP, m/e): 758 ([M]⁺, 100%).

¹H NMR (CDCl₃): 5.50 (s, 2H), 5.13 (br. s, 2H), 4.45 (t, 2H, J=6 Hz), 4.25 (t, 2H, J=6 Hz), 3.85 (t, 2H J=6 Hz), 3.49 (t, 2H, J=6 Hz), 2.07, 2.09, 2.11 (3s, 9H).

c. 5-Acetoxyacetamido-3-acetoxymethyl-N,N-bis(2-acetoxyethyl)-2,4,6-triiodo-benzamide After acylation of the product of Example 40b according to the method described in Example 24i, the product was isolated in 88% yield.

¹H NMR (CDCl₃): 9.08 (s, 1H), 5.54 (s, 2H), 4.79 (s, 2H), 4.40–4.48 (m, 2H,), 4.22 (t, 2H, J=6 Hz), 3.70–3.98 (m, 2H), 3.40–3.52 (m, 2H), 2.42 (s, 3H), 2.05, 2.07, 2.09 (3s, 9H).

¹³C NMR (CDCl₃): 171.2, 170.5, 170.4, 170.2, 169.7, 165.7, 148.1, 143.2, 142.9, 107.4, 98.2, 97.2, 63.1, 61.5, 61.3, 48.9, 45.3, 21.0, 20.8, 20.6.

d. 5-Hydroxyacetamido-3-hydroxymethyl-N,N-bis(2-hydroxyethyl)-2,4,6-triiodobenzamide Hydrolysis of the product of Example 40c according to the procedure of Example 24j and preparative HPLC afforded the product in 69% yield.

MS (ESP, m/e): 690 ([M]⁺, 100%.

¹H NMR (DMSO-d₆): 9.84, 9.79 (2s, 1H), 5.68 (br. s, 1H), 5.20 (br. s, 1H), 4.94 (s, 2H), 4.78 (br. s, 2H), 4.00 (s, 2H), 3.70 (t, 2H, J=6–7 Hz), 3.48–3.60 (m,4H), 3.14 (q, 2H, J=6 Hz).

¹³C NMR (DMSO-d₆): 170.6, 170.4, 170.3, 170.1, 166.4, 166.2, 150.3, 147.1, 146.8, 144.6, 144.5, 107.8, 107.6, 99.8, 99.6, 99.3, 99.1, 62.8, 62.5, 61.9, 61.5, 61.3, 61.2, 48.6, 48.3, 48.2, 45.2, 21.0, 20.9, 20.8, 20.6, 20.5.

EXAMPLE 41

5-[N'-(2-Hydroxyethyl)-hydroxyacetamido]-3-hydroxymethyl-N,N-bis(2-hydroxyethyl)-2,4,6-triiodobenzamide a. 5-[N'-(2-Acetoxyethyl)-acetoxyacetamido]-3-acetoxymethyl-N,N-bis(2-acetoxyethyl)-2,4,6-triiodobenzamide The compound of Example 40c was alkylated with 2-bromoethyl acetate acccording to the procedure of Example 25a. The crude product was isolated in 97% yield.

¹H NMR (CDCl₃): 5.56, 5.58 (2s, 2H), 4.30–4.48 (m, 8H), 3.80–3.95 (m, 4H), 3.42–3.53 (m, 2H), 1.97, 2.06, 2.14 (3s, 15H).

¹³C NMR (CDCl₃): 170.6, 170.4, 170.3, 170.1, 166.4, 166.2, 150.3, 147.1, 146.8, 144.6, 144.5, 107.8, 107.6, 99.8, 99.6, 99.3, 99.1, 62.8, 62.5, 61.9, 61.5, 61.3, 61.2, 48.6, 48.3, 48.2, 45.2, 21.0, 20.9, 20.8, 20.6, 20.5.

b. 5-[N'-(2-Hydroxyethyl)-hydroxyacetamido]-3-hydroxymethyl-N,N-bis(2-hydroxyethyl)-2,4,6-triiodobenzamide The product of Example 41a was hydrolysed according to procedure of Example 25b in a yield of 43%, after HPLC purification.

MS (ESP, m/e): 735 ([M]⁺, 100%).

¹H NMR (DMSO-d₆): 5.24 (t, 1H, J=5 Hz), 4.98 (t, 1H, J=6 Hz), 4.95 (d, 2H, J=4 Hz), 4.71–4.84 (m, 3H), 3.65–3.74 (m, 2H), 3.48–3.63 (m, 10H), 3.09–3.18 (m, 2H).

¹³C NMR (DMSO-d₆): 170.9, 170.8, 170.1, 149.8, 148.1, 148.0, 146.2, 107.9, 100.4, 100.3, 99.7, 99.6, 74.7, 61.5, 61.4, 59.0, 58.5, 57.6, 51.7, 51.4, 48.0.

EXAMPLE 42

5-(2,3-Dihydroxypropionylamino)-3-hydroxymethyl-N,N-bis(2-hydroxyethyl)-2,4,6-triiodobenzamide a. 5-(2,2-Dimethyl-1,3-dioxolane-4-carbamido)-3-acetoxymethyl-N,N-bis(2-acetoxyethyl)-2,4,6-triiodobenzamide Prepared according to Example 29a from 5-amino-3-acetoxymethyl-N,N-bis(2-acetoxyethyl)-2,4,6-triiodobenzamide. After work up the product was isolated in 96% yield.

MS (ESP, m/e): 885 ([M]+, 100%).

$^1$H NMR (CDCl$_3$): 8.51, 8.42, 8.26 (3s, 1H), 5.53 (s, 2H), 4.54–4.70 (m, 4H), 4.18–4.44 (m, 7H), 2.08, 2.05, 2.04 (3s, 9H), 1.62, 1.61, 1.55, 1.40 (4s, 6H).

$^{13}$C NMR (CDCl$_3$): 170.7, 170.6, 170.4, 170.2, 169.6, 169.2, 148.6, 143.0, 142.3, 111.9, 111.7, 111.4, 98.3, 98.0, 97.3, 75.2, 72.8, 67.1, 62.6, 61.3, 48.5, 45.0, 26.7, 26.4, 26.3, 25.7, 24.8, 21.3, 20.9, 20.5.

b. 5-(2,3-Dihydroxypropionylamino)-3-hydroxymethyl-N,N-bis(2-hydroxyethyl)-2,4,6-triiodobenzamide Prepared from the product of Example 42a according to the method in Example 29b. Isolated in 40% yield after preparative HPLC.

MS (ESP, m/e): 720 ([M]+, 100%).

$^1$H NMR (DMSO-d$_6$): 9.83, 9.77 (2s, 1H), 5.84 (s, 1H), 5.14–5.40 (m, 1H), 4.49 (s, 2H), 4.83 (br. s, 3H), 4.06 (br. s, 1H), 3.48–3.80 (m, 8H), 3.08–3.18 (m, 2H).

$^{13}$C NMR (DMSO-d$_6$): 170.5, 170.3, 148.5, 148.4, 146.5, 143.7, 106.9, 99.1, 99.0, 97.6, 97.5, 97.4, 74.6, 73.8, 72.0, 64.2, 63.6, 59.0, 57.7, 51.7, 48.1.

EXAMPLE 43

5-[N'-(2-Hydroxyethyl)-2,3-dihydroxypropionylamino]-3-hydroxymethyl-N,N-bis(2-hydroxyethyl)-2,4,6-triiodobenzamide a. 5-[N'-(2-acetoxyethyl)-2,2-dimethyl-1,3-dioxolane-4-carbamido]-3-acetoxymethyl-N,N-bis(2-acetoxyethyl)-2,4,6-triiodobenzamide Alkylation of the compound of Example 42a with 2-bromoethyl acetate was performed as described in Example 30a. The product was isolated as raw material in a yield of 80%.

MS (ESP, m/e): 972 ([M]+, 100%), 1104 ([M+Cs]+, 20%).

$^1$H NMR (CDCl$_3$): 5.59, 5.57 (2s, 2H), 4.57–4.63 (m, 1H), 4.18–4.47 (m, 10H), 3.81–3.88 (m, 2H), 3.40–3.51 (m, 2H), 2.08, 2.06 (2s, 12H), 1.62, 1.49, 1.40 (3s, 6H).

$^{13}$C NMR (CDCl$_3$): 171.0, 170.9, 170.5, 170.2, 170.0, 169.5, 149.8, 149.6, 148.9, 147.9, 144.0, 143.7, 143.5, 111.3, 110.9, 108.4, 98.3, 97.4, 91.6, 75.2, 73.8, 67.8, 67.1, 62.8, 62.1, 61.8, 61.5, 61.2, 48.6, 48.2, 45.1, 26.5, 25.7, 25.5, 25.4, 20.9, 20.8, 20.6, 20.4.

b. 5-[N'-(2-Hydroxyethyl)-2,3-dihydroxypropionylamino]-3-hydroxymethyl-N,N-bis(2-hydroxyethyl)-2,4,6-triiodobenzamide The product of Example 43a was hydrolysed according the general method in Example 30b. After preparative HPLC the product was isolated in 22% yield.

MS (ESP, m/e): 763 ([M]+, 100%).

$^1$H NMR (DMSO-d$_6$): 5.15–5.41 (m, 1H), 4.70–5.02 (m, 5H), 4.06–4.62 (br. m, 2H), 3.45–3.75 (m, 9H), 3.30–3.45 (m, 2H), 3.10–3.22 (m, 2H).

$^{13}$C NMR (DMSO-d$_6$): 172.5, 171.6, 171.5, 171.3, 171.2, 171.1, 170.3, 149.7, 149.6, 149.5, 149.3, 148.3, 148.2, 147.7, 147.6, 147.4, 147.3, 147.2, 147.1, 109.1, 108.9, 108.2, 108.0, 107.0, 101.5, 101.3, 100.8, 100.3, 99.1, 99.0, 98.1, 75.0, 74.9, 74.7, 72.0, 71.9, 71.5, 71.4, 71.2, 70.8, 70.6, 70.5, 63.8, 63.6, 63.5, 63.4, 59.3, 59.0, 58.9, 58.3, 58.2, 57.6, 52.0, 51.8, 51.7, 48.1, 47.9.

EXAMPLE 44

5-Hydroxyacetamido-3-hydroxymethyl-N-methyl-N-(2,3-dihydroxy-propyl)-2,4,6-triiodobenzamide a. 5-Amino-3-acetoxymethyl-N-methyl-N-(2,3-dihydroxypropyl)-2,4,6-triiodo-benzamide 5-Amino-3-acetoxymethyl-2,4,6-triiodobenzoyl chloride was reacted with N-methyl-2,3-dihydroxypropanamine according to the conditions in Example 24g. The product was isolated in 97% yield.

$^1$H NMR (DMSO-d$_6$): 5.35 (s, 2H), 4.98 (br. s, 4H), 3.89 (m, 1H), 3.57–3.70 (m, 1H), 3.35–3.51 (m, 3H), 3.12–3.22 (m, 1H), 2.80 (s, 3H), 2.04 (s, 3H).

$^{13}$C NMR (DMSO-d$_6$): 170.7, 170.0, 148.6, 148.2, 140.0, 87.9, 81.6, 80.7, 76.8, 69.7, 66.4, 64.2, 50.2, 37.3, 20.4.

b. 5-Amino-3-acetoxymethyl-N-methyl-N-(2,3-diacetoxypropyl)-2,4,6-triiodobenzamide After acetylation of the compound of Example 44a according to the procedure of Example 24h the product was isolated in 93% yield.

MS (ESP, m/e): 758 ([M]+, 100%).

$^1$H NMR (DMSO-d$_6$): 5.49 (s, 2H), 5.41–5.49 (m, 1H), 5.10 (br. s, 2H), 4.49–4.57 (m, 1H), 4.20–4.30 (m, 1H), 4.03–4.15 (m, 1H), 3.38–3.52 (m, 1H), 2.94 (s, 3H), 2.10 (s, 9H).

c. 5-Acetoxyacetamido-3-acetoxymethyl-N-methyl-N-(2,3-diacetoxypropyl)-2,4,6-triiodobenzamide The compound of Example 44b was acylated according to the procedure of Example 24i, affording the product in 89% yield.

$^1$H NMR (CDCl$_3$): 9.11, 9.03 (2s, 1H), 5.53 (br. s, 2H), 5.40–5.51 (m, 1H), 4.80 (s, 2H), 4.45–4.56 (m, 1H), 3.95–4.30 (m, 2H), 3.33–3.53 (m, 1H), 2.92 (s, 3H), 2.25, 2.10, 2.09 (3s, 12 H).

$^{13}$C NMR (CDCl$_3$): 171.2, 170.5, 170.3, 170.0, 169.9, 169.7, 165.7, 143.0, 142.9, 142.8, 107.0, 97.7, 96.8, 96.4, 70.0, 63.6, 63.0, 48.3, 48.2, 37.8, 21.3, 21.2, 20.8, 20.7, 20.6.

d. 5-Hydroxyacetamido-3-hydroxymethyl-N-methyl-N-(2,3-dihydroxypropyl)-2,4,6-triiodobenzamide Deacetylation of the product of Example 44c according to the procedure of Example 24j, gave the product in 56% yield after preparative HPLC.

MS (ESP, m/e): 690 ([M]+, 100%).

$^1$H NMR (DMSO-d$_6$): 9.85, 9.77 (2s, 1H), 5.69 (t, 1H, J=5 Hz), 5.21 (t, 1H, J=5 Hz), 4.93 (d, 2H, J=2 Hz), 4.76 (d, 1H, J=5 Hz), 4.61 (t, 1H, J=5 Hz), 3.89, 4.00 (2d, 2H, J=5 Hz), 3.60–3.79 (m, 1H), 3.12–3.48 (m, 2H), 3.05, 2.82, 2.80 (3s, 3H).

$^{13}$C NMR (DMSO-d$_6$): 170.5, 170.4, 148.9, 146.5, 143.6, 106.8, 98.3, 96.9, 96.8, 74.5, 69.7, 64.2, 61.8, 50.2, 37.2.

EXAMPLE 45

5-[N'-(2-Hydroxyethyl)-hydroxyacetamido]-3-hydroxymethyl-N-methyl-N-(2,3-dihydroxypropyl)-2,4,6-triiodobenzamide a. 5-[N'-(2-Acetoxyethyl)-acetoxyacetamido]-3-acetoxymethyl-N-methyl-N-(2,3-diacetoxypropyl)-2,4,6-triiodobenzamide The alkylation of 5-acetoxyacetamido-3-acetoxymethyl-N-methyl-N-(2,3-diacetoxypropyl)-2,4,6-triiodobenzamide followed the procedure of Example 25a. The yield of isolated crude product was 96%.

MS (ESP, m/e): 944 ([M]+, 100,%).

$^1$H NMR (CDCl$_3$): 5.56 (br. s, 2H), 5.39–5.47 (m, 1H), 4.17–4.55 (m, 6H), 3.73–4.15 (m, 3H), 3.50 (t, 1H, J=6 Hz), 2.92, 2.95 (2s, 3H), 2.12, 2.11, 2.08, 1.97, 1.95 (5s, 15H).

$^{13}$C NMR (CDCl$_3$): 170.5, 170.3, 170.2, 170.1, 170.0, 166.4, 165.9, 151.0, 146.6, 144.5, 144.4, 144.3, 107.3, 98.9, 98.5, 98.3, 69.9, 69.8, 63.7, 63.4, 62.7, 62.1, 61.9, 61.4, 61.2, 48.8, 48.4, 47.9, 37.3, 28.6, 21.2, 20.9, 20.7, 20.5, 20.4.

b. 5-[N'-(2-Hydroxyethyl)-hydroxyacetamido]-3-hydroxymethyl-N-methyl-N-(2,3-dihydroxypropyl)-2,4,6-triiodobenzamide Hydrolysis of the compound of Example 45a according to the procedure of Example 25b, left the product in 40% yield after preparative HPLC.

MS (ESP, m/e): 734 ([M]+, 100%).

$^1$H NMR (DMSO-d$_6$): 5.23 (t, 1H, J=5 Hz), 4.91–5.03 (m, 3H), 4.58–4.82 (m, 3H), 3.84–3.94 (m, 1H), 3.40–3.72 (m, 9H), 3.00–3.24 (m, 1H), 3.07, 3.05, 2.81 (3s, 3H).

$^{13}$C NMR (DMSO-d$_6$): 170.9, 170.8, 170.2, 150.2, 150.1, 148.1, 148.0, 146.2, 146.1, 144.7, 107.8, 107.7, 99.6, 99.4, 98.9, 98.7, 74.6, 69.6, 64.2, 63.8, 61.5, 58.5, 58.4, 51.6, 51.1, 50.2, 37.2, 37.1.

EXAMPLE 46

5-(2,3-Dihydroxypropionylamino)-3-hydroxymethyl-N-methyl-N-(2,3-dihydroxypropyl)-2,4,6-triiodobenzamide a. 5-(2,2-Dimethyl-1,3-dioxolane-4-carbamido)-3-acetoxymethyl-N-methyl-N-(2,3-diacetoxypropyl)-2,4,6-triiodobenzamide 5-Amino-3-acetoxymethyl-N-methyl-N-(2,3-diacetoxypropyl)-2,4,6-triiodobenzamide was acylated according to the procedure in Example 29a. The crude product was isolated in 96% yield.

$^1$H NMR (CDCl$_3$): 8.46, 8.41, 8.24 (3s, 1H), 5.52 (s, 2H), 5.38–5.47 (m, 1H), 4.53–4.68 (m, 2H), 4.42–4.60 (m, 1H), 4.16–4.39 (m,2H,), 3.95–4.12 (m, 1H), 3.36–3.48 (m, 1H), 2.98 (s, 3H), 2.08, 2.06 (2s, 9H), 1.65, 1.63, 1.62, 1.55, 1.43, 1.36 (6s, 6H).

$^{13}$C NMR (CDCl$_3$): 170.7, 170.6, 170.5, 170.2, 170.0, 149.4, 142.9, 142.2, 111.7, 111.5, 105.9, 97.5, 97.2, 75.2, 73.8, 73.7, 72.8, 70.0, 67.1, 63.5, 62.6, 47.9, 30.0, 25.7, 21.4, 21.2, 20.7, 20.5.

b. 5-(2,3-Dihydroxypropionylamino)-3-hydroxymethyl-N-methyl-N-(2,3-dihydroxypropyl)-2,4,6-triiodobenzamide The hydrolysis and ketal cleavage of the compound of Example 46a were performed according to the procedure of Example 29b. The product was isolated in a yield of 30% after preparative HPLC.

MS (ESP, m/e): 719 ([M]+, 100%).

$^1$H NMR (DMSO-d$_6$): 9.84, 9.75 (2s, 1H), 5.84 (d, 1H, J=6 Hz), 5.20 (t, 2H, J=5 Hz), 4.93 (d, 2H, J=5 Hz), 4.74–4.86 (m, 2H), 4.60 (t, 1H, J=6 Hz), 4.00–4.35 (m, 2H), 3.84–3.93 (m, 1H), 3.73–3.82 (m, 1H), 3.51–3.68 (m, 2H), 3.40–3.48 (m, 1H), 3.09–3.23 (m, 2H), 2.80 (br. s, 3H).

$^{13}$C NMR (DMSO-d$_6$): 172.7, 170.5, 148.8, 146.5, 144.7, 143.7, 106.8, 106.6, 98.2, 96.8, 96.7, 74.5, 73.8, 72.0, 69.7, 64.2, 63.9, 63.7, 50.2, 37.2.

EXAMPLE 47

5-[N'-(2-Hydroxyethyl)-2,3-dihydroxypropionylamino]-3-hydroxymethyl-N-methyl-N-(2,3-dihydroxypropyl)-2,4,6-triiodobenzamide a. 5-[N'-(2-Acetoxyethyl)-2,2-dimethyl-1,3-dioxolane-4-carbamido]-3-acetoxymethyl-N-methyl-N-(2,3-dihydroxypropyl)-2,4,6-triiodobenzamide 5-(2,2-dimethyl-1,3-dioxolane-4-carbamido)-3-acetoxymethyl-N-methyl-N-(2,3-diacetoxypropyl)-2,4,6-triiodobenzamide was alkylated according to the conditions in Example 30a. The crude product was isolated in a yield of 88%.

MS (ESP, m/e): 971 ([M]+, 100%).

$^1$H NMR (CDCl$_3$): 5.54 (br. s, 2H), 5.38–5.45 (m, 1H), 3.98–4.54 (m, 10H), 3.30–3.52 (m, 1H), 2.94, 2.88 (2s, 3H), 2.06, 2.05 (2 br s, 9H), 1.60, 1.46, 1.43, 1.37, 1.30 (5s, 6H).

$^{13}$C NMR (CDCl$_3$): 170.4, 170.3, 170.1, 170.0, 150.6, 150.3, 147.8, 143.7, 143.3, 111.5, 111.4, 110.9, 99.1, 98.7, 97.8, 96.7, 75.4, 73.8, 69.9, 67.9, 67.2, 63.7, 63.4, 62.8, 62.1, 61.8, 61.4, 48.7, 47.9, 37.3, 28.6, 26.5, 25.6, 25.4, 21.2, 20.9, 20.5, 20.4.

b. 5-[N'-(2-Hydroxyethyl)-2,3-dihydroxypropionylamino]-3-hydroxymethyl-N-methyl-N-(2,3-dihydroxypropyl)-2,4,6-triiodobenzamide Hydrolysis and ketal cleavage of the compound of Example 47a according to the procedure of Example 30b, followed by preparative HPLC afforded the product in a yield of 20%.

MS (ESP, m/e): 763 ([M]+, 100%).

$^1$H NMR (DMSO-d$_6$): 5.18 (br. s, 1H), 4.95 (d, 2H, J=4 Hz), 4.71 (br. s, 1H), 4.42–4.50 (m, 1H), 4.12 (br. s, 1H), 3.90 (br. s, 2H), 3.08–3.76 (m, 12H,), 2.80 (s, 3H).

$^{13}$C NMR (DMSO-d$_6$): 171.6, 171.5, 171.3, 171.2, 171.0, 170.4, 167.7, 150.0, 149.9, 149.8, 148.2, 147.7, 147.6, 147.4, 147.3, 147.2, 147.1, 144.7, 109.0, 108.8, 108.1, 107.8, 106.6, 100.7, 99.6, 99.5, 98.3, 98.2, 97.4, 97.3, 74.9, 74.7, 74.6, 74.5, 72.0, 71.8, 71.6, 71.4, 71.2, 71.0, 70.8, 70.7, 70.6, 69.6, 64.2, 63.7, 63.5, 59.3, 58.3, 58.2, 51.9, 51.8, 51.7, 51.4, 50.3, 37.2.

EXAMPLE 48

5-Hydroxyacetamido-3-hydroxymethyl-N-(1,3-dihydroxyprop-2-yl)-2,4,6-triiodobenzamide a. 5-Amino-3-acetoxymethyl-N-(1,3-dihydroxyprop-2-yl)-2,4,6-triiodobenzamide 5-Amino-3-acetoxymethyl-2,4,6-triiodobenzoyl chloride was reacted with serinol according to the conditions in Example 24g. The product was isolated in 95% yield.

$^1$H NMR (DMSO-d$_6$): 8.12 (d, 1H, J=7 Hz), 5.38 (s, 2H), 4.76 (br. s, 4H), 3.82 (m, 1H), 3.60–3.68 (m, 2H), 3.47–3.57 (m, 2H), 2.04 (s, 3H).

$^{13}$C NMR (DMSO-d$_6$): 170.0, 169.8, 149.5, 148.2, 139.4, 87.6, 82.3, 81.7, 77.0, 66.4, 59.3, 53.1, 20.4.

b. 5-Amino-3-acetoxymethyl-N-(1,3-diacetoxyprop-2-yl)-2,4,6-triiodobenzamide

Acetylation of the compound of Example 48a was performed smoothly accoding to the conditions given in Example 24h. The product was isolated, after purification, in 98% yield.

MS (ESP, m/e): 744 ([M]+, 100%).

$^1$H NMR (CDCl$_3$): 6.17 (d, 1H, J=7 Hz), 5.50 (s, 2H), 4.61–4.69 (m, 1H), 4.24 (m, 4H), 2.21, 2.11, 2.08 (3s, 9H).

$^{13}$C NMR (CDCl$_3$): 170.8, 170.4, 169.8, 148.4, 147.8, 140.9, 87.8, 81.0, 79.6, 62.3, 47.9, 22.1, 20.9, 20.6, 20.5.

c. 5-Acetoxyacetamido-3-acetoxymethyl-N-(1,3-diacetoxyprop-2-yl)-2,4,6-triiodobenzamide Acylation of the compound of Example 48b was effected according to the method in Example 24i. The product was isolated in 92% yield.

MS (ESP, m/e): 844 ([M]+, 100%).

$^1$H NMR (DMSO-d$_6$): 8.49, 8.47 (2s, 1H), 5.48 (s, 2H), 5.22 (d, 1H, J=6 Hz), 4.70 (s, 2H), 4.45–4.53 (m, 1H), 4.16–4.25 (m, 4H), 2.00, 1.98 (2s, 12H).

$^{13}$C NMR (CDCl$_3$): 170.9, 170.5, 170.1, 167.1, 149.8, 142.4, 142.1, 106.0, 97.7, 97.0, 62.6, 62.1, 62.0, 49.4, 49.1, 48.8, 48.5, 48.3, 47.3, 20.6, 20.3.

d. 5-Hydroxyacetamido-3-hydroxymethyl-N-(1,3-dihydroxyprop-2-yl)-2,4,6-triiodobenzamide Hydrolysis of the compound of Example 48c according to the procedure of Example 24j afforded a yield of 55% after HPLC purification.

MS (ESP, m/e): 676 ([M]+, 100%).

EXAMPLE 49

5-[N'-(2-Hydroxyethyl)-hydroxyacetamido]-3-hydroxymethyl-N-(1,3-dihydroxyprop-2-yl)-2,4,6-triiodobenzamide a. 5-[N'-(2-Acetoxyethyl)-acetoxyacetamido]-3-acetoxymethyl-N-(1,3-diacetoxyprop-2-yl)-2,4,6-triiodobenzamide Alkylation of the compound of Example 48c with 2-bromoethyl acetate was performed according to the procedure of Example 25a. The product was isolated in 86% yield.

MS (ESP, m/e): 924 ([M]+, 100%).

$^1$H NMR (CDCl$_3$): 6.58 (d, 1H, J=5 Hz), 5.52 (s, 2H), 4.52–4.65 (m, 1H), 4.18–4.38 (m, 7H), 3.73–3.95 (m, 2H), 3.55 (t, 1H, J=5 Hz), 2.07, 2.04 (2s, 15H).

$^{13}$C NMR (DMSO-d$_3$): 170.8, 170.6, 170.4, 170.2, 169.9, 166.0, 151.1, 146.5, 145.9, 144.0, 108.0, 107.9, 99.9, 99.3, 98.8, 98.5, 63.6, 62.6, 62.0, 61.7, 60.9, 48.7, 48.2, 47.9, 47.7, 28.6, 20.8, 20.7, 20.6, 20.4.

b. 5-[N'-(2-Hydroxyethyl)-hydroxyacetamido]-3-hydroxymethyl-N-(1,3-dihydroxyprop-2-yl)-2,4,6-triiodobenzamide Hydrolysis of the compound of Example 49a according to the method of Example 25b, gave, after HPLC purification, an isolated yield of 26%.

MS (ESP, m/e): 743 ([M]+, 100%).

EXAMPLE 50

5-(2,3-Dihydroxypropionylamino)-3-hydroxymethyl-N-(1,3-dihydroxyprop-2-yl)-2,4,6-triiodobenzamide a. 5-(2,2-Dimethyl-1,3-dioxolane-4-carboxamido)-3-acetoxymethyl-N-(1,3-diacetoxyprop-2-yl)-2,4,6-triiodobenzamide 5-Amino-3-acetoxymethyl-N-(1,3-diacetoxyprop-2-yl)-2,4,6-triiodobenzamide was acylated according to the procedure in Example 29a. The crude product could be isolated in 94% yield.

$^1$H NMR (CDCl$_3$): 8.39, 8.47 (2s, 1H), 6.63–6.76 (m, 1H), 5.55 (s, 2H), 4.54–4.68 (m, 2H), 4.18–4.40 (m, 6H), 2.08, 2.05 (2s, 9H), 1,66, 1.64, 1.55, 1.44, 1.37 (5s, 6H).

$^{13}$C NMR (CDCl$_3$): 170.7, 170.6, 170.5, 169.6, 169.1, 149.0, 142.8, 142.0, 111.7, 111–5, 106.4, 106.2, 97.6, 97.3, 75.2, 73.8, 73.7, 72.8, 67.1, 26.9, 25.7, 25.4, 21.4, 20.8, 20.5.

b. 5-(2,3-Dihydroxypropionylamino)-3-hydroxymethyl-N-(1,3-dihydroxyprop-2-yl)-2,4,6-triiodobenzamide Hydrolysis and ketal cleavage of the compound of Example 50a were performed according to the procedure of Example 29b. After preparative HPLC the product was isolated in 33% yield.

MS (ESP, m/e): 705 ([M]+, 100%).

EXAMPLE 51

5-[N'-(2-Hydroxyethyl)-2,3-dihydroxypropionylamino]-3-hydroxymethyl-N-(1,3-dihydroxyprop-2-yl)-2,4,6-triiodobenzamide a. 5-[N'-(2-Acetoxyethyl)-2,2-dimethyl-1,3-dioxolane-4-carboxamido]-3-acetoxymethyl-N-(1,3-diacetoxyprop-2-yl)-2,4,6-triiodobenzamide The alkylation of 5-(2,2-dimethyl-1,3-dioxolane-4-carboxamido)-3-acetoxymethyl-N-(1,3-diacetoxyprop-2-yl)-2,4,6-triiodobenzamide with 2-bromoethyl acetate was performed according to the procedure of Example 30a. The crude product was isolated in 83% yield.

MS (ESP, m/e): 958 ([M]+, 100%)

$^1$H NMR (CDCl$_3$) 6.71 (d,1H, J=5 Hz), 5.51 (s, 2H), 4.52–4.59 (m, 2H), 3.76–4.36 (m, 9H), 3.46 (t, 1H, J=6 Hz), 2.10, 2.04, 2.00 (3s, 12H), 1.58, 1.44, 1.40, 1.34 (4s, 6H).

$^{13}$C NMR (CDCl$_3$): 170.6, 170.4, 170.1, 169.9, 169.1, 150.8, 150.5, 143.7, 143.6, 143.4, 142.7, 142.0, 111.7, 111.3, 111.1, 110.9, 97.7, 97.2, 75.1, 73.8, 67.9, 67.1, 63.7, 62.8, 62.1, 61.7, 61.0, 49.1, 47.9, 47.5, 30.7, 28.6, 26.4, 25.9, 25.6, 25.5, 24.8, 20.8, 20.7, 20.5.

b. 5-[N'-(2-Hydroxyethyl)-2,3-dihydroxypropionylamino]-3-hydroxymethyl-N-(1,3-dihydroxyprop-2-yl)-2,4,6-triiodobenzamide Hydrolysis and ketal cleavage of the product of Example 51a were performed according to the procedure of Example 30b. After preparative HPLC the product was isolated in 25% yield.

MS (ESP, m/e): 750 ([M]+, 100%).

EXAMPLE 52

5-(2,3-Dihydroxypropionylamino)-3-hydroxymethyl-N-(2-hydroxyethyl)-2,4,6-triiodobenzamide a. 5-Amino-3-acetoxymethyl-N-(2-hydroxyethyl)-2,4,6-triiodobenzamide 5-Amino-3-acetoxymethyl-2,4,6-triiodobenzoyl chloride was reacted with ethanolamine according to the general procedure in Example 24g. The yield of isolated product was 98%.

$^1$H NMR (DMSO-d$_6$): 8.41 (t, 1H, J=6 Hz), 5.45 (br. s, 2H), 5.38 (s, 2H), 3.51–3.57 (m, 2H), 3.40 (s, 1H), 3.21–3.29 (m, 2H), 2.04 (s, 3H).

b. 5-Amino-3-acetoxymethyl-N-(2-acetoxyethyl)-2,4,6-triiodobenzamide

Acetylation of the compound of Example 52a was performed according to the method of Example 24h. The product, after purification, was isolated in 97% yield.

$^1$H NMR (CDCl$_3$): 7.81 (t, 1H, J=6 Hz), 5.14 (s, 2H), 3.92 (t, 2H, J=6 Hz), 3.27 (m, 2H), 2.85–3.36 (br. s, 2H), 1.74, 1.72 (2s, 6 H).

$^{13}$C NMR (CDCl$_3$): 169.9, 169.3, 149.3, 148.9, 147.1, 139.4, 136.0, 86.1, 80.5, 79.5, 61.4, 37.7, 20.2, 19.8.

c. 5-(2,2-Dimethyl-1,3-dioxolane-4-carboxamido)-3-acetoxymethyl-N-(2-acetoxyethyl)-2,4,6-triiodobenzamide The general acylation method in Example 29a was followed for the compound of Example 52b. The resultant product was isolated in 97% yield.

$^1$H NMR (CDCl$_3$): 8.43, 8.39, 8.29 (3s, 1H), 6.55–6.64 (m, 1H), 5.56 (s, 2H), 4.54–4.70 (m, 2H), 4.24–4.36 (m, 3H), 3.66–3.76 (m, 2H), 2.08, 2.03 (2s, 6H), 1.67, 1.64, 1.57, 1.56, 1.47, 1.45 (6s, 6H).

$^{13}$C NMR (CDCl$_3$): 171.1, 170.9, 169.7, 169.3, 156.2, 150.4, 150.2, 142.9, 142.0, 141.6, 112.0, 111.8, 111.6, 97.8, 97.5, 75.3, 73.8, 72.9, 72.8, 72.6, 72.5, 67.2, 64.7, 64.4, 62.7, 62.5, 38.9, 30.9, 26.8, 26.5, 25.7, 25.5, 21.0, 20.6.

d. 5-(2,3-Dihydroxypropionylamino)-3-hydroxymethyl-N-(2-hydroxyethyl)-2,4,6-triiodobenzamide Hydrolysis and ketal cleavage of the product of Example 52c were performed according to the procedure of Example 29b. After preparative HPLC the product was isolated in 50% yield.

MS (ESP, m/e): 675 ([M]+, 100%).

$^1$H NMR (DMSO-d$_6$): 9.79, 9.77 (2s, 1H), 8.38–8.54 (m, 1H), 5.80 (s, 1H), 5.18 (br. s, 1H), 4.95 (s, 2H), 4.81 (br. s, 1H), 4.65 (br. s, 1H), 4.05 (s, 1H), 3.84 (d, 1H, J=8 Hz), 3.50–3.62 (m, 3H,), 3.20–3.32 (m, 2H).

$^{13}$C NMR (DMSO-d$_6$): 170.5, 170.4, 170.0, 150.3, 146.0, 143.3, 143.1, 106.7, 106.5, 106.4, 98.7, 98.5, 97.4, 97.2, 74.6, 73.8, 72.1, 64.2, 63.6, 59.2, 41.7.

EXAMPLE 53

5-[N'-(2-Hydroxyethyl)-2,3-dihydroxypropionylamino]-3-hydroxymethyl-N-(2-hydroxyethyl)-2,4,6-triiodobenzamide a. 5-[N'-(2-Acetoxyethyl)-2,2-dimethyl-1,3-dioxolane-4-carboxamido]-3-acetoxymethyl-N-(2-acetoxyethyl)-2,4,6-triiodobenzamide The alkylation procedure with 2-bromoethyl acetate given in Example 30a was followed for the product of Example 52c to give 89% yield of the product.

$^1$H NMR (CDCl$_3$): 6.35–6.82 (m, 1H), 5.56 (s, 2H), 4.55–4.70 (m, 1H), 4.04–4.40 (m, 6H), 3.68–3.77 (m, 2H), 3.45–3.53 (t, 2H, J=6 Hz), 2.09, 2.07, 2.05 (3s, 9H), 1.66, 1.65, 1.62, 1.49, 1.46, 1.45, 1.39 (7s, 6H).

$^{13}$C NMR (CDCl$_3$): 170.9, 170.3, 169.7, 149.9, 144.0, 142.9, 142.4, 111.9, 111.4, 106.1, 97.7, 97.5, 91.7, 75.2, 74.0, 72.9, 72.6, 67.2, 64.1, 63.8, 63.6, 62.9, 62.6, 62.5, 61.8, 61.4, 61.2, 49.5, 48.0, 39.1, 38.9, 30.9, 28.6, 28.3, 26.8, 26.4, 26.2, 25.4, 21.2, 20.6.

b. 5-[N'-(2-Hydroxyethyl)-2,3-dihydroxypropionylamino]-3-hydroxymethyl-N-(2-hydroxyethyl)-2,4,6-triiodobenzamide Hydrolysis and ketal cleavage of the compound of Example 53a were performed according to the procedure of Example 30b. Isolated yield, after preparative HPLC was 22%.

MS (ESP, m/e): 720 ([M]$^+$, 100%).

EXAMPLE 54

5-Hydroxyacetamido-3-hydroxymethyl-N-[tris-(hydroxymethyl)-methyl]-2,4,6-triiodobenzamide a. 5-Amino-3-acetoxymethyl-N-[tris-(hydroxymethyl)-methyl]-2,4,6-triiodobenzamide 5-Amino-3-acetoxymethyl-2,4,6-triiodobenzoyl chloride (9.0 g, 14.9 mmol) and sodium carbonate (1.58 g, 14.9 mmol) were mixed in dry dioxane (30 ml). Tris-(hydroxymethyl)aminomethane (1.81 g, 14.9 mmol) was added and the mixture was refluxed for 4.5 days. The reaction mixture was worked up as described in Example 24g. A product mixture mainly consisting of two products was isolated, and separated by preparative HPLC.

5-Amino-3-acetoxymethyl-N-[tris-(hydroxymethyl)-methyl]-2,4,6-triiodobenzamide was isolated in a yield of 2.0 g (20%).

$^1$H NMR (DMSO-d$_6$): 7.80, 7.65 (2s, 1H), 5.37 (s, 2H), 3.45–4.08 (m, 11H), 2.04 (s, 3H).

5-Amino-3-hydroxymethyl-N-[tris-(hydroxymethyl)-methyl]-2,4,6-triiodobenzamide was isolated in a yield of 2.1 g.

$^1$H NMR (DMSO-d$_6$): 7.67 (br. s, 1H), 4.87 (s, 2H), 4.42 (br. s, 2H), 4.15 (s, 4H), 3.69 (s, 6H).

b. 5-Amino-3-acetoxymethyl-N-[tris-(acetoxymethyl)-methyl]-2,4,6-triiodobenzamide The two products of Example 54a were acetylated as described in Example 24h. The acetylated products were isolated in yields of 81% and 74% respectively.

$^1$H NMR (CDCl$_3$): 6.18, 5.92 (2s, 1H), 5.50 (s, 2H), 5.12 (br. s, 2H), 4.50 (br. s, 6H), 2.06 (s, 12H).

c. 5-Acetoxyacetamido-3-acetoxymethyl-N-[tris-(acetoxymethyl)-methyl]-2,4,6-triiodobenzamide Acylation of the product of Example 54b with acetoxyacetyl chloride was performed according to the procedure of Example 24i. The isolated yield was 97%.

MS (ESP, m/e): 916 ([M]$^+$, 100%).

$^1$H NMR (CDCl$_3$): 8.74 (s, 1H), 6.58 (s, 1H), 5.55 (s, 2H), 4.76 (s, 2H), 4.58 (br. s, 6H), 2.08, 2.05 (2s, 15H).

$^{13}$C NMR (CDCl$_3$): 170.3, 170.2, 169.6, 165.9, 149.9, 149.3, 143.0, 142.5, 136.6, 107.5, 97.9, 97.3, 63.1, 62.6, 62.3, 58.9, 21.3, 21.0, 20.8.

d. 5-Hydroxyacetamido-3-hydroxymethyl-N-[tris-(hydroxymethyl)-methyl]-2,4,6-triiodobenzamide After hydrolysis of the compound of Example 54c, according to the procedure of Example 24j, and HPLC purification the product was isolated in 73% yield.

MS (ESP, m/e): 706 ([M]$^+$, 100%), 728 ([M+Na]$^+$, 19%).

EXAMPLE 55

5-[N'-(2-Hydroxyethyl)-hydroxyacetamido]-3-hydroxymethyl-N-[tris-(hydroxymethyl)-methyl]-2,4,6-triiodobenzamide a. 5-[N'-(2-Acetoxyethyl)-acetoxyacetamido]-3-acetoxymethyl-N-[tris-(acetoxymethyl)-methyl]-2,4,6-triiodobenzamide Alkylation of the product of Example 54c was performed according to the procedure of Example 25a. The yield of crude product was 98%.

MS (ESP, m/e): 997 ([M]$^+$, 100%), 1131 ([M+Cs]$^+$, 15%).

$^1$H NMR (CDCl$_3$): 6.54, 6.35, 6.25 (3s, 1H), 5.57 (br. s, 2H), 4.77, 4.72, 4.62, 4.58, 4.56, 4.53, 4.42 (7s, 8H), 4.28–4.38 (m, 2H), 3.45–4.26 (m, 2H), 2.13, 2.11, 2.09, 2.07, 1.95, 1.90 (6s, 18H).

$^{13}$C NMR (CDCl$_3$): 170.8, 170.6, 170.5, 170.3, 170.2, 170.1, 170.0, 168.7, 166.3, 166.1, 151.0, 146.8, 146.1, 144.3, 108.3, 108.1, 99.9, 99.4, 98.8, 98.5, 62.7, 62.5, 62.1, 61.8, 61.0, 59.7, 59.3, 58.9, 48.8, 47.6, 21.0, 20.9, 20.8, 20.7, 20.5.

b. 5-[N'-(2-Hydroxyethyl)-hydroxyacetamido]-3-hydroxymethyl-N-[tris-(hydroxymethyl)-methyl]-2,4,6-triiodobenzamide Hydrolysis of the product of Example 55a was performed according to the procedure of Example 25b. After HPLC purification the compound was isolated in 67% yield.

MS (ESP, m/e): 750 ([M]$^+$, 100%).

EXAMPLE 56

5-(2,3-Dihydroxypropionylamino)-3-hydroxymethyl-N-[tris-(hydroxymethyl)-methyl]-2,4,6-triiodobenzamide a. 5-(2,2-Dimethyl-1,3-dioxolane-4-carbamido)-3-acetoxymethyl-N-[tris-(acetoxymethyl)-methyl]-2,4,6-triiodobenzamide 5-Amino-3-acetoxymethyl-N-[tris-(acetoxymethyl)-methyl]-2,4,6-triiodobenzamide was acylated according to the general method in Example 29a. The product was isolated in 81% yield.

MS (ESP, m/e): 944 ([M]$^+$, 100%).

$^1$H NMR (CDCl$_3$): 9.07, 8.75, 8.40, 8.38, 8.30 (5s, 1H), 6.37, 6.28, 5.94 (3s, 1H), 5.55 (br. s, 2H), 3.96–4.65 (m, 9H), 2.09 (br. s, 12H), 1.64, 1.62, 1.48, 1.47 (4s, 6H).

$^{13}$C NMR (CDCl$_3$): 170.6, 170.4, 170.3, 170.2, 170.1, 169.6, 143.8, 142.8, 142.5, 142.2, 136.5, 111.9, 111.6, 111.4, 98.4, 97.6, 97.1, 75.1, 73.8, 73.7, 72.8, 72.7, 72.5, 72.4, 67.0, 64.2, 62.6, 62.5, 62.2, 62.0, 26.7, 26.4, 26.0, 25.6, 25.4, 25.3, 20.8, 20.7, 20.4.

b. 5-(2,3-Dihydroxypropionylamino)-3-hydroxymethyl-N-[tris-(hydroxymethyl)-methyl]-2,4,6-triiodobenzamide Hydrolysis and ketal cleavage of the product of Example 56a were performed according to the procedure of Example 29b. After preparative HPLC the product was isolated in 27% yield.

MS (ESP, m/e): 736 ([M]$^+$, 100%).

EXAMPLE 57

5-[N'-(2-Hydroxyethyl)-2,3-dihydroxypropionylamino]-3-hydroxymethyl-N-[tris-(hydroxymethyl)-methyl]-2,4,6-triiodobenzamide a. 5-[N'-(2-Acetoxyethyl)-2,2-dimethyl-1,3-dioxolane-4-carbamido]-3-acetoxymethyl-N-[tris-(acetoxymethyl)-methyl]-2,4,6-triiodobenzamide The alkylation of the product of Example 56a with 2-bromoethyl acetate followed the procedure of Example 30a. The product could be isolated in 75% yield.

MS (ESP, m/e): 1024 ([M]$^+$, 100%).

$^1$H NMR (CD$_3$OD): 5.66, 5.64, 5.62 (3 br s, 1H), 4.61–4.67 (m, 1H), 4.60 (s, 2H), 4.20–4.39 (m, 7H), 4.05–4.13 (m, 1H), 3.57–3.78 (m, 2H), 3.29–3.32 (m, 2H), 2.15, 2.08, 2.07, 2.04, 1.96 (5s, 15H), 1.62, 1.59, 1.58, 1.44, 1.42, 1.36, 1.30 (7s, 6H).

$^{13}$C NMR (CDCl$_3$): 170.8, 170.4, 170.3, 170.1, 149.7, 148.2, 147.6, 143.3, 140.4, 111.1, 98.3, 98.2, 97.7, 73.6, 72.7, 71.5, 66.9, 65.7, 63.8, 63.5, 62.9, 62.6, 62.4, 62.2, 61.9, 61.6, 30.5, 28.4, 26.4, 26.3, 25.8, 25.5, 25.2, 24.5, 20.6, 20.4, 20.2.

b. 5-[N'-(2-Hydroxyethyl)-2,3-dihydroxypropionylamino]-3-hydroxymethyl-N-[tris-(hydroxymethyl)-methyl]-2,4,6-triiodobenzamide Hydrolysis and ketal cleavage of the product of Example 57a were performed according to the general method in Example 30b. After preparative HPLC the product was isolated in 15% yield.

MS (ESP, m/e): 779 ([M]$^+$, 100%).

EXAMPLE 58

5-(2,3-Dihydroxypropionylamino)-2,4,6-triiododibenzyl alcohol a. 5-Nitro-1,3-dibenzyl alcohol 5-Nitro-isophthalic acid (10.5 g, 49.7 mmol) was dissolved in 250 ml tetrahydrofuran. Under inert atmosphere, boron trifluoride diethyl etherate (28.2 g, 0.199 mol) was added. With efficient stirring sodium borohydride (5.07 g, 0.134 mol) was added portionwise during 1 h. The procedure of Example 24a was followed. Yield: 8.4 g (92%) of a white crystalline solid.

$^1$H NMR (CD$_3$COCD$_3$): 8.11 (d, 2H, J=3 Hz), 7.75 (t, 1H, J=3 Hz), 4.75 (s, 4H), 4.64 (br. s, 2H).

b. 5-Amino-1,3-dibenzyl alcohol

5-Nitro-dibenzyl alcohol (8.4 g, 45.7 mmol) was dissolved in methanol (70 ml), and hydrogenated according to Example 24c. The yield was 7.8 g (90%).

$^1$H NMR (DMSO-d$_6$): 9.60–10.80 (br. s, 2H), 7.23 (t, 1H, J=2 Hz), 7.18 (d, 2H, J=3 Hz), 4.49 (s, 4H), 3.95 (br. s, 3H).

c. 5-Amino-2,4,6-triiodo-dibenzyl alcohol

Iodine (5.3 g, 20.8 mmol) was dissolved in in a mixture of water and methanol (1:3, 325 ml), which had been made 0.2 M with respect to sodium tetrafluoroborate. The pH of this solution was adjusted to 1.5 with tetrafluoroboric acid. This solution was used as anolyte, and the solution without iodine as the catolyte in an electrolysis cell, where anode and cathode volumes were separated by a fritted glass disk. Current 0.6 A, a charge of 3 F/mol iodine was passed through the solution. The solution was used immediately for iodination. 5-Amino-1,3-dibenzyl alcohol (1.3 g, 6.33 mmol) was dissolved in water (15 ml), and to this solution was added the electrolysis mixture above. The mixture was stirred at 60° C. for 28 h. After cooling to room temperature, a 10% aqueous solution of sodium hydrogen sulphite (3 ml) was added. The mixture was neutralised with aqueous sodium hydroxide, and the methanol was evaporated. A brown precipitate was formed and filtered off. The filtercake was boiled two times with 80 ml of water and filtered, then dried. The product (2.0 g, 59%) was a grey crystalline residue.

$^1$H NMR (DMSO-d$_6$): 5.10–5.58 (br. s, 2H), 4.98 (s, 4H), 3.50 (br s, 2H).

$^{13}$C NMR (DMSO-d$_6$): 147.9, 144.7, 89.9, 87.5, 75.5.

d. 5-Amino-2,4,6-triiodo-1,3-diacetoxymethylbenzene

5-Amino-2,4,6-triodo-dibenzyl alcohol was acetylated according to the method in Example 24e. After workup the product was chromatographed on a column of alumina using methylene chloride/ethyl acetate (5/1) as the eluent. A white crystalline product was isolated in 78% yield.

$^1$H NMR (CDCl$_3$): 5.63 (s,4H), 5.24 (br. s, 2H), 2.13 (s, 6H).

$^{13}$C NMR (CDCl$_3$): 170.5, 147.8, 140.8, 90.5, 88.4, 78.4, 20.7.

e. 5-(2,2-Dimethyl-1,3-dioxolane-4-carbamido)-2,4,6-triiodo-1,3-diacetoxymethyl-benzene 5-Amino-2,4,6-triiodo-1,3-diacetoxymethylbenzene was acylated according to the procedure in Example 29a. A white crystalline product was formed in 83% yield, after filtration through a pad of alumina with methylene chloride/ethyl acetate (1/1) as eluent.

$^1$H NMR (DMSO-d$_6$): 10.04 (s, 1H), 5.55 (s, 4H), 5.02–5.08 (m, 1H), 4.554–4.80 (m, 1H), 4.05–4.34 (m, 1H), 2.06 (s, 6H), 1.56, 1.54, 1.37, 1.28 (4s, 6H).

$^{13}$C NMR (CDCl$_3$): 170.4, 170.3, 169.3, 143.1, 142.8, 141.9, 111.7, 106.5, 106.4, 105.7, 78.2, 75.3, 67.2, 26.5, 24.9, 20.6.

f. 5-(2,3-Dihydroxypropionylamino)-2,4,6-triiodo-1,3-dibenzyl alcohol

Hydrolysis and ketal cleavage of the product of Example 58e were performed according to the procedure of Example 29b. After preparative HPLC the product was isolated in 43%.

MS (ESP, m/e): 620 ([M]$^+$, 100%).

EXAMPLE 59

5-[N-(2-Hydroxyethyl)-2,3-dihydroxypropionylamino]-2,4,6-triiodo-1,3-dibenzyl alcohol a. 5-[N-(2-Acetoxyethyl)-2,2-dimethyl-1,3-dioxolane-4-carbamido]-2,4,6-triiodo-1,3-diacetoxymethylbenzene 5-(2,2-Dimethyl-1,3-dioxolane-4-carbamido)-2,4,6-triiodo-1,3-di-(acetoxymethyl) benzene was alkylated with 2-bromoethyl acetate according to Example 30a. The crude product, containing some O-alkylated material was used directly in next step.

MS (ESP, m/e): 830 ([M]$^+$, 100%), 962 ([M+Cs]$^+$, 25%).

b. 5-[N-(2-Hydroxyethyl)-2,3-dihydroxypropionylamino]-2,4,6-triiodo-1,3-dibenzyl-alcohol Hydrolysis and ketal cleavage of the product of Example 59a were performed according to the procedure of Example 30b. The product was isolated in 39% yield after preparative HPLC.

MS (ESP, m/e): 663 ([M]$^+$, 100%).

EXAMPLE 60

5-(2,3,4-Trihydroxybutanoylamino)-2,4,6-triiodo-1,3-dibenzyl alcohol a. 5-(2,3,4-Triacetoxybutanoylamino)-2,4,6-triiodo-1,3-di-(acetoxymethyl)-benzene 5-Amino-2,4,6-triiodo-1,3-di-(acetoxymethyl)benzene (2.0 g, 3.25 mmol) was dissolved in dimethylacetamide (4 ml) at room temperature. 2,3,4-Triacetoxybutyryl chloride (7.4 g, 26.4 mmol) was added and the mixture was stirred for 20 h. The work up was carried out as in Example 24i. A white crystalline product 2.2 g (79%), was isolated.

MS (ESP, m/e): 857 ([M]$^+$, 100%), 880 ([M+Na]$^+$, 20%).

$^1$H NMR (CDCl$_3$): 7.93 (s, 1H), 5.68–5.79 (m, 1H), 5.66, 5.61 (2s, 4H), 4.39–4.55 (m, 2H), 4.16–4.23 (m, 1H), 2.20, 2.17, 2.13, 2.11, 2.10 (5s, 15H).

$^{13}$C NMR (CDCl$_3$): 170.4, 170.2, 169.8, 169.5, 169.2, 169.1, 146.1, 143.0, 142.9, 141.4, 106.5, 106.1, 105.8, 78.2, 71.5, 69.6, 69.4, 69.0, 67.1, 61.3, 21.2, 21.0, 20.8, 20.7, 20.6, 20.5, 20.2.

b. 5-(2,3,4-Trihydroxybutanoylamino)-2,4,6-triiodo-1,3-dibenzyl alcohol

The hydrolysis of the product of Example 60a was performed according to the method of Example 24j, and HPLC purification gave the product in 44% yield.

MS (ESP, m/e): 649 ([M]$^+$, 100%).

EXAMPLE 61

3,5-Bis(2,3-dihydroxypropionylamino)-2,4,6-triiodo-(2-hydroxyethyl)benzene a. 3,5-Dinitro-(2-hydroxyethyl)benzene 3,5-Dinitrostyrene (0.28 g, 1.43 mmol) was dissolved in acetonitrile (150 ml) and water (300 ml) was added. The mixture was poured into a photolysis apparatus and irradiated with an UV-lamp (HPK 125, Phillips) for 3 h. The organic solvent was evaporated and the aqueous phase extracted with methylene chloride (2×100 ml). The solvent was evaporated and the residue was purified by flash chromatography on a column of silica using heptane/ethyl acetate (1/1) as eluent. Evaporation of solvent gave 76 mg (25%) of a crystalline product.

$^1$H NMR (CDCl$_3$): 8.93 (t, 1H, J=3 Hz), 8.48 (d, 2H, J=3 Hz), 4.02 (q, 2H, J=6 Hz), 3.10 (t, 2H, J=6 Hz).

$^{13}$C NMR (CDCl$_3$): 148.4, 143.7, 129.4, 117.0, 62.1, 38.2.

b. 3,5-Diamino-(2-hydroxyethyl)benzene 3,5-Dinitro-(2-hydroxyethyl)benzene (0.18 g, 0.85 mmol) was dissolved in methanol (50 ml) and hydrogenated over Pd/C (10%) in a Parr apparatus at 60 psi. After complete hydrogen uptake the catalyst was filtered off and the solvent was evaporated which gave a solid residue of 0.10 g (81%).

$^1$H NMR (CD$_3$OD): 6.06 (s, 3H), 3.70 (t, 2H, J=7 Hz), 2.64 (t, 2H, J=7 Hz).

c. 3,5-Diamino-2,4,6-triiodo-(2-hydroxyethyl)benzene 3,5-Diamino-(2-hydroxyethyl)benzene (0.18 g, 1.16 mmol) was dissolved in methanol (50 m) and water (4 ml). Hydrochloric acid (1M, 1.3 ml) was added followed by a 70% w/w solution of potassium iododichloride (0.86 g, 3.63 mmol). A precepitate formed immediately and stirring was continued for 5 minutes before the precepitate was filtered off. The filtercake was dried to 0.50 g (81%) in a desiccator.

$^1$H NMR (DMSO-d$_6$): 5.20 (br. s, 2H), 3.38–3.46 (m, 2H), 3.23–3.31 (m,2H).

$^{13}$C NMR (DMSO-d$_6$): 147.6, 142.3, 72.7, 67.3, 59.1, 51.6.

d. 3,5-Diamino-2,4,6-triiodo-(2-acetoxyethyl)benzene

Acetylation of the product of Example 61c was performed according to the method of Example 24e. The product was isolated in 84% yield.

$^1$H NMR (CDCl$_3$): 4.84 (br. s, 2H), 4.24 (t, 2H, J=7 Hz), 3.56 (t, 2H, J=7 Hz), 2.06 (s, 3H).

e. 3,5-Bis(2,2-dimethyl-1,3-dioxolane-4-carbamido)-2,4,6-triiodo-(2-acetoxyethyl)-benzene 3,5-Diamino-2,4,6-triiodo-(2-acetoxyethyl)benzene was acylated with 2,2-dimethyl-1,3-dioxolane-4-carboxylic chloride (prepared in situ) according to the procedure in Example 29a. After work up, the product was purified by preparative HPLC and isolated in 47% yield.

$^1$H NMR (CDCl$_3$): 8.83, 8.88, 8.97, 9.90 (4s, 2H), 4.60–4.72 (m, 2H,), 4.19–4.44 (m, 4H), 3.78–3.94 (m, 4H), 2.14, 2.06 (2s,3H), 1.67 (s, 3H), 1.47 (s,3H).

f. 3,5-Bis(2,3-dihydroxypropionylamino)-2,4,6-triiodo-(2-hydroxyethyl)benzene

Hydrolysis and ketal cleavage of the product of Example 16e was performed according to the method of Example 30b. After preparative HPLC the product was isolated in 88% yield.

MS (ESP, m/e): 705 ([M]$^+$, 100%).

EXAMPLE 62

3,5-Bis[N-(2-hydroxyethyl)-2,3-dihydroxypropionylamino]-2,4,6-triiodo-(2-hydroxyethyl)benzene a. 3,5-Bis[N-(2-acetoxyethyl)-2,2-dimethyl-1,3-dioxolane-4-carbamido]-2,4,6-triiodo-(2-acetoxyethyl)benzene The product of Example 61e was alkylated with 2-bromoethyl acetate according to the procedure of Example 30a. The product was isolated after preparative HPLC in 68% yield.

$^1$H NMR (CD$_3$CN): 4.25–4.45 (m, 8H), 4.05–4.20 (m, 4H), 3.77–3.95 (m, 4H), 2.06, 1.99, 1.96 (3s, 9H), 1.47, 1.45, 1.44, 1.42, 1.38, 1.27 (6s, 12H).

$^{13}$C NMR (CD$_3$CN): 170.5, 170.4, 170.3, 170.1, 148.4, 110.8, 74.0, 68.0, 61.3, 61.1, 48.6, 48.4, 25.2, 25.1, 25.0, 24.9, 20.3, 20.2.

b. 3,5-Bis-[N-(2-hydroxyethyl)-2,3-dihydroxypropionylamino]-2,4,6-triiodo-(2-hydroxyethyl)benzene Hydrolysis and ketal cleavage of the product of Example 62a followed the procedure in Example 30b. After preparative HPLC the product was isolated in a yield of 72%.

MS (ESP, m/e): 793 ([M]$^+$, 100%).

EXAMPLE 63

3-[N-(2,3-Dihydroxypropyl)-2,3-dihydroxypropionylamino]-5-(2,3-dihydroxypropionylamino)-2,4,6-triiodo-(2-hydroxyethyl)benzene a. 3-[N-(2,2-Dimethyl-1,3-dioxolane-4-methyl)-2,2-dimethyl-1,3-dioxolane-4-carbamido]-5-(2,2-dimethyl-1,3-dioxolane-4-carbamido)-2,4,6-triiodo-(2-acetoxyethyl)benzene N-alkylation of the product of Example 61e with 4-bromomethyl-2,2-dimethyl-1,3-dioxolane was performed according to the method of Example 26a. After work up the product was purified by preparative HPLC, and isolated in 8% yield.

MS (ESP, m/e): 942 ([M]$^+$, 100%).

b. 3-[N-(2,3-Dihydroxyproryl)-2,3-dihydroxypropionylamino]-5-(2,3-dihydroxypropionylamino)-2,4,6-triiodo-(2-hydroxyethyl)benzene Hydrolysis and ketal cleavage of the product of Example 63a were performed according to the method of Example 30b. The product was purified by preparative HPLC and isolated in 52% yield.

MS (ESP, m/e): 779 ([M]$^+$, 100%).

EXAMPLE 64

3,5-Bis-(2,3-dihydroxypropionylamino)-2,4,6-triiodo-(2,3-dihydroxypropyl)-benzene a. 3,5-Dinitro-(3-propenyl)-benzene 3,5-Dinitroiodobenzene (5.0 g, 17.0 mmol), triphenylphosphine (0.54 g, 2.04 mmol), palladium(0) bis (dibenzylideneacetone) (0.23 g, 0.26 mmol) and copper(I) iodide (0.19 g, 1.02 mmol) were all mixed in 75 ml of dioxane. The mixture was heated to 50° C., and allyltributyltin (5.6 g, 17.0 mmol) was added. The temperature was increased to 95° C. and the mixture was stirred under an inert atmosphere. After 36 h a new portion of allyltributyltin was added and after further 36 h a second extra portion of allyltributyltin was added. After 1 week the reaction mixture was cooled to room temperature, and a solution of potassium fluoride (38 g) in water (500 ml) was added. Stirring was continued for 30 minutes. The mixture was extracted with methylene chloride (3×150 ml). The organic phases were washed with water (60 ml), dried (Na$_2$SO$_4$), and the solvent evaporated. The semisolid residue was purified by preparative HPLC, which gave the product as a light yellow syrup. Yield: 0.75 g (21%).

$^1$H NMR (CDCl$_3$): 8.91 (t, 1H, J=2 Hz), 8.40 (d, 2H, J=2H), 5.89–6.04 (m, 1H), 5.18–5.32 (m, 2H), 3.63 (br. d, 2H, J=7 Hz).

$^{13}$C NMR (CDCl$_3$): 169.7, 148.5, 144.5, 133.9, 128.8, 119.1, 116.9, 39.4.

b. 3,5-Dinitro-(2,3-dihydroxypropyl)benzene 3,5-Dinitro-(3-propenyl)benzene (0.10 g, 0.48 mmol) was dissolved in 20 ml of acetone and 2.5 ml of water and the solution cooled in an ice-bath. Osmium tetroxide (17 mg, 0.066 mmol), and an excess of t-butylhydroperoxide, was added. 4-Methylmorpholine N-oxide (0.12 g, 0.96 mmol) was added and the mixture was stirred at room temperature for 48 h. The reaction was then quenched by addition of a saturated solution of sodium hydrogen sulphite (60 ml). The mixture was then extracted with ethyl acetate (2×250 ml). The organic extracts were washed with water (70 ml), dried (Na$_2$SO$_4$), and the solvent evaporated. A white crystalline product 0.11 g (94%) resulted.

$^1$H NMR (CD$_3$CN): 8.82 (t, 1H, J=2 Hz), 8.54 (d, 2H, J=2 Hz), 3.84–3.95 (m, 1H), 3.43–3.58 (m, 2H), 2.88–3.26 (m, 4H).

$^{13}$C NMR (CD$_3$CN): 148.3, 144.2, 130.0, 116.5, 104.8, 71.8, 65.3, 38.6.

c. 3,5-Diamino-(2,3-dihydroxypropyl)benzene-hydrochloride salt 3,5-Dinitro-(2,3-dihydroxypropyl)benzene (0.12 g, 0.49 mmol) was dissolved in 25 ml of methanol. Pd/C (10%, 0.05 g) was added and the substance was hydrogenated in a Parr apparatus at 60 psi. After complete hydrogen consumption the catalyst was filtered off and the filtrate was added to hydrochloric acid (2M, 0.5 ml). The solution was evaporated to dryness. Yield: 0.12 g (100%) after pump drying. The product was used without further purification.

MS (ESP, m/e): 181 ([M]$^+$, 100%).

d. 3,5-Diamino-2,4,6-triiodo-(2,3-dihydroyropyl)benzene 3,5-Diamino-(2,3-dihydroxypropyl)benzene-hydrochloride salt (0.72 g, 2.82 mmol) was dissolved in 25% methanol (8 ml), and hydrochloric acid (2M, 1 ml) was added. To this mixture, with stirring, was added potassium iododichloride (2.27 g, 9.59 mmol, 70% w/w). A precipitate immediately formed and was filtered off after 2 minutes. The filtercake was treated with a saturated solution of sodium hydrogen sulphite (2 ml) and filtered, washed with water (3 ml) and dried. A tan coloured product of 0.96 g (61%) resulted.

MS (ESP, m/e): 560 ([M]$^+$, 40%), 433 ([M-I]$^+$, 10%), 374 ([M-I-CH(OH)CH$_2$OH]$^+$, 100%).

$^1$H NMR (DMSO-d$_6$): 5.20 (br. s, 4H), 3.73–3.94 (m, 1H), 3.58–3.62 (m, 2H), 3.26–3.35 (m, 4H).

e. 3,5-Diamino-2,4,6-triiodo-(2,3-diacetoxypropyl)benzene

Acetylation of the product of Example 64d followed the general method in Example 24e. After work up the product was chromatographed on a short column of alumina with ethyl acetate as the eluent. Evaporation of the solvent gave a white crystalline residue in 70% yield.

$^1$H NMR (CDCl$_3$): 5.47–5.50 (m, 1H), 4.78 (br. s, 4H), 4.19–4.38 (m, 2H), 3.38–3.74 (m, 2H), 2.10 (s, 3H), 1.99 (s,3H).

f. 3,5-Bis-(2,2-dimethyl-1,3-dioxolane-4-carbamido)-2,4,6-triiodo-(2,3-diacetoxypropyl)benzene Acylation of the product of Example 64e with 2,2-dimethyl-1,3-dioxolane-4-carboxylic chloride was effected according to the method in Example 29a. After workup, the crude product was purified by preparative HPLC and isolated in 43% yield.

MS (ESP, m/e): 901 ([M]$^+$, 100%).

g. 3,5-Bis-(2,3-dihydroxypropionylamino)-2,4,6-triiodo-(2,3-dihydroxypropyl)-benzene Hydrolysis and ketal cleavage of the product of Example 64f were performed according to the procedure of Example 29b. After workup the product was purified by preparative HPLC and isolated in 10% yield.

MS (ESP, m/e): 737 ([M]$^+$, 100%).

EXAMPLE 65

Viscosity

The viscosities in aqueous solution at 20° C. for various of the compounds described above were determined as follows:

| Example | Iodine Concentration mgI/mL | Viscosity mPas |
|---|---|---|
| 5 | 435 | 13 |
| 7 | 361 | 8.0 |
| 8 | 370 | 8.3 |
| 9 | 384 | 18 |
| 10 | 381 | 11 |
| 11 | 407 | 16 |
| 13 | 398 | 12 |
| 14 | 373 | 12 |
| 15 | 348 | 7.8 |
| " | 394 | 14 |
| " | 446 | 22 |
| " | 537 | 75 |
| 24 | 430 | 15 |
| 26 | 385 | 13 |
| 27 | 412 | 14 |
| 28 | 404 | 15 |
| 30 | 391 | 21 |
| 32 | 403 | 18 |
| 33 | 370 | 16 |
| 35 | 394 | 15 |
| 36 | 382 | 15 |
| 37 | 458 | 30 |
| 39 | 372 | 15 |

We claim:
1. A compound of formula I

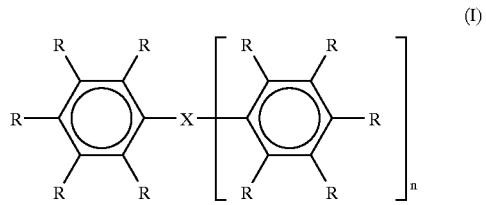

wherein n is 0 or 1, and where n is 1 each C$_6$R$_5$ moiety may be the same or different; each group R is a hydrogen atom, an iodine atom or a hydrophilic moiety M or M$_1$, two or three non-adjacent R groups in each C$_6$R$_5$ moiety being iodine and at least one R group in each C$_6$R$_5$ moiety being M or M$_1$ moieties; where n is 0, X denotes a group R; wherein n is 1, X is a bond, an oxygen atom or a group NR$^1$, CO, SO$_2$, CR$_2^1$, COCO, CONR$^1$, COCR$_2^1$, SOCR$_2^1$, SO$_2$NR$^1$, CR$_2^1$CR$_2^1$, CR$_2^1$NR$^1$, CR$^1{}_2$O, OCONR$^1$, CONR$^1$CO, CONR$^1$CR$^1{}_2$, OCR$^1{}_2$OCR$^1{}_2$, OCR$^1{}_2$CO, CR$^1{}_2$CONR$^1$, CR$^1{}_2$CR$^1{}_2$CR$^1{}_2$, COCR$^1$R$^1$CO, $CR^1{}_2NR^1CR^1{}_2$, $CR^1{}_2SO_2NR^1$, $CR^1{}_2OCO$ or $NR^1SO_2NR^1$, where $R^1$ is hydrogen or a $C_{1-6}$-alkyl or alkoxy group optionally substituted by hydroxy, alkoxy, oxa or oxo and where it is attached to a carbon atom $R^1$ may also be a hydroxyl group; each M independently is a non-ionic hydrophilic straight chain or branched $C_{1-10}$-alkyl group which has one or more $CH_2$ or CH moieties replaced by oxygen or nitrogen atoms and/or which is substituted by one or more groups selected from the group consisting of oxo, hydroxy, amino, carboxyl derivative, and oxo substituted sulphur and phosphorous atoms; and each $M_1$ independently represents a $C_{1-4}$alkyl group substituted by at least one hydroxyl group and optionally linked to the phenyl ring via a carbonyl, sulphone or sulphoxide group, at least one R group being an $M_1$ moiety; with the proviso that where n is zero either at least one $M_1$ group other than a hydroxymethyl or 1,2-dihydroxyethyl group is present or then if one hydroxymethyl or 1,2-dihydroxyethyl $M_1$ group is present at least one nitrogen-attached hydroxylated alkyl moiety-containing M group is also present and isomers thereof.

2. Compounds as claimed in claim 1 wherein n is 1.

3. Compounds as claimed in claim 2 wherein at least one R group in each $C_6R_5$ moiety is an $M_1$ moiety.

4. Compounds as claimed in claim 2 wherein X is an asymmetric group.

5. Compounds as claimed in claim 2 wherein the two $C_6R_5$ groups are different.

6. Compounds as claimed in claim 1 wherein n is zero and the phenyl ring is asymmetrically substituted.

7. Compounds as claimed in claim 2 wherein one $C_6R_5$ group is of formula

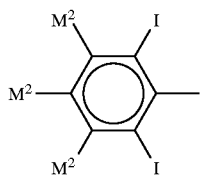

where each $M^2$ independently is a group M or $M^1$.

8. Compounds as claimed in claim 2 wherein one $C_6R_5$ group is of formula

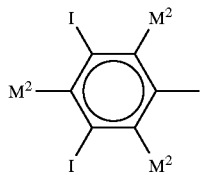

where each $M^2$ independently is a group M or $M^1$.

9. Compounds as claimed in claim 2 wherein each $C_6R_5$ group is of formula

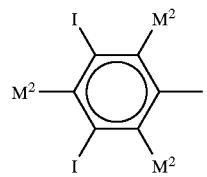

where each $M^2$ independently is a group M or $M^1$.

10. Compounds as claimed in claim 1 wherein the M groups are straight chain or branched $C_{1-10}$-alkyl groups with one or more $CH_2$ or CH moieties replaced by oxygen or nitrogen atoms and substituted by one or more groups selected from oxo, hydroxy, amino, carboxyl derivative, and oxo substituted sulphur and phosphorus atoms.

11. Compounds as claimed in claim 1 wherein the M groups are groups selected from
—CONH—$CH_2CH_2OH$,
—CONH—$CH_2CHOHCH_2OH$,
—CONH—$CH(CH_2OH)_2$,
—CON($CH_2CH_2OH)_2$,
—$CONH_2$,
—$CONHCH_3$,
—$OCOCH_3$,
—N($COCH_3$)H,
—N($COCH_3$)$C_{1-3}$-alkyl,
—N($COCH_3$)-mono, bis or tris-hydroxy $C_{1-4}$-alkyl,
—N($COCH_2OH$)-mono, bis or tris-hydroxy $C_{1-4}$-alkyl,
—N($COCH_2OH)_2$,
—CON($CH_2CHOHCH_2OH$) ($CH_2CH_2OH$),
—CONH—C($CH_2OH)_3$ and
—CONH—CH($CH_2OH$)($CHOHCH_2OH$).

12. Compounds as claimed in claim 1 wherein the $M_1$ groups are selected from $C_{1-4}$-alkyl groups substituted by 1, 2, 3 or 4 hydroxy groups and optionally connected to the phenyl ring via a CO, SO or $SO_2$ group.

13. Compounds as claimed in claim 1 wherein the $M_1$ groups are selected from hydroxymethyl, 2-hydroxyethyl, 2,3-bishydroxy-propyl, 1,3-bishydroxyprop-2-yl, 2,3,4-trihydroxybutyl, 1,2,4-trihydroxybut-2-yl, $COCH_2OH$ and $SO_2CH_2OH$.

14. A diagnostic composition comprising a compound as claimed in any one of claims 1, 15, 16, 17, 18 or 19 together with at least one physiologically tolerable carrier or excipient.

15. A compound of formula II

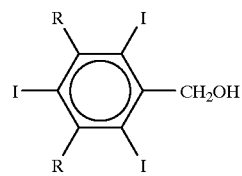

(II)

where each R group, which may be the same or different is a non-ionic hydrophilic moiety substituted by from 1 to 10 hydroxyl groups, or one R group may be a second non-ionic triiodophenyl group, attached directly or via a non-ionic organic linker moiety.

16. A compound as claimed in claim 15 wherein each R group is a hydroxylated alkylaminocarbonyl or alkylcarbonylamino group wherein any alkyl moieties contain 1 to 6 carbon atoms and the amide nitrogens are optionally alkylated by optionally hydroxylated $C_{1-6}$ alkyl groups.

17. A non-ionic iodinated X-ray contrast agent compound comprising a 1-hydroxymethyl-2,4,6-triiodobenzene ring structure having a water solubility of at least 400 mgI/mL at 20° C., and having a viscosity of less than 30 mPas in aqueous solution at 20° C. and at a concentration of 400 mgI/mL.

18. A compound of formula III

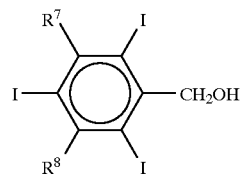

(III)

where $R^7$ and $R^8$, which may be the same or different, are $CH_2OH$, $R^{10}CONR^9$ or $R^{10}CONR^9$;
each $R^9$, which may be the same or different, is hydrogen or linear or branched hydroxylated $C_{1-6}$ alkyl;
and each $R^{10}$, which may be the same or different, is a linear or branched hydroxylated $C_{1-6}$ alkyl.

19. A compound of formula IV

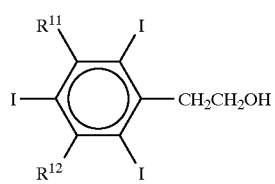

(IV)

wherein $R^{11}$ and $R^{12}$, which may be the same or different, are groups $R^{10}CONR^9$ or $R^{10}NR^9CO$ as defined above with the proviso that at least one is a group $R^{10}CONR^9$.

20. A non-ionic 2,4,6-triiodobenzyl alcohol having a nitrogen attached hydroxylated substituent at at least one of the 3 and 5 positions.

21. In a method of X-ray imaging involving administration of a non-ionic iodinated contrast agent, the improvement comprising using as said contrast agent a compound as claimed in any one of claims 1, 15, 16, 17, 18, 19 and 20.

22. 2,4,6-Triiodo-3-(2,3-dihydroxypropanoylamino)-5-(N-(2,3-dihydroxypropyl)-2,3-dihydroxypropanoylamino) benzyl alcohol.

23. The compound of claim 1 which is 5-[N'-(2,3-Dihydroxypropyl)-hydroxyacetamido]-3-hydroxymethyl-N-(2,3-dihydroxypropyl)-2,4,6-triiodobenzamide.

24. The compound of claim 1 which 5-[N'(2,3-Dihydroxypropyl)-hydroxyacetamido]-3-hydroxymethyl-N-(1,3,4-trihydroxybut-2-yl)-2,4,6-triiodobenzamide.

25. The compound of claim 1 which is 3,5-Bis-(2,3-dihydroxypropionyl-amino)-2,4,6-triiodo-(2,3-dihydroxypropyl)-benzene.

26. A compound of formula I

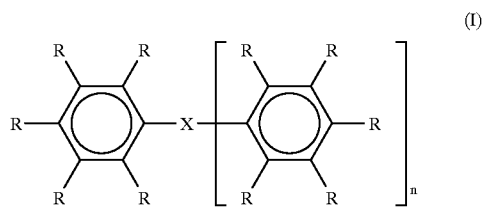

(I)

where n is 1; each $C_6R_5$ moiety may be the same or different; each group R is a hydrogen atom, an iodine atom or a hydrophilic moiety M or $M_1$, two or three non-adjacent R groups in each $C_6R_5$ moiety being iodine and at least one R group in each $C_6R_5$ moiety being M or $M_1$ moieties; X is —$NR^1COCONR^1$—, —$NR^1COCR^1{}_2CONR^1$—, $NR^1CR^1{}_2CR^1OHCR^1{}_2NR^1$—, —$CONR^1CR^1{}_2CONR^1$—, or —$N(COR^1)CR^1{}_2CR^1OHN(COR^1)$— where $R^1$ is hydrogen or a $C_{1-6}$-alkyl or alkoxy group optionally substituted by hydroxy, alkoxy, oxa or oxo and where it is attached to a carbon atom $R^1$ may also be a hydroxyl group; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group being an $M_1$ moiety; and isomers thereof.

* * * * *